United States Patent
Panicali et al.

(10) Patent No.: US 8,901,093 B2
(45) Date of Patent: Dec. 2, 2014

(54) CUSTOM VECTORS FOR TREATING AND PREVENTING PANCREATIC CANCER

(75) Inventors: Dennis L. Panicali, Acton, MA (US); Gail P. Mazzara, Winchester, MA (US); Linda R. Gritz, Somerville, MA (US); Jeffrey Schlom, Potomac, MD (US); Kwong-Yok Tsang, Bethesda, MD (US); James W. Hodge, Gaithersberg, MD (US)

(73) Assignee: The United States of America, as represented by the Secretary of the Department of Health and Human Services, Washington, DC (US)

( * ) Notice: Subject to any disclaimer, the term of this patent is extended or adjusted under 35 U.S.C. 154(b) by 1217 days.

(21) Appl. No.: 10/579,025

(22) PCT Filed: Nov. 12, 2004

(86) PCT No.: PCT/US2004/038643
§ 371 (c)(1),
(2), (4) Date: Oct. 19, 2006

(87) PCT Pub. No.: WO2005/046622
PCT Pub. Date: May 26, 2005

(65) Prior Publication Data
US 2008/0166367 A1 Jul. 10, 2008

Related U.S. Application Data

(60) Provisional application No. 60/519,354, filed on Nov. 12, 2003.

(51) Int. Cl.
| | | |
|---|---|---|
| A61K 48/00 | (2006.01) | |
| C12N 5/00 | (2006.01) | |
| C12N 5/02 | (2006.01) | |
| C12N 15/00 | (2006.01) | |
| A61K 39/00 | (2006.01) | |
| A61K 39/38 | (2006.01) | |
| A61K 39/225 | (2006.01) | |
| A01N 63/00 | (2006.01) | |
| A01N 65/00 | (2009.01) | |
| C12N 15/86 | (2006.01) | |
| C12N 7/00 | (2006.01) | |

(52) U.S. Cl.
CPC ...... *C12N 15/86* (2013.01); *C12N 2710/24071* (2013.01); *A61K 2039/545* (2013.01); *C12N 2710/24143* (2013.01); *C12N 2710/24043* (2013.01); *A61K 2039/53* (2013.01); *A61K 2039/55516* (2013.01); *C12N 7/00* (2013.01); *C12N 2710/24171* (2013.01); *A61K 39/0011* (2013.01)
USPC ... 514/44 R; 435/325; 435/320.1; 424/184.1; 424/223.1; 424/93.1; 424/93.21

(58) Field of Classification Search
CPC ............... C12N 15/86; C12N 2710/24071; C12N 2710/24143; C12N 2710/24043; C12N 7/00; C12N 2710/24171; A61K 2039/545; A61K 2039/53; A61K 2039/55516; A61K 39/0011
USPC ........... 514/44 R; 435/325, 320.1; 424/184.1, 424/223.1, 93.1, 93.21
See application file for complete search history.

(56) References Cited

U.S. PATENT DOCUMENTS

| | | | |
|---|---|---|---|
| 5,827,666 A | 10/1998 | Finn et al. | |
| 6,537,552 B1 | 3/2003 | Minion et al. | |
| 7,273,605 B2 * | 9/2007 | Laidlaw et al. | 424/93.2 |
| 2007/0110718 A1 | 5/2007 | Panicali et al. | |

FOREIGN PATENT DOCUMENTS

| | | |
|---|---|---|
| WO | WO 98/04727 | 2/1998 |
| WO | WO 00/34494 A1 | 6/2000 |
| WO | WO 01/24832 A2 | 4/2001 |
| WO | WO 02/101075 A2 | 12/2002 |
| WO | WO 03/031569 A2 | 4/2003 |
| WO | WO 03/085087 A2 | 10/2003 |
| WO | WO 03/100060 A2 | 12/2003 |
| WO | WO 03/106648 A2 | 12/2003 |

OTHER PUBLICATIONS

Taylor-Papadimitriou et al., MUC1 and cancer. Biochim Biophys Acta. 1455(2-3):301-13, 1999.*
Kotera et al., Humoral immunity against a tandem repeat epitope of human mucin MUC-1 in sera from breast, pancreatic, and colon cancer patients. Cancer Res. 54(11):2856-60, 1994.*
Wellington et al., Measles, mumps, rubella vaccine (Priorix; GSK-MMR): a review of its use in the prevention of measles, mumps and rubella. Drugs 63(19):2107-26, 2003.*
Kufe, Nature, 9: 874-885, 2009.*
Aarts, Wilhelmina M. et al.; Cancer Research; 62:5770-5777 (Oct. 15, 2002).
Schlom, Jeffrey et al.; Breast Cancer Research and Treatment; 38:27-39 (1996).
Scholl, Susy et al.; Journal of Biomedicine and Biotechnology; 3:194-201 (2003).
Zajac, P. et al.; Human Gene Therapy; 14:1497-1510 (Nov. 1, 2003).
Grosenbach et al., Cancer Research, Jun. 2001, vol. 61, 4497-4050.
Greiner et al., Cancer Research, Dec. 2002, vol. 62, 6944-6951.
Ligtenberg et al., "Epidialin, A Carcinoma-Associated Mucin, Is Generated by a Polymorphic Gene Encoding Splice Variants with Alternative Amino Termini," *Journal of Biological Chemistry*, vol. 265, No. 10, pp. 5573-5578 (1990).
Zrihan-Licht et al., "Characterization and Molecular Cloning of a Novel MUC1 Protein, Devoid of Tandem Repeats, Expressed in Human Breast Cancer Tissue," *European Journal of Biochemistry*, vol. 224, No. 2, pp. 787-795 (1994).
Search Report for EP 04811370.8, completed Apr. 8, 2008.
Hodge et al., *Cancer Research*, 59: 5800-5807 (1999).

(Continued)

*Primary Examiner* — Thaian N Ton
(74) *Attorney, Agent, or Firm* — Leydig, Voit & Mayer, Ltd.

(57) ABSTRACT

The present invention is directed to a system for treating individuals at risk of developing or suffering from pancreatic cancer. The system comprises administering to the individual a recombinant poxvirus, where the poxvirus contains a foreign nucleic acid encoding at least one pancreatic tumor associated antigen (PTAA).

24 Claims, 14 Drawing Sheets

(56) References Cited

OTHER PUBLICATIONS

Hodge et al., *Clinical Cancer Research*, 9: 1837-1849 (2003).
Tsang et al., *Clinical Cancer Research*, 11: 1597-1607 (2005).
Brody et al., *Immunology*, 22: 75-85 (1972).
Gulley et al., *Clin. Cancer Res.*, 14(10): 3060-3069 (2008).
Kaufman et al., *Journal of Translational Medicine*, 10 pages (2007).
Palmowski et al., *Journal of Immunology*, 168: 4391-4398 (2002).
Schuetz et al., *J. Clin. Oncol., 2005 ASCO Annual Meeting Proceedings*, 23(16S Part I of II in Jun. 1 Supplement): 2576; Abstract Only (2005).
Sutter et al., *PNAS*, 89: 10847-10851 (1992).
Tartaglia et al., *Virology*, 188: 217-232 (1992).
Williamson et al., *Journal of General Virology*, 71: 2761-2767 (1990).
Kaufman, et al., "Immunotherapy for pancreatic cancer: current concepts," *Hematol. Oncol. Clin. N. Amer.*, 16: 159-197 (2002).
Madan et al., *2007 Breast Cancer Symposium*, Abstract 237 (2007).
Mohebtash et al., *J. Clin. Oncol., 2008 ASCO Annual Meeting Proceedings 26*, 3035 (2008).
Apostolopoulos et al., "Cellular Mucins: Targets for Immunotherapy," *Critical Reviews in Immunology*, 14: 293-309 (1994).
Marshall, John, "Carcinoembryonic Antigen-Based Vaccines," *Seminars in Oncology*, 30(3): 30-36 (2003).
Reynolds, et al., "HLA-Independent Heterogeneity of CD8+ T Cell Responses to MAGE-3, Melan-A/MART-1, gp100, Tyrosinase, MC1R, and TRP-2 in Vaccine-Treated Melanoma Patients," *Journal of Immunology*, 161: 6970-6976 (1998).

\* cited by examiner

Restriction Endonuclease Map of Plasmid pT2137 rV-MUC-1 Vector Schematic

Restriction Endonuclease Map of Plasmid pT8016

Figure 4

Generation of rV-CEA(6D)/TRICOM Recombinant Vaccinia Virus

Restriction Endonuclease Map of Plasmid pT2187

Figure 6

Generation of rF-CEA(6D)/TRICOM Recombinant Fowlpox Virus

```
   1 ATGACACCGG GCACCCAGTC TCCTTTCTTC CTGCTGCTGC TCCTCACAGT GCTTACAGTT
  61 GTTACGGGTT CTGGTCATGC AAGCTCTACC CCAGGTGGAG AAAAGGAGAC TTCGGCTACC
 121 CAGAGAAGTT CAGTGCCCAG CTCTACTGAG AAGAATGCTG TGAGTATGAC AAGCTCCGTA
 181 CTCTCCAGCC ACAGCCCGG TTCAGGCTCC TCCACCACTC AGGGACAGGA TGTCACTCTG
 241 GCCCCGGCCA CGGAACCAGC TTCAGGTTCA GCTGCCTTGT GGGGACAGGA TGTCACCCTC
 301 GTACCAGTTA CTAGACCAGC TTTAGGTAGC ACAGCACCTC CTGCTCATGG AGTAACTAGT
 361 GCTCCTGATA CTCGTCCAGC TCCTGGCAGT ACTGCACCAC CGGCACATGG CGTAACATCA
 421 GCACCTGATA CAAGACCTGC ACCTGGATCT ACAGCGCCGC CTGCGCACGG AGTGACATCG
 481 GCGCCCGATA CGCGCCCCGC TCCCGGTAGC ACCGCACCGC CCGCCCACGG TGTTACAAGT
 541 GCACCCGATA CCCGGCCGGC ACCCGGAAGT ACCGCTCCAC CTGCACACGG GGTCACAAGC
 601 GCGCCAGACA CTCGACCTGC GCCAGGGTCG ACTGCCCCTC CGGCGCATGG TGTGACCTCA
 661 GCTCCTGACA CAAGGCCAGC CCAGCTAGC ACTCTGGTGC ACAACGGCAC CTCTGCCAGG
 721 GCTACCACAA CCCCAGCCAG CAAGAGCACT CCATTCTCAA TTCCCAGCCA CCACTCTGAT
 781 ACTCCTACCA CCCTTGCCAG CCATAGCACC AAGACTGATG CCAGTAGCAC TCACCATAGC
 841 ACGGTACCTC CTCTCACCTC CTCCAATCAC AGCACTTCTC CCCAGTTGTC TACTGGGGTC
 901 TCTTTCTTTT TCCTGTCTTT TCACATTTCA AACCTCCAGT TTAATTCCTC TCTGAAGAT
 961 CCCAGCACCG ACTACTACCA AGAGCTGCAG AGAGACATTT CTGAAATGTT TTTGCAGATT
1021 TATAAACAAG GGGGTTTTCT GGGCCTCTCC AATATTAAGT TCAGGCCAGG ATCTGTGGTG
1081 GTACAATTGA CTCTGGCCTT CCGAGAAGGT ACCATCAATG TCCACGACGT GGAGACACAG
1141 TTCAATCAGT ATAAAACGGA AGCAGCCTCT CGATATAACC TGACGATCTC AGACGTCAGC
1201 GTGAGTGATG TGCCATTTCC TTTCTCTGCC CAGTCTGGGG CTGGGGTGCC AGGCTGGGGC
1261 ATCGCGCTGC TGGTGCTGGT CTGTGTTCTG GTTGCGCTGG CCATTGTCTA TCTCATTGCC
1321 TTGGCTGTCT GTCAGTGCCG CCGAAAGAAC TACGGGCAGC TGGACATCTT TCCAGCCCGG
1381 GATACCTACC ATCCTATGAG CGAGTACCCC ACCTACCACA CCCATGGGCG CTATGTGCCC
1441 CCTAGCAGTA CCGATCGTAG CCCCTATGAG AAGGTTTCTG CAGGTAATGG TGGCAGCAGC
1501 CTCTCTTACA CAAACCCAGC AGTGGCAGCC ACTTCTGCCA ACTTGTAG
```

FIGURE 7

SEQUENCE OF wMUC-1(6), SEQ. ID. NO: 1

```
MTPGTQSPFFLLLLLTVLTVVTGSGHASSTPGGEKETSATQRSSVPSSTEKNAV
SMTSSVLSSHSPGSGSSTTQGQDVTLAPATEPASGSAALWGQDVTSVPVTRPAL
GSTAPPAHGVTSAPDTRPAPGSTAPPAHGVTSAPDTRPAPGSTAPPAHGVTSAP
DTRPAPGSTAPPAHGVTSAPDTRPAPGSTAPPAHGVTSAPDTRPAPGSTAPPAH
GVTSAPDTRPAPASTLVHNGTSARATTTPASKSTPFSIPSHHSDTPTTLASHST
KTDASSTHHSTVPPLTSSNHSTSPQLSTGVSFFFLSFHISNLQFNSSLEDPSTD
YYQELQRDISEMFLQIYKQGGFLGLSNIKFRPGSVVVQLTLAFREGTINVHDVE
TQFNQYKTEAASRYNLTISDVSVSDVPFPFSAQSGAGVPGWGIALLVLVCVLVA
LAIVYLIALAVCQCRRKNYGQLDIFPARDTYHPMSEYPTYHTHGRYVPPSSTDR
SPYEKVSAGNGGSSLSYTNPAVAATSANL
```

FIGURE 8

AMINO ACID SEQUENCE OF wMUC-1(6), SEQ. ID. NO: 2

```
   1 ATGGAGTCTC CCTCGGCCCC TCCCCACAGA TGGTGCATCC CCTGGCAGAG GCTCCTGCTC
  61 ACAGCCTCAC TTCTAACCTT CTGGAACCCG CCCACCACTG CCAAGCTCAC TATTGAATCC
 121 ACGCCGTTCA ATGTCGCAGA GGGGAAGGAG GTGCTTCTAC TTGTCCACAA TCTGCCCCAG
 181 CATCTTTTTG GCTACAGCTG GTACAAAGGT GAAAGAGTGG ATGGCAACCG TCAAATTATA
 241 GGATATGTAA TAGGAACTCA ACAAGCTACC CCAGGGCCCG CATACAGTGG TCGAGAGATA
 301 ATATACCCCA ATGCATCCCT GCTGATCCAG AACATCATCC AGAATGACAC AGGATTCTAC
 361 ACCCTACACG TCATAAAGTC AGATCTTGTG AATGAAGAAG CAACTGGCCA GTTCCGGGTA
 421 TACCCGGAAC TCCCTAAGCC TTCTATTAGC TCCAATAATA GTAAGCCTGT CGAAGACAAA
 481 GATGCCGTCG CTTTTACATG CGAGCCCGAA ACTCAAGACG CAACATATCT CTGGTGGGTG
 541 AACAACCAGT CCCTGCCTGT GTCCCCTAGA CTCCAACTCA GCAACGGAAA TAGAACTCTG
 601 ACCCTGTTTA ACGTGACCAG GAACGACACA GCAAGCTACA AATGCGAAAC CCAAAATCCA
 661 GTCAGCGCCA GGAGGTCTGA TTCAGTGATT CTCAACGTGC TTTACGGACC CGATGCTCCT
 721 ACAATCAGCC CTCTAAACAC AAGCTATAGA TCAGGGGAAA ATCTGAATCT GAGCTGTCAT
 781 GCCGCTAGCA ATCCTCCCGC CCAATACAGC TGGTTTGTCA ATGGCACTTT CCAACAGTCC
 841 ACCCAGGAAC TGTTCATTCC CAATATTACC GTGAACAATA GTGGATCCTA CACGTGCCAA
 901 GCTCACAATA GCGACACCGG ACTCAACCGC ACAACCGTGA CGACGATTAC CGTGTATGAG
 961 CCACCAAAAC CATTCATAAC TAGTAACAAT TCTAACCCAG TTGAGGATGA GGACGCAGTT
1021 GCATTAACTT GTGAGCCAGA GATTCAAAAT ACCACTTATT TATGGTGGGT CAATAACCAA
1081 AGTTTGCCGG TTAGCCCACG CTTGCAGTTG TCTAATGATA ACCGCACATT GACACTCCTG
1141 TCCGTTACTC GCAATGATGT AGGACCTTAT GAGTGTGGCA TTCAGAATGA ATTATCCGTT
1201 GATCACTCCG ACCCTGTTAT CCTTAATGTT TTGTATGGCC CAGACGACCC AACTATATCT
1261 CCATCATACA CCTACTACCG TCCCGGCGTG AACTTGAGCC TTTCTTGCCA TGCAGCATCC
1321 AACCCCCCTG CACAGTACTC CTGGCTGATT GATGGAAACA TTCAGCAGCA TACTCAAGAG
1381 TTATTTATAA GCAACATAAC TGAGAAGAAC AGCGGACTCT ATACTTGCCA GGCCAATAAC
1441 TCAGCCAGTG GTCACAGCAG GACTACAGTT AAAACAATAA CTGTTTCCGC GGAGCTGCCC
1501 AAGCCCTCCA TCTCCAGCAA CAACTCCAAA CCCGTGGAGG ACAAGGATGC TGTGGCCTTC
1561 ACCTGTGAAC CTGAGGCTCA GAACACAACC TACCTGTGGT GGGTAAATGG TCAGAGCCTC
1621 CCAGTCAGTC CCAGGCTGCA GCTGTCCAAT GGCAACAGGA CCCTCACTCT ATTCAATGTC
1681 ACAAGAAATG ACGCAAGAGC CTATGTATGT GGAATCCAGA ACTCAGTGAG TGCAAACCGC
1741 AGTGACCCAG TCACCCTGGA TGTCCTCTAT GGGCCGGACA CCCCCATCAT TTCCCCCCCA
1801 GACTCGTCTT ACCTTTCGGG AGCGGACCTC AACCTCTCCT GCCACTCGGC CTCTAACCCA
1861 TCCCCGCAGT ATTCTTGGCG TATCAATGGG ATACCGCAGC AACACACACA AGTTCTCTTT
1921 ATCGCCAAAA TCACGCCAAA TAATAACGGG ACCTATGCCT GTTTTGTCTC TAACTTGGCT
1981 ACTGGCCGCA ATAATTCCAT AGTCAAGAGC ATCACAGTCT CTGCATCTGG AACTTCTCCT
2041 GGTCTCTCAG CTGGGGCCAC TGTCGGCATC ATGATTGGAG TGCTGGTTGG GGTTGCTCTG
2101 ATATAG
```

FIGURE 9

DNA SEQUENCE OF wCEA(6D), SEQ. ID. NO: 3 nsnpvededavaltcepeiqnttylwwvnnqslpvsprlqlsndnrtltllsvtrndvgpy
ecgiqnelsvdhsdpvilnvlygpddptispsytyyrpgvnlslschaasnppaqyswlid
gniqqhtqelfisniteknsglytcqannsasghsrttvktitvsaelpkpsissnnskpv
edkdavaftcepeaqnttylwwvngqslpvsprlqlsngnrtltlfnvtrndarayv
cgiqnsvsanrsdpvtldvlygpdtpiisppdssylsgadlnlschsasnpspqyswrin
gipqqhtqvlfiakitpnngtyacfvsnlatgrnnsivksitvsasgtspglsagatvg
imigvlvgvali AMINO ACID SEQUENCE OF HUMAN wCEA(6D),
SEQ.ID.NO:4

*FIG. 10*

PANVAC-F Plasmids pT1154 and pT8150

FIGURE 12

GENERATION OF PANVAC-V RECOMBINANT VACCINIA VIRUS

RESTRICTION ENDONUCLEASE MAP OF PLASMID PT1153

Figure 14

Derivation of Parental Virus TBC-vTRICOM

CUSTOM VECTORS FOR TREATING AND PREVENTING PANCREATIC CANCER

CROSS-REFERENCE TO RELATED APPLICATIONS

The present application is a 371 National Phase Entry Application of co-pending International Application PCT/US2004/038643, filed Nov. 12, 2004, which designated the U.S. and claims benefit under 35 U.S.C. 119(e) of U.S. Provisional Application No. 60/519,354, filed Nov. 12, 2003, the contents of which are incorporated herein by reference in their entirety.

FIELD OF THE INVENTION

The present invention relates to the field of immunizations and the use of targeted immunotherapy to effect disease onset and/or disease progression for pancreatic cancer. The present invention also relates to human cancer immunotherapy.

BACKGROUND OF THE INVENTION

Pancreatic cancer is the fourth leading cause of cancer deaths in men and women in the United States. The American Cancer Society estimates that in the United States in 2003, there will be 30,700 new cases of pancreatic cancer and 30,000 deaths. Thus, the prognosis for pancreatic cancer is extremely poor.

Cancer of the pancreas generally develops without early symptoms. If a cancer develops in an area of the pancreas near the common bile duct, its blockage may lead to jaundice (yellowing of the skin and eyes due to pigment accumulation). Sometimes this symptom allows the tumor to be diagnosed at a relatively early stage. At present, only biopsy yields a certain diagnosis. Because of the "silent" early course of the disease, the need for biopsy may become obvious only with advanced disease.

Cigarette and cigar smoking increase the risk of pancreatic cancer; incidence rates are more than twice as high for smokers as for non-smokers. Other risk factors include obesity, physical inactivity, chronic pancreatitis, diabetes, and cirrhosis. Pancreatic cancer rates are higher in countries whose populations eat a diet high in fat. Rates are slightly higher in males than in females.

Surgery, radiation therapy, and chemotherapy are the current treatment options. Depending on the stage of the pancreatic cancer, two or even three types of treatment may be used, either simultaneously or sequentially. However, although these treatments can extend survival and/or relieve symptoms in many patients, they seldom produce a cure.

In addition to the poor efficacy of currently available treatments, these current options are also associated with significant side effects. There are two types of surgery for pancreatic cancer, depending on the goal of the treatment. If the tumor is small enough that there is a chance it can all be removed, then the goal can be to completely excise the tumor. However, the cancer may have already metastasized, in which case even complete removal of the tumor will not present a cure. The second type of surgery is palliative surgery, which is used when the cancer is too widespread to be completely removed, and is designed to relieve symptoms or prevent other future problems.

Radiation therapy is treatment with high energy rays such as x-rays to kill pr shrink cancer cells, using either an internal or external source. Radiation, often combined with chemotherapy, can be used for patients whose tumors are too widespread to be removed surgically. Side effects of radiation therapy include mild skin changes that look like sunburn or suntan, upset stomach, loose bowels, and tiredness.

A wide variety of drugs are used for chemotherapy of pancreatic cancer. Side effects depend on the type of drugs administered, the dosage, and the duration of the treatment. Temporary side effects include nausea and vomiting, loss of appetite, hair loss, and mouth sores. Low blood cell counts from treatment can cause an increased risk of infection, bleeding or bruising after minor cuts, and fatigue. In addition, pain can be a real concern for pancreatic cancer patients.

Accordingly, there is a need for improved methods of prevention and treatment of pancreatic cancer.

As a result of advances in molecular genetics and genomics, a number of genes involved in pancreatic cancer have been identified. Therefore, it would be advantageous to develop a treatment to utilize the specific information which can be obtained from genetic and expression analysis, to develop more effective treatment methods than are currently available.

One recent approach to the treatment of cancer is immunotherapy, which is based on the observation that human tumor cells express a variety of tumor-associated antigens (TAAs) that are not expressed or are minimally expressed in normal tissues. These antigens, which include viral tumor antigens, cellular oncogene proteins, and tissue-specific differentiation antigens, can serve as targets for the host immune system and elicit responses that result in tumor destruction. This immune response is mediated primarily by lymphocytes; T cells in general and class I MHC-restricted cytotoxic T lymphocytes in particular play a central role in tumor rejection. Unfortunately, as evidenced by the high incidence of cancer in the population, the immune response to neoplastic cells often fails to eliminate tumors. The goal of active cancer immunotherapy is to augment anti-tumor responses, particularly T cell responses, in order to effect complete tumor destruction.

Most attempts at active immunization against cancer antigens have utilized whole tumor cells or tumor cell fragments as immunogens. However, this approach does not afford reproducibility or control over the precise antigens included in each immunization.

The cloning of genes encoding TAAs has opened new possibilities for the immunotherapy of cancer based on the use of recombinant or synthetic anti-cancer vaccines: Tsang et al., *J. Natl. Cancer Inst.* 87: 982-90 (1995); Kawakami et al., *Proc. Natl. Acad. Sci. USA* 91:6458-62 (1994). In recent years, much effort has been expended on gene therapy as a means of combating cancer. The term "gene therapy" has been used to describe a wide variety of methods using recombinant biotechnology techniques to deliver different materials to a cell. Such methods include, for example, the delivery of a gene, antisense RNA, a cytotoxic agent, etc., by a vector to a mammalian cell, preferably a human cell either in vivo or ex vivo. Most of the initial work has focused on the use of retroviral vectors to transform these cells. This focus has resulted from the ability of retroviruses to infect cells and have their genetic material integrated into the host cell with high efficiency. The retroviral vector is typically a modified virus such as Moloney Murine Leukemia Virus (MMLV), which has had its packaging sequences deleted to prevent packaging of the entire retroviral genome.

However, numerous difficulties with retroviruses have been reported. One problem that has developed was initially seen as a key advantage of the virus, namely, the ability of the virus to integrate into the chromosome. However, such integration can be problematic, depending on the chromosomal site of viral insertion. A number of other viruses that were initially believed to be largely episomal in nature such as adenoassociated virus (AAV) have also turned out to have this property. While advantageous in causing long-term expression, it also provides the potential for problems such as undesirable cellular transformation. The stable transformation of a patient's somatic cells makes it difficult to reverse the treatment regimen if undesirable side effects dictate that it should be stopped.

Problems, have also been encountered in infecting certain cells. Retroviruses typically enter cells through cell surface receptors. If such receptors are not present on the cell, or not present in sufficient numbers, then infection may not be possible, or may be inefficient. These viruses are also relatively labile in comparison to other viruses. Outbreaks of wild-type virus from recombinant virus-producing cell lines have also been reported, with the vector itself causing a disease. Moreover, many of these viruses only allow gene expression in dividing cells. Viral vectors based upon lentiviruses such as the Human Immunodeficiency Virus (HIV) do not have these problems, but concerns remain about using such viruses as vectors.

Other viruses have been proposed as vectors, such as herpes virus. In addition, various non-viral vectors such as ligand-DNA-conjugates have been proposed. Nevertheless, these approaches all pose certain problems. For example, a vector must not itself become a potential source for infection to the individual treated. However, as already mentioned, outbreaks of wild-type retroviruses have been reported in some cell lines. Similarly, the use of herpes virus as a vector has been found to result in persistence of the virus. Furthermore, many of these vectors can contain and express only a relatively small amount of genetic material. This is undesirable for numerous situations in which the ability to express multiple products is preferred.

Poxviruses have been used for many years as vectors, particularly with respect to providing a foreign antigen or self-antigen to generate an immune response in a host. The advantages of the poxvirus vectors include: (i) ease of generation and production; (ii) the large size of the genome permitting insertion of multiple genes; (iii) efficient delivery of genes to multiple cell types, including antigen-presenting cells; (iv) high levels of protein expression; (v) optimal presentation of antigens to the immune system; (vi) the ability to elicit cell-mediated immune responses as well as antibody responses; and (vii) the long-term experience gained with using this vector in humans as a smallpox vaccine.

Attention has focused on orthopox such as Wyeth, NYVAC (U.S. Pat. No. 5,364,773) and modified vaccinia Ankara (MVA). MVA was derived from the Ankara vaccinia strain CVA-1 which was used in the 1950s as a smallpox vaccine. In 1958, attenuation experiments were initiated in the laboratory of Dr. Anton Mayr (University of Munich), comprising terminal dilution of CVA in chicken embryo fibroblast (CEF) cells that ultimately resulted in over 500 passages. The resulting MVA is an attenuated, replication-defective virus, which is restricted to replication primarily in avian cells. Comparison of the MVA genome to its parent, CVA, revealed 6 major deletions of genomic DNA (deletion I, II, III, IV, V, and VI), totaling 31,000 basepairs. Meyer et al., J. Gen. Virol. 72:1031-8 (1991). MVA has been administered to numerous animal species, including monkeys, mice, swine, sheep, cattle, horses and elephants with no local or systemic adverse effects. Over 120,000 humans have been safely vaccinated with MVA by intradermal, subcutaneous or intramuscular injections. MVA has also been reported to be a virulent among normal and immunosuppressed animals (Mayr et al., Zentralb. Bakteriol. 167:375-90 (1978). Accordingly, in addition to utility as a smallpox vaccine, the more attenuated strains are particularly attractive poxviruses for use as vectors for immune modulation and gene therapy.

Consequently, poxviruses can be genetically engineered to contain and express foreign DNA with or without impairing the ability of the virus to replicate. Such foreign DNA can encode protein antigens that induce an immune protection in a host inoculated with such recombinant poxvirus. For example, recombinant vaccinia viruses have been engineered to express immunizing antigens of herpes virus, hepatitis B, rabies, influenza, human immunodeficiency virus (HIV), and other viruses (Kieny et al., Nature 312:163-6 (1984); Smith et al., Nature 302: 490-5 (1983); Smith et al., Proc. Natl. Acad. Sci. USA 80:7155-9 (1983); Zagury et al., Nature 326:249-50 (1987); Cooney et al., Lancet 337:567-72 (1991); and Graham et al., J. Infect. Dis. 166:244-52 (1992)). Recombinant vaccinia viruses have also been shown to elicit immune responses against influenza virus, dengue virus, respiratory syncytial virus, and human immunodeficiency virus. Pox viruses have also been used to generate immune reactions against tumor-associated antigens such as EEA, PSA and MUC. See also U.S. Pat. No. 5,656,465.

However, because poxviruses are cytoplasmic viruses and thus DNA does not generally integrate into the host cell's chromosomes, pox vectors are usually not the first choice for gene therapy where a continuous source of an agent is needed for an extended period of time.

In view of the very poor prognosis of pancreatic cancer, and the lack of significant survival provided by the currently available treatments, there is a need for improved methods of treatment for pancreatic cancer.

SUMMARY OF THE INVENTION

We have now discovered a new method for treating pancreatic cancer in humans involving the use of recombinant poxviruses containing pancreatic tumor associated antigens and immune modulating molecules. Accordingly, the present invention provides a system for screening individuals to identify those at risk of developing or suffering from pancreatic cancer. Preferably, the subject is a human. The system also comprises administering to that individual at risk for developing or suffering from pancreatic cancer a first recombinant poxvirus, and at regular intervals thereafter administering a second recombinant poxvirus, wherein the recombinant poxviruses comprise at least one gene encoding a pancreatic tumor associated antigen (PTAA), preferably two PTAAs. Preferred pancreatic tumor associated antigens are CEA and MUC-1, and variants thereof. Preferred variants include wCEA(6D) and wMUC-1(6). Other preferred variants have sequence changes to create a more immunogenic CTL epitope. Preferably, the second recombinant poxvirus is from a different genus than the first recombinant poxvirus. The genes encoding the PTAAs are preferably inserted into a nonessential region of the poxvirus genome. Preferred poxviruses include orthopox, such as vaccinia, and avipox, such as fowlpox and canary pox.

The invention also provides co-administration of granulocyte macrophage-stimulating factor with the recombinant poxviruses, as well as co-administration of immune modulating molecules, such as at least one co-stimulatory molecule, such as LFA-3, ICAM-1, and B7.1. Preferably, one uses a combination of LFA-3, ICAM-1, and B7.1 (referred to as TRICOM™).

Due to their large genome, the recombinant poxviruses according to the present invention can be constructed as a single vehicle to deliver all of the therapeutically necessary molecules, including pancreatic cancer associated antigens and/or co-stimulatory molecules, in the same vector.

In one embodiment, the system comprises administering to an individual an initial "prime" with a composition containing one or more recombinant poxvirus, followed by one or preferably multiple "boosts" with a composition containing one or more poxvirus vectors.

The initial priming vaccination may comprise one or more poxvirus vectors. In one preferred embodiment, a single poxvirus vector is used for delivery of the PTAAs and co-stimulatory molecules. In another embodiment, two or more poxvirus vectors comprise the priming vaccination, which are administered simultaneously in a single injection. For example, simultaneously administering to a host an admix of two poxvirus vectors, at least one of which is replication competent. If both vectors are replication defective, then not as many cells will get transduced by both viruses. One example of an admix strategy is to use a first vector comprising a DNA encoding at least one pancreatic cancer associated antigen and a second vector comprising a DNA encoding at least one, preferably three, co-stimulatory molecules such as TRICOM.

The boosting vaccinations may also comprise one or more poxvirus vectors. In one preferred embodiment, a single poxvirus vector is used for delivery of the PTAAs and co-stimulatory molecules of the boosting vaccination. In another embodiment, two or more poxvirus vectors comprise the boosting vaccination, which are administered simultaneously in a single injection, as described above as the admix strategy.

In one preferred embodiment, different poxviruses can be used to provide a heterologous prime/boost protocol using pox vectors carrying different sets of therapeutic molecules, for inoculations at different time intervals. One preferred heterologous prime/boost combination is priming with a first orthopox vector composition and boosting with a second avipox vector composition. The boosting vector can be administered every 2-4 weeks, for example, for a total of at least 5-15 boosting vaccinations. For example, a protocol of 3 administrations of vaccinia at a regular, e.g., monthly, intervals followed by multiple administrations of fowlpox at regular intervals, e.g., monthly. In one preferred embodiment, the orthopox is vaccinia, more preferably a vaccinia such as Wyeth or MVA or NYVAC. One can also add other components to the protocol such as further boosting or priming administration of DNA or protein. In an alternative embodiment, the genes can be in multiple poxvirus vectors that are administered at about the same time, rather than in a single vector.

Any pancreatic tumor associated antigen can be used in the present vector system. CEA, MUC-1, mini-MUC, and the mucins, including MUC-4, are particularly preferred PTAAS.

The list of pancreatic tumor associated antigens continues to increase. Preferred pancreatic cancer associated antigens for use in the present invention include CEA, also referred to as carcinoembryonic antigen (Clin. Cancer Res. 6:4176-85, 2000); MUC-1 (Marshall et al., *J Clin Oncol.*, 18:3964-73 (2000)); mini-MUC-1; GM-CSF (U.S. Pat. No. 6,350,455); MUC-4 (U.S. Published Patent Application No. 20020150894); MUC-2; MUC-3; MUC-5AC; MUC-5B; MUC-6; MUC-7; MUC-11; MUC-12; k-ras (U.S. Pat. No. 6,350,455; U.S. Pat. No. 5,985,290); ras peptides, including peptides that correspond to the mutation harbored in an individual's tumor (Chiba et al., *Oncogene* 5:1603-10 (1990); Mitsudomi et al., *Cancer Res.* 51:4999-5002 (1991)); gastrin, including gastrin peptide G17 (U.S. patent application. Ser. No. 10/104,607, published as application no. 20030091574; Breff et al., *J Clin Oncol.* 20:4225-31 (20020; CCK-B/gastrin receptor (Id.); antigenic components of Viulizin® (Liu et al., *Int. J. Oncol.* 16:1015-20 (2000); Ferdinandi et al., *Exp. Opin. Invest. Drugs* 8:1721-35 (1999), U.S. Published Application No. 20010009680; Anticancer Drugs. 2003 April; 14(4):289-94; Cancer Chemotherapy and Pharmacology, Volume 51, Issue 3, pages 247-255, 2003); HER2/neu (U.S. Pat. No. 5,550,214); HER2 receptor (U.S. Pat. No. 5,772,997); mammoglobulin (U.S. Pat. No. 5,922,836; Aihara et al., *Cancer Letters* 150: 79-84 (2000)); interferon alpha; TNF alpha; LMP-9 immunotoxin (Bigner et al., Clin Cancer Res. 1995 December; 1(12):1545-55); CAA-P (http://www.scrippslabs.com/biochemicals.html#cancer); PANC1A and PANC1B (U.S. Pat. Nos. 5,998,165 and 5,840,870); and polypeptides expressed by any of the pancreatic cancer genes described in the following U.S. patents and published applications: U.S. Published Application No. 20010016651; U.S. Pat. No. 6,262,249; U.S. Published Application No. 20020111308; U.S. Published Application No. 20020082207; U.S. Published Application No. 20020076721; U.S. Published Application No. 20030091574; U.S. Published Application No. 20030073144; 20020137911. One selects portions thereof that will result in MHC-1 or 2 reactions. The intent is to stimulate both a CD4+ T cell response and a CD8+ T cell response.

In one preferred embodiment, the antigens inserted into the poxvirus, including the PTAAs, can be modified to enhance their ability to elicit an immune reaction.

Any poxvirus can be used with the present invention. Attenuated or replication-impaired poxviruses such as avipox, swine pox, and attenuated orthopox are preferred. In one preferred embodiment, the pox vector is an attenuated orthopox such as MVA or NYVAC.

In another embodiment, the recombinant poxvirus encoding the pancreatic-cancer associated antigen(s) also encodes at least one co-stimulatory molecule. Co-stimulatory molecules are known in the art and include B7 and other CD4+ and CD8+ activators. In a preferred embodiment, the co-stimulatory molecule is a combination of nucleic acids encoding B7 (e.g. B7-1), ICAM-1, and LFA-3, also known as TRICOM, which induce activation of both CD4+ and CD8+ T cells. In one preferred embodiment, a nucleic acid encoding OX40L is added to the poxvirus vector in addition to the TRICOM combination.

In one preferred embodiment, both the nucleic acids encoding the selected tumor associated antigen(s) and the co-stimulatory molecule(s) are inserted into the same poxvirus vector. However, a poxvirus vector system comprising multiple poxvirus vectors that are administered at close intervals (e.g., a few days to a week) to each other can still be used.

In such an embodiment, the nucleic acids encoding the tumor antigen(s) and co-stimulatory molecule(s) are inserted into two different poxvirus vectors. The first and second poxvirus vectors can be from different pox genera, allowing consecutive inoculations of the two recombinant vectors without invoking the potential host immune reaction against the viral vector. The first and second recombinant poxvirus vectors can be administered to the individual in need thereof simultaneously or at intervals ranging from hours to days or even weeks. For example, one preferred embodiment of the system uses a prime/boost tailored to the disease state. For example, the prime may be directed to a wide range of pancreatic cancer associated antigens, taking advantage of the ability of the pox genome to accommodate multiple foreign genes. The boost may be directed to antigens specific for the particular stage of the disease. For example, by monitoring disease progression one could tailor a boost to generate a specific immune reaction reflecting the antigen expression for that particular stage of the disease.

In one preferred embodiment, the tumor antigen encoding recombinant poxvirus vector is administered first and the TRICOM or TRICOM and OX40L are administered consequently. In another embodiment the co-stimulatory molecule(s) containing recombinant poxvirus vector is administered before administering the antigen(s) containing poxvirus vector.

In a preferred embodiment, GM-CSF is administered to the patient before the initial antigen administration. GM-CSF may be administered using a viral vector or an isolated protein in a pharmaceutical formulation. Several forms of recombinant GM-CSF drug are available worldwide, including sargramostim, which is sold under the LEUKINE® brand in the United States by Berlex, Inc.

In one preferred embodiment, the pancreatic cancer antigen used is preferably tailored according to the needs of an individual patient by determining what antigens are being expressed at high levels in the patient's cancer cells. The type and present stage of the pancreatic cancer is evaluated using, for example histochemical and/or immunohistochemical methods and/or transcription pattern and/or mutation analysis of the cancer cells.

In one embodiment, the system of the present invention comprises a method of treating pancreatic cancer, comprising expression profiling a tumor cell sample obtained from an individual, administering a recombinant poxvirus vector comprising a first set of tumor antigens and/or co-stimulatory molecules, selected based upon the analysis of the tumor cells/type at the first stage of the treatment, and administering said vectors to the individual. In a further preferred embodiment, the possible remaining tumor cells are expression profiled, to construct a second recombinant poxvirus expressing a second set of tumor-associated antigens and/or co-stimulatory molecules for administration to the individual.

In one preferred embodiment, the invention provides a system of preventing or delaying the onset of pancreatic cancer in an individual with an increased risk of developing pancreatic cancer, for example due to a hereditary mutation predisposing the individual to pancreatic cancer. The system comprises administering to the individual with a predisposition, to pancreatic cancer a recombinant poxvirus vector encoding at least one tumor antigen specific for the predisposing factor and/or one or more co-stimulatory molecules. In a preferred embodiment, the tumor antigen and co-stimulatory molecules are encoded by the same recombinant poxvirus vector. Alternatively, a system comprising two or more poxvirus vectors can be used.

In one embodiment, the present invention provides a kit comprising one or more recombinant poxvirus vectors each encoding at least one co-stimulatory molecule in a pharmaceutically acceptable carrier and one or more recombinant poxvirus vectors encoding at least one pancreatic cancer associated antigen in a pharmaceutically acceptable carrier. The kit further comprises instructions about what combination of the "ready-to-go" recombinant poxviruses is appropriate to treat different types and stages of pancreatic cancer. The kit alternatively also comprises a diagnostic component comprising, for example, a mutation detection DNA chip and/or an expression pattern measuring cDNA chip to enable determination of the type and/or stage of the pancreatic cancer from a biological sample obtained from the individual in need of treatment.

BRIEF DESCRIPTION OF THE DRAWINGS

FIG. 4 shows the rV-CEA(6D)/TRICOM vector schematic. rV-CEA(6D)/TRICOM was constructed via homologous recombination in vivo between the parental vaccinia DNA and a plasmid vector, pT8016 (see FIG. 3), that contains the CEA(6D), LFA-3, ICAM-1, and B7.1 genes. The plasmid vector also carries the E. coli lacZ gene, which was simultaneously inserted into the recombinant genome with the CEA (6D), LFA-3, ICAM-1, and B7.1 genes. A chromogenic assay for β-galactosidase, encoded by the lacZ gene, was used to select the final vaccine candidate, which was verified by genomic and protein expression analysis.

FIG. 6 shows the rF-CEA(6D)/TRICOM vector schematic. rF-CEA(6D)/TRICOM was constructed via homologous recombination in vivo between the parental fowlpox DNA and a plasmid vector that contains the CEA(6D), LFA-3, ICAM-1 and B7.1 genes. The plasmid vector also carries the E. coli lacZ gene, which was simultaneously inserted into the recombinant genome with the CEA(6D), LFA-3, ICAM-1, and B7.1 genes. A chromogenic assay for β-galactosidase, encoded by the lacZ gene, was used to select the final vaccine candidate, which was verified by genomic and protein expression analysis.

FIG. 7 shows the nucleotide sequence of wobbled MUC-1 used in vectors of the present invention, including PANVAC-VF, also known as wMUC-1(6), as SEQ ID NO:1.

FIG. 8 shows the amino acid sequence of wobbled MUC-1 used in vectors of the present invention, including PANVAC-VF, also known as wMUC1(6), as SEQ ID NO:2.

FIG. 9 shows the nucleotide sequence of wobbled CEA used in vectors of the present invention, including PANVAC-VF, also known as wCEA(6D), as SEQ ID NO:3.

FIG. 10 shows the amino acid sequence of wobbled CEA used in the vectors of the present invention, including PAN-VAC-VF, also known as wCEA(6D), as SEQ ID NO: 4.

FIG. 12 shows the PANVAC-V recombinant vector schematic. A derivative of the Wyeth (New York City Board of Health) strain of vaccinia was used as the parental virus for this recombinant vaccine, called TBC-vTRICOM. This parental virus, designated TBC-vTRICOM, contains the LFA-3, ICAM-1, and B7.1 coding sequences inserted in the Hind III F region of the vaccinia genome. Recombination between the plasmid vector and the viral DNA resulted in the formation of a recombinant virus in which the wCEA(6D) gene, under the transcriptional control of the vaccinia 40K promoter, the wMUC-1(6) gene, under the transcriptional control of the sE/L promoter, and the lacZ gene, under the control of the 40K promoter, were inserted into the Hind III J region of the vaccinia virus genome. The inserted *E. coli* lacZ gene was flanked by duplicated pox virus sequences. Intramolecular recombination between these sequences resulted in deletion of the lacZ gene. Recombinant viruses from which the lacZ gene was deleted gave rise to colorless plaques which were selected and plaque-purified. The final purified recombinant pox virus contained only the desired genes encoding the CEA, MUC-1, LFA-3, ICAM-1 and B7.1 proteins and no marker (lacZ) gene.

FIG. 14 shows the derivation of PANVAC-V parental virus, TBC-vTRICOM. This virus was derived from the Wyeth vaccine strain. First, the Wyeth vaccine was plaque purified by Flow Laboratories and then expanded on CV-1 cells, to create TBC-Wy. Next, plasmid pT1068 was inserted using CV-1 cells, to delete F13L (37K), creating TBC-Wy-Delta37. LFA-3, ICAM-1, B7.1 and F13L were then inserted into this virus using plasmid pT5132 on CED cells, creating TBC-vTRICOM.

DETAILED DESCRIPTION

Figure 1:
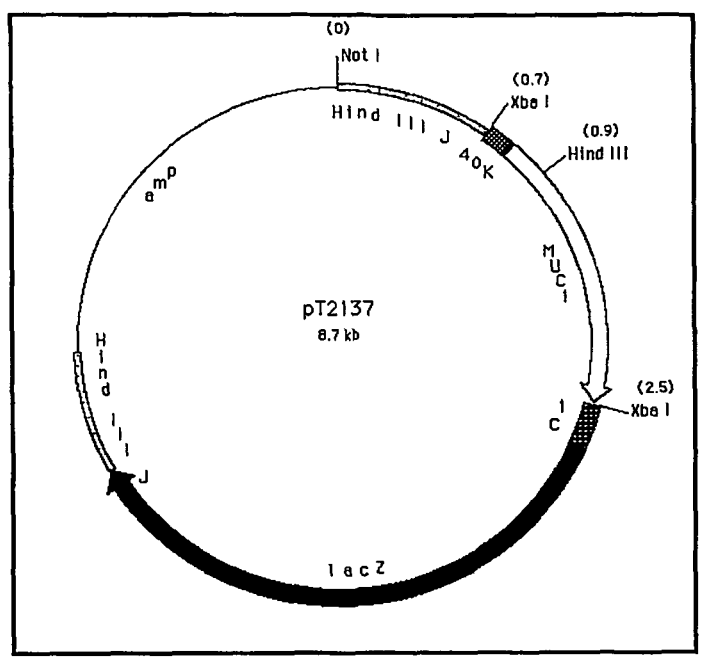
FIG. 1 shows the restriction endonuclease map of plasmid pT2137, which was used for the generation of the rV-MUC-1 recombinant vaccine.

We have now discovered a new method for treating pancreatic cancer in humans involving the use of recombinant poxviruses containing pancreatic tumor associated antigens and immune modulating molecules. Accordingly, the present invention provides a system for screening individuals to identify those at risk of developing or suffering from pancreatic cancer. The system also comprises administering to the individual a first recombinant poxvirus, and at regular intervals thereafter administering a second recombinant poxvirus, wherein the recombinant poxviruses comprise at least one gene encoding a pancreatic tumor associated antigen (PTAA), preferably two PTAAs. Preferred pancreatic tumor associated antigens are CEA and MUC-1, and variants thereof. The genes encoding the PTAAs are preferably inserted into a nonessential region of the poxvirus genome. In one preferred embodiment, both genes are in the same poxvirus vector. In an alternative embodiment, the genes are in multiple vectors. Preferred poxviruses include orthopox, such as vaccinia, and avipox, such as fowlpox and canary pox.

The invention also provides co-administration of granulocyte macrophage-stimulating factor with the recombinant poxviruses, as well as co-administration of immune modulating molecules, such as at least one co-stimulatory molecule, such as LFA-3, ICAM-1, and B7.1. Preferably, one uses the combination of LFA-3, ICAM-1, and B7.1 (TRICOM).

Pancreatic Tumor Associated Antigens

Any pancreatic tumor associated antigen can be used in the present vector system. There are numerous antigens that are associated with pancreatic cancer, which are referred to herein as pancreatic tumor associated antigens, or PTAAs. Particularly preferred PTAAs include CEA and MUC-1, as well as other mucins such as mini-MUC and MUC-4.

In one embodiment, the vector system of the present invention has at least one PTAA. For example, MUC-1 or CEA. Even more preferably, at least two PTAAs. For example, MUC-1 and CEA.

One can use a single pox vector to express CEA, MUC-1, mini-MUC, etc., if desired, or the PTAAs can be expressed on multiple vectors. One can also express multiple copies of certain PTAAS, either in the same vectors or in multiple vectors.

One particularly preferred PTAA is CEA. CEA is an oncofetal glycoprotein that is expressed at high levels on the surface of nearly all tumors of the gastrointestinal tract, including human colorectal, gastric, and pancreatic carcinomas, as well as on many mammary carcinomas and lung adenocarcinomas. Muraro et al., *Cancer Res.* 45:5769-89 (1985). In one embodiment, the CEA is a full-length CEA. A particularly preferred CEA has a modification in one HLA-A2 restricted, immunodominant epitope. This epitope, designated CAP1-6d, or sometimes CEA-6D, binds with enhanced affinity to the receptor and induces CTL in vitro more efficiently than the native epitope. These CTL are capable of lysing human tumor cells that express native CEA. Zaremba et al., *Cancer Res.* 57:4570-7 (1997). Other preferred variants include portions of CEA that elicit a particular MHC class I or II response. In some embodiments, these sequences can be linked together. There are known patterns that elicit particular MHC class I or MHC class II reactions. Additionally, one can introduce changes in the nucleic acid sequence to make the "gene" more stable and less prone to excision during homologous recombination.

One particularly preferred CEA sequence is referred to as wCEA(6D), the nucleotide sequence of which is depicted in FIG. 9 as SEQ ID NO:3.

Another preferred PTAA is a mucin. One particularly preferred mucin is the human polymorphic epithelial mucin, designated MUC-1. The polymorphism of MUC-1 is derived from variation in the number of tandemly repeated amino acid sequences located in the extracellular portion of the glycoprotein. MUC-1 is expressed on the apical surface of normal glandular epithelial cells. Malignant breast and ovarian adenocarcinomas aberrantly glycosylate as well as overexpress MUC-1. The abnormal glycosylation exposes peptide epitopes, making the tumor-derived mucin antigenically distinct from normal mucin. T cell responses against MUC-1 have been identified in patients with breast and ovarian cancer Jerome et al., *Cancer Res.* 51: 2908-16 (1991); Ioannides et al., *J. Immunol.* 151: 3693-3703 (1993).

In one embodiment, the pox vectors of the present invention contain a DNA fragment encoding a MUC-1 fragment, sometimes referred to as mini-MUC. The MUC-1 gene fragment will encode a sufficient portion of MUC-1 to generate an immune reaction to MUC-1, but does not undergo extensive excision as a result of homologous recombination. Preferably, the fragment is approximately 5 to 25 MUC-1 tandem repeat units, more preferably between approximately 6 to 15 MUC-1 tandem repeat units, and most preferably about 6 to 12 MUC-1 tandem repeat units. An especially preferred immunogenic MUC-1 fragment is about 6 MUC-1 tandem repeat units. It is understood that as used herein, the phrase "approximately 6-15 MUC-1 tandem repeats" is intended to include each possible number of repeats within that range, i.e., a fragment with 6 tandem repeats, a fragment with 7 tandem repeats, etc., up to and including a fragment with 15 tandem repeats. Preferred MUC-1 fragments have the human MUC-1 DNA sequence. A preferred MUC-1 DNA sequence is the human MUC-1 cDNA sequence having the repeat units disclosed, e.g., by Gendler et al. (*J. Biol. Chem.* 265:15286-93 (1990)).

Preferably, the PTAA, for example, the mucin repeat sequences, can be altered (sometimes referred to as wobbled) to minimize nucleotide homology without changing the amino acid sequence. For example, the nucleotide sequence of the DNA segment encoding the mucin tandem repeats is altered from the native sequence in such a manner as to reduce duplications of the codons. For example, amino acids typically have two or more codons that will encode the same residue (e.g., glycine is encoded by GGT, GGA, GGG, or GGC). By using other codons encoding the same amino acid, one can further reduce the possibility of undesired recombination events by reducing homology at the nucleic acid level. Additionally, one can also introduce some conservative amino acid changes into different groups of the tandem repeats to further reduce undesired recombination (e.g., glycine/serine, valine/leucine), taking care not to alter a peptide epitope that would reduce its immunogenicity. Nucleotide homology can also be reduced by introducing changes to the amino acid sequence, preferably conservative amino acid substitutions into some of the tandem repeats.

One can also introduce changes in other amino acids to enhance immunogenicity. For example, one particularly preferred MUC-1 sequence is referred to as wMUC-1(6), the sequence of which is depicted in FIG. 7 as SEQ ID NO:1. This variant contains a change which converts a threonine codon to a leucine codon, to create a more immunogenic CTL epitope, and 87 silent nucleotides that were introduced in the repeat region to increase the stability of the MUC-1 gene without changing the amino acid sequence. In addition, a number of nucleotide differences are observed at the beginning and the end of the repeat region between wMUC-1(6) and the MUC-1 Genbank nucleotide sequence (accession no. J05581). This is due to the degeneracy of the repeated sequence at the beginning and end of the repeat region. In contrast, the wMUC-1(6) gene was designed to contain identical repeats with no degeneracy. Other nucleotide differences, consisting of 11 nucleotides in 8 codons, are silent mutations and do not result in amino acid changes.

The list of pancreatic tumor associated antigens continues to increase. Preferred pancreatic cancer associated antigens include CEA, also referred to as carcinoembryonic antigen (Clin. Cancer Res. 6:4176-85, 2000); MUC-1 (Marshall et al., *J. Clin Oncol.* 18:3964-73 (2000)); mini-MUC-1; MUC-4 (U.S. Published Patent Application No. 20020150894); MUC-2; MUC-3; MUC-5AC; MUC-5B; MUC-6; MUC-7; MUC-11; MUC-12; k-ras (U.S. Pat. No. 6,350,445; U.S. Pat. No. 5,985,290); ras peptides, including peptides that correspond to the mutation harbored in an individual's tumor (Chiba et al., *Oncogene* 5:1603-10 (1990); Mitsudomi et al., *Cancer Res.* 51:4999-5002 (1991)); gastrin, including gastrin peptide G17 (U.S. patent application Ser. No. 10/104,607, published as application no. 20030091574; Brett et al., *J Clin Oncol.* 20:4225-31 (2002); CCK-B/gastrin receptor (Id.); antigenic components of Viulizin® (Liu et al., *Int. J. Oncol.* 16:1015-20 (2000); Ferdinandi et al., *Exp. Opin. Invest. Drugs* 8:1721-35 (1999), U.S. Published Application No. 20010009680; Anticancer Drugs. 2003 April; 14(4):289-94; Cancer Chemotherapy and Pharmacology, Volume 51, Issue 3, pages 247-255, 2003); HER2/neu (U.S. Pat. No. 5,550, 214); HER2 receptor (U.S. Pat. No. 5,772,997); mammoglobulin (U.S. Pat. No. 5,922,836; Aihara et al., *Cancer Letters* 150: 79-84 (2000)); interferon alpha; TNF alpha; LMP-9 immunotoxin (Bigner et al., Clin Cancer Res. 1995 December; 1(12): 1545-55); CAA-P (http://www.scrippslabs.com/biochemicals.html#cancer); PANC1A and PANC1B (U.S. Pat. Nos. 5,998,165 and 5,840,870); VEGF; and polypeptides expressed by any of the pancreatic cancer genes described in the following U.S. patents and published applications: U.S. Published Application No. 20010016651; U.S. Pat. No. 6,262,249; U.S. Published Application No. 20020111308; U.S. Published Application No. 20020082207; U.S. Published Application No. 20020076721; U.S. Published Application No.: 20030091574; and U.S. Published Application No. 20030073144; 200201379111.

Co-Stimulatory Molecules

Another particularly preferred embodiment provides co-administration of at least one co-stimulatory molecule, including LFA-3, ICAM-1, and B7.1. Preferably, two co-stimulatory molecules. Even more preferably, three co-stimulatory molecules. It is most preferred that the PTAA(s) is co-administered with LFA-3, ICAM-1, and B7.1 (TRICOM). One can use additional immune modulating molecules such as OX40L. Additionally in alternative embodiments one can administer only one co-stimulatory molecule (e.g. B7, LFA-3, ICAM-1) or combinations thereof such as B7.1 and LFA-3, B7.1 and ICAM-1, and LFA-3 and ICAM-1.

In a preferred embodiment, the poxvirus comprising at least one nucleic acid encoding a pancreatic cancer associated antigen also encodes at least one co-stimulatory or immunostimulatory molecule. Alternatively, the co-stimulatory molecule(s) and the antigen(s) are encoded by a pox vector system comprising multiple recombinant poxvirus vectors.

One preferred group of nucleic acids for insertion into the poxvirus include co-stimulatory molecules, accessory molecules, and/or genes encoding a cytokine. The terms "co-stimulatory" and "immunostimulatory" are used interchangeably in this specification. Examples of co-stimulatory molecules include but are not limited to B7-1, B7-2, ICAM-1, LFA-3, CD72, OX40L (with or without OX40) and the like. Examples of cytokines encompassed by the present invention include but are not limited to IL-2, GM-CSF, TNF-alpha., IFN-gamma., IL-12, RANTES, and the like. Co-stimulatory molecules can be administered using either a recombinant poxvirus vector encoding the co-stimulatory molecules or without the vector as proteins in a pharmaceutically acceptable carrier. For example, OX40 agonists, including OX40L and antibodies against OX40, prevent formation of tolerance by the immune reaction to presented antigens (Weinberg et al. J. Immunol. 164:2160-2169, 2000). Therefore, to increase the immune response against an antigen, the system of the present invention may either deliver a recombinant poxvirus expressing OX40L or antibody against OX40 in a pharmaceutically acceptable carrier before, after or simultaneously with delivering a recombinant poxvirus vector encoding a cancer associated antigen. To enhance the effects of OX40L a nucleic acid encoding OX40 may be added to a poxvirus vector. The nucleic acid sequence of OX40 can be readily obtained from the Entrez Nucleic Acid Database with an accession number AJ277151 and OX40L sequence is readily available form the Entrez Nucleic Acid Database with an accession number: SEG_AB042987S. *Homo sapiens* OX40 . . . [gi:14279071] (http://www.ncbi.nlm.nih.gov/entrez).

One does not have to use a gene encoding an entire co-stimulatory protein or PTAA, but rather only the desired domain. For example, if an immune reaction is desired, only the fragment necessary to stimulate the immune reaction needs to be encoded.

In one preferred embodiment, one administers a poxvirus vector containing B7, LFA-3 and ICAM-1 in conjunction with the tumor associated antigen. In a further preferred embodiment, the poxvirus also encodes OX40L or OX40 intrabody. In another embodiment, the poxvirus encodes OX40L or OX40 intrabody alone. In yet another embodiment, the poxvirus encodes both OX40L or OX40 intrabody and OX40.

Poxviruses expressing B7-1, ICAM-1, and LFA-3, also known as TRICOM, induce activation of both CD4+ and CD8+ T cells. (U.S. Pat. No. 6,045,802; Hodge et al., J. Natl. Cancer Inst. 92: 1228-39 (2000); Hodge et al., Cancer Research 59: 5800-07 (1999)). OX40 is a primary co-stimulator of T cells that have encountered antigen, rather than naïve T cells, and promotes T-cell expansion after T cell tolerance is induced. (Bansal-Pakal et al., Nature Med. 7: 907-12 (2001)). OX40L plays a role during T cell activation by a) sustaining the long-term proliferation of CD4+ and CD8+ T cells, b) enhancing the production of Th1 cytokines such as IL-2, IGN-γ, and TNF-α from both CD4+ and CD8+ T cells without changing IL-4 expression, c) protecting T cells from apoptosis. The combination of B7-1, ICAM-1, LFA-3, and OX40L enhances initial activation and then further potentiates sustained activation of naïve and effector T cells.

Adjuvants

The vaccine formulations of the present invention can include any adjuvant compositions. The co-stimulatory molecules, accessory molecules, and cytokines of the present invention are useful as biologic adjuvants, which can be administered systemically to the host via inserting nucleic acids encoding such into the same or different recombinant poxvirus vectors. Alternatively, the adjuvants can be administered via other, non-vector means.

The adjuvant may be administered using a viral vector or as an isolated protein in a pharmaceutical formulation. In one preferred embodiment, the adjuvant is administered as an isolated protein, such as a recombinant protein.

In one preferred embodiment, the methods of the present invention provide that the adjuvant is administered to the patient at about the same time as the poxvirus vector(s) is administered to the patient. The methods of the invention also provide for administration of the adjuvant for several days either before or after administration of the poxvirus vector. For example, the adjuvant may be administered on each day the patient is administered with a poxvirus vector, and every day thereafter for about 1 to about 5 days. Preferably, for about 3 days.

In another preferred embodiment, the adjuvant is administered to the patient before the initial antigen administration.

Any adjuvant can be used in conjunction with the present vector system. A particularly preferred adjuvant is granulocyte macrophage-stimulating factor (GM-CSF). GM-CSF has been shown to be an effective vaccine adjuvant because it enhances antigen processing and presentation by dendritic cells. Experimental and clinical studies suggest that recombinant GM-CSF can boost host immunity directed at a variety of immunogens. Morrissey, J. Immunol. 139:113-119 (1987); Dranoff, Proc. Natl. Acad. Sci. USA 90:3539-40 (1983); Vieweg, Cancer Res. 54:1760-65 (1994). Another preferred adjuvant is a saponin and/or and immunostimulatory molecule containing an unmethylated CG dinucleotide (U.S. Pat. No. 6,544,518).

One preferred embodiment provides the use of GM-CSF as an adjuvant. GM-CSF may be administered using a viral vector or an isolated protein in a pharmaceutical formulation. In a particularly preferred embodiment, recombinant GM-CSF protein is administered to the patient on each day of vaccination with the poxvirus vector(s), and for each of the following three days (i.e. a total of 4 days). Preferably, 50-500 μg of recombinant GM-CSF is administered per day. Even more preferably, 100 μg. Preferably, the recombinant GM-CSF is administered subcutaneously. Preferably, the recombinant GM-CSF is administered at or near the site of the poxvirus vaccination.

In another embodiment, the gene encoding GM-CSF is inserted into a poxvirus or other vector for delivery of the gene into the host.

Poxvirus Vectors

The poxviruses of the present invention are sometimes referred to herein as a viral vector or a vector system or simply a vector. Poxviruses having utility in the present invention include replicating and non-replicating vectors. Such poxviruses include but are not limited to orthopox such as vaccinia, avipox, e.g. fowl pox and canary pox, raccoon pox, rabbit pox and the like, suipox, e.g. swine pox, capripox, e.g. sheep pox, leporipox, and iridoviruses. Other DNA viruses include iridoviruses and the like.

Parental poxviruses useful in the method of the present invention include but are not limited to orthopoxvirus such as replicating vaccinia virus (Perkus et al Science 229:981-984, 1985; Kaufman et al Int. J. Cancer 48:900-907, 1991, Moss Science 252:1662, 1991), vaccinia Wyeth, and highly attenuated vaccinia viruses such as modified vaccinia Ankara (MVA) (Sutter and Moss, Proc. Nat'l Acad. Sci. U.S.A., 89:10847-10851; Sutter et al Virology 1994) or NYVAC, avipoxviruses such as fowlpoxvirus, canary poxviruses, such as ALVAC and the like (Baxby and Paoletti, Vaccine 10:8-9, 1992; Rinns, M. M. et al (Eds) Recombinant Poxyiruses CRC Press, Inc, Boca Raton 1992—Paoletti, E. Proc. Nat'l Acad. Sci. USA 93:113491-11353; 1996), and suipoxvirus, capripoxvirus and the like.

One preferred vaccinia virus is a Wyeth strain or derivative thereof. Derivatives of the Wyeth strain include but are not limited to derivatives which lack a functional K1L gene, and the like. In yet another embodiment, the virus is Dry-Vax, available as a smallpox vaccine from the Centers for Disease Control, Atlanta, Ga. In another embodiment, the parental poxvirus is a strain of fowlpox, for example POXVAC-TC (Schering-Plough Corporation), and the like.

The poxvirus of the present invention is able to infect, transfect or transduce host cells in a host. The host includes but is not limited to mammals, including humans, birds, fish and the like. The host cells are any cell amenable to infection, transfection or transduction by the poxvirus and capable of expressing the poxvirus, including any foreign genes inserted therein, at functional levels.

The poxvirus of the present invention preferably has a low replicative efficiency in the target cell. This preferably means that no more than about 1 progeny per cell are produced, still more preferably, no more than 0.1 progeny per cell. Replication efficiency can readily be determined empirically by determining the virus titer after infection of the target cell.

As a result of the low replication efficiency and the non-integrative, cytoplasmic nature of the vector, the vector system will not result in sustained replication and infection of other cells. Thus, the pox vector and transformed cells will not adversely affect cells in the host animal at locations distant from where the target cell is.

To further ensure that the poxvirus vector used for a particular host animal is avirulent in that animal, one can readily screen for a viral vector by looking at the virus's host range and tissue specificity. For example, one method is looking at a virus natural host range. Preferably, the virus vector selected is from a virus whose primary range of infection is for a different host animal than the animal that the gene delivery system is to be used in. For example, swinepox can be used as a viral vector when the host is a primate such as a human. However, for veterinary purposes where the host is a pig it would not be preferable. Certain highly attenuated or modified strains such as modified orthopoxvirus (e.g., the MVA or NYVAC strain of vaccinia or strains genetically modified or selected to be non-virulent in their normal host range or in a desired host cell) that are not virulent in their normal host range can, however, be used. Tissue specificity also can be used to preliminarily screen for infectivity and replication efficiency.

Where the host is human, preferred vectors include pox vectors, for example, suipox, such as swinepox, avipox such as fowlpox, canary pox, or pigeon pox, and capripoxvirus. In addition, iridoviruses such as frog virus, and African swine fever virus are also preferred. Preferred viral vectors for use with human cells are non-lytic, avirulent poxviruses such as avipox (Taylor, et al., Vaccine, 6:497-503 (1985) and Jenkins, et al., AIDS Research And Human Retroviruses 7:991-998 (1991)) and suipox (Feller, et al., Virology 183:578-585 (1991)).

According to the present invention, any nucleic acid encoding a pancreatic cancer associated antigen and/or immunostimulatory molecule can be inserted into the poxvirus vector. Because poxviruses have a large genome, they can readily be used to deliver a wide range of genetic material including multiple genes (i.e., act as a multivalent vector). The sizes of the poxvirus genomes ranges between about 130-300 kbp with up to 300 genes, depending on the strain of the virus. Therefore, it is possible to insert large fragments of foreign DNA into these viruses and yet maintain stability of the viral genome. The size of the poxvirus genome allows construction of the custom-designed "rainbow" vectors encoding individualized antigen/immunostimulatory molecule combinations to provide custom-designed treatment to individuals with different types or stages of pancreatic cancer.

In one embodiment, at least one nucleic acid fragment encoding a molecule which has therapeutic value in treating pancreatic cancer is inserted into a poxvirus vector. In another embodiment at least two and up to about ten different nucleic acids encoding different molecules are inserted into the poxvirus vector.

Therefore, the recombinant poxvirus vectors useful according to the present invention encodes one or more pancreatic cancer associated antigens and, preferably, also one or more co-stimulatory molecules can be assessed or treated by methods described in the present application. For example, the gene encoding a antigen associated with pancreatic cancer is incorporated into the recombinant poxvirus genome or portion thereof along with a gene encoding one or more immunostimulatory molecules. Alternatively, the gene encoding an antigen associated with pancreatic cancer and the gene encoding one or more immunostimulatory molecules are incorporated into separate recombinant poxviruses. The antigen associated with pancreatic cancer may be expressed on the surface of a cancer cell or may be an internal antigen. In one embodiment the antigen associated with the pancreatic cancer is a tumor associated antigen (TAA) or portion thereof.

One does not have to use a gene or nucleic acid encoding an entire protein, but rather only the domain desired, for the genes encoding the PTAAs, co-stimulatory molecules, accessory molecules, and cytokines of the present invention. For example, if an immune reaction is desired, only the fragment necessary to stimulate the immune reaction needs to be encoded.

Prime—Boost Protocols

The present invention employs a prime-boost regimen, in which a patient receives an initial "prime" with a composition containing one or more poxvirus vector(s), followed by one or preferably multiple "boosts" with a composition containing one or more poxvirus vector(s).

In one example of a prime, a single poxvirus vector is used for delivery of the PTAAs and co-stimulatory molecules. In another embodiment, two or more poxvirus vectors comprise the priming vaccination, which are administered simultaneously in a single injection. For example, simultaneously administering to a host an admix of two poxvirus vectors, at least one of which is replication competent. If both vectors are replication defective, then not as many cells will get transduced by both viruses. One example of an admix strategy is to use a first vector comprising a DNA encoding at least one pancreatic cancer associated antigen and a second vector comprising a DNA encoding at least one, preferably three, co-stimulatory molecules such as TRICOM.

The boosting vaccinations may also comprise one or more poxvirus vectors. In one preferred embodiment, a single poxvirus vector is used for delivery of the PTAAs and co-stimulator molecules of the boosting vaccination. In another embodiment, two or more poxvirus vectors comprise the boosting vaccination, which are administered simultaneously in a single injection. For example, simultaneously administering to a host an admix of two poxvirus vectors, at least one of which is replication competent. If both vectors are replication defective, then not as many cells will get transduced by both viruses. One example of an admix strategy is to use a first vector comprising a DNA encoding at least one pancreatic cancer associated antigen and a second vector comprising a DNA encoding at least one, preferably three, co-stimulatory molecules such as TRICOM.

For example, the individual can be immunized at least once with a first recombinant poxvirus vector (prime) such as a poxvirus vector carrying the PTAA and preferably at least one immunomodulatory or co-stimulatory molecule. In the preferred embodiment a TRICOM or TRICOM and OX40L or TRICOM and OX40L and OX40 are used. Subsequent immunizations are considered part of the boosting protocol. Preferably, the boosts are performed with a second recombinant poxvirus vector using a different type of poxvirus encoding the antigen(s), and preferably also the co-stimulatory molecule(s). The inoculations are typically given at least one month apart. Other variations can be included in the protocol including use of DNA encoding the PTAA or immunogenic portion thereof, direct administration of the PTAA or immunogenic portion thereof, or other vectors containing such molecules. Such a protocol can have the peptide administered as a boost.

Preferably, one uses a replication impaired or non-replicating vector for either the prime or the boost. In one preferred combination, the prime is an orthopox, e.g. vaccinia, preferably a vaccinia such as the Wyeth vaccine strain. The boost is preferably an avipox vector such as fowlpox or a canary pox such as ALVAC.

In humans, vaccinia vectors including attenuated vaccine vectors such as MVA and NYVAC can be administered several times. Other poxviruses, such as avipox, do not elicit a neutralizing antibody response in humans, and thus can be administered repeatedly without any adverse effect. In planning a protocol one must take this into account. Typically, with these types of cancers repeated administration is necessary. Thus, one should determine if the subject has previously been exposed to vaccinia (as in a smallpox vaccine), and factor that in.

One protocol could be one prime with a vaccinia, such as Wyeth or MVA, encoding a PTAA(s) and at least one co-stimulating molecule, followed by at least 6 boosts with an avipox such as fowlpox encoding a PTAA(s) and preferably at least one co-stimulatory molecule.

Alternatively, immunostimulatory molecules can be administered in a pharmaceutically acceptable carrier without poxvirus vector. For example, an antibody against OX40 can be administered to an individual before, after or simultaneously with inoculation with a recombinant poxvirus encoding a cancer associated antigen.

In one preferred embodiment, the system of the present invention comprises administering to a host a recombinant poxvirus comprising a DNA encoding at least one pancreatic cancer-related antigen and at least one co-stimulatory molecule.

In one particularly preferred embodiment, described further below as Example 11, the priming vector is vaccinia Wyeth carrying the genes for wMUC-1(6), wCEA(6D), LFA-3, ICAM-1, and B7.1, and the boosting vector is fowlpox carrying the genes for wMUC-1(6), wCEA(6D), LFA-3, ICAM-1, and B7.1.

In another embodiment, the present invention provides a system comprising simultaneously administering to a host an admix of two poxvirus vectors, one of which is replication competent. If both vectors are replication defective, then not as many cells will get transduced by both viruses. One example of an admix strategy is to use a first vector comprising a DNA encoding at least one pancreatic cancer associated antigen and a second vector comprising a DNA encoding at least one co-stimulatory molecule. In a preferred embodiment, the two different DNAs are inserted into poxvirus vectors from different genera. For example, the DNA encoding the pancreatic cancer associated antigen(s) is inserted into a suipox derived vector and the co-stimulatory molecule(s) encoding DNA is inserted into to an avipox derived vector.

The schedule for administering the priming poxviruses and the boosting viruses typically includes repeated administration over regular intervals. The boosting vector can be administered every 2-4 weeks thereafter, for example for a total of at least 5-15 boosting vaccinations. As used herein, the number of boosts includes all variants within the range of 5-15 boosts, including at least 5, at least 6, at least 7 times, etc. In one preferred embodiment, the subject receives one vaccination with the priming vector, followed every 2 weeks thereafter with the boosting vector for 6 boosts, followed by every boosts 4 weeks thereafter and continuing depending upon disease progression.

The system of the present invention is particularly useful to generate cell-mediated immune reactions against cancer cells. Accordingly, the present invention further provides a kit that has at least a first recombinant poxvirus which has incorporated into its genome or portion thereof a gene encoding a pancreatic cancer cell-specific antigen in a pharmaceutically acceptable carrier. The first recombinant poxvirus may also comprise one or more genes encoding one or more immunostimulatory or co-stimulatory molecules. Another embodiment provides a kit that has, in addition to the first recombinant poxvirus, a second recombinant poxvirus that comprises one or more genes encoding one or more immunostimulatory molecules in a pharmaceutically acceptable carrier. The kit further provides containers, injection needles and instructions on how to use the kit. Additionally, the kit can also comprise a diagnostic component including mutation detection systems and/or expression profiling systems. In another embodiment, the kit further provides an adjuvant such as GM-CSF, and/or instructions for use of a commercially available adjuvant with the purchased kit components.

A host cell infected with both recombinant viruses expresses both the pancreatic cancer antigen(s) and the immunostimulatory molecule(s). The antigen may be expressed at the cell surface of the infected host cell. The immunostimulatory molecule may be expressed at the cell surface or may be actively secreted by the host cell. The expression of both the antigen and the immunostimulatory molecule provides the necessary MHC restricted peptide to specific T cells and the appropriate signal to the T cell to aid in antigen recognition and proliferation or clonal expansion of antigen specific T cells. The overall result is an upregulation of the immune system. In a preferred embodiment the upregulation of the immune response is an increase in antigen specific T-helper lymphocytes and/or cytotoxic lymphocytes, which are able to kill or inhibit the growth of a pancreatic cancer cell. In the preferred embodiment, the immunostimulatory molecule(s) and the pancreatic cancer antigen(s) are provided in the same poxvirus vector.

Construction of Viral Vectors

The basic techniques of inserting genes into viruses are known to the skilled artisan and involve, for example, recombination between the viral DNA sequences flanking a gene in a donor plasmid and homologous sequences present in the parental virus (Mackett, et al., Proc. Natl. Acad. Sci. USA 79:7415-7419 (1982)). For example, a recombinant virus such as a poxvirus for use in delivering the gene can be constructed in two steps known in the art and analogous to the methods for creating synthetic recombinants of the fowlpox virus described in U.S. Pat. No. 5,093,258, the disclosure of which is incorporated herein by reference. Other techniques include using a unique restriction endonuclease site that is naturally present or artificially inserted in the parental viral vector.

First, the nucleic acid to be inserted into the virus can be placed into a plasmid, e.g., an E. coli plasmid construct, into which DNA homologous to a section of DNA such as that of the poxvirus has been inserted. Separately, the DNA gene sequence to be inserted is ligated to a promoter. The promoter-gene linkage is positioned in the plasmid construct so that the promoter-gene linkage is flanked on both ends by DNA homologous to a DNA sequence flanking a region of pox DNA which is the desired insertion region. The resulting plasmid construct is then amplified by growth within E. coli bacteria and isolated. Preferably, the plasmid also contains an origin of replication such as the E. coli origin of replication, and a marker such as an antibiotic resistance gene for selection and propagation in E. coli.

Second, the isolated plasmid containing the DNA gene sequence to be inserted is transfected into a cell culture, e.g., chick embryo fibroblasts, along with the poxvirus. Recombination between homologous pox DNA in the plasmid and the viral genome respectively results in a poxvirus modified by the presence of the promoter-gene construct in its genome, at a site which does not affect virus viability.

The gene is inserted into a site or region (insertion region) in the virus which does not affect virus viability of the resultant recombinant virus. The skilled artisan can readily identify such regions in a virus by, for example, randomly testing segments of virus DNA for regions that allow recombinant formation without seriously affecting virus viability of the recombinant.

One insertion region that can readily be used and is present in many viruses is the thymidine kinase gene, also referred to herein as the TK gene. For example, it has been found in all poxvirus genomes examined [leporipoxvirus: Upton, et al., J. Virology, 60:920 (1986) (shope fibroma virus); capripoxvirus: Gershon, et al., J. Gen. Virol., 70:525 (1989) (Kenya sheep-1); orthopoxvirus: Weir, et al., J. Virol., 46:530 (1983) (vaccinia); Esposito, et al., Virology, 135:561 (1984) (monkeypox and variola virus); Hruby, et al., PNAS, 80:3411 (1983) (vaccinia); Kilpatrick, et al., Virology, 143:399 (1985) (Yaba monkey tumor virus); avipoxvirus: Binns, et al., J. Gen. Virol. 69:1275 (1988) (fowlpox); Boyle, et al., Virology, 156: 355 (1987) (fowlpox); Schnitzlein, et al., J. Virological Methods, 20:341 (1988) (fowlpox, quailpox); entomopox (Lytvyn, et al., J. Gen. Virol. 73:3235-3240 (1992)].

In fowlpox, in addition to the TK region, other insertion regions include, for example, but are not limited to the following: the BamHI J fragment [Jenkins, et al., AIDS Research and Human Retroviruses 7:991-998 (1991)] the EcoRI-HindIII fragment, BamHI fragment, EcoRV-HindIII fragment, BamHI fragment and the HindIII fragment set forth in EPO Application No. 0 308 220 A1; (Calvert, et al., J. of Virol. 67:3069-3076 (1993); Taylor, et al., Vaccine 6:497-503 (1988); Spehner, et al., (1990) and Boursnell, et al., J. of Gen. Virol. 71:621-628 (1990)). Another preferred poxvirus useful according to the treatment system of the present invention is an avipox, including but not limited to fowlpox, and canary pox, including ALVAC. A particularly preferred avipox virus is fowlpox.

Other particularly preferred fowlpox insertion sites of the present invention are designated the LUS insertion site, the FP14 insertion site, and the 43K insertion site. These sites are also referred to sometimes as FPV006/FPV007 (LUS insertion site), FPV254/FPV255 (LUS insertion site), FPV060/FPV061 (FP14 insertion site), and FPV107/FPV108 (43K insertion site).

In one preferred embodiment, the insertion site in fowlpox is designated the LUS insertion site. In fowlpox, there are two long unique sequences (LUS) at each end of the viral genome (Genbank Accession #AF198100), and thus two LUS insertion sites in each genome. The LUS insertion site at the left end of the genome is between positions 7470-7475 in the fowlpox genomic sequence, and lies 3' of FPV006 and 5' of FPV007 125L. The LUS insertion site at the right end of the genome is between positions 281065 and 281070 in the fowlpox genomic sequence, and lies 5' of FPV254 and 3' of FPV255. In this embodiment, an insert representing a sequence of interest can be inserted at any position within the specified insertion site.

In another preferred embodiment, the insertion site in fowlpox is designated the FP14 insertion site. This site is between positions 67080-67097 in the fowlpox genomic sequence, and lies 5' of FPV060 and 3' of FPV061. In this embodiment, the DNA sequence at the specified insertion site, i.e. between the nucleotides, is deleted in the recombinant virus and replaced with defined inserts representing a sequence of interest.

In yet another preferred embodiment, the novel insertion site in fowlpox is designated the 43K insertion site. This site is at position 128178 of the fowlpox genomic sequence, and lies 5' of FPV107 and 5' of FPV108. These genes are divergently transcribed, and the insertion site lies between the two promoter elements for the two ORFs. In this embodiment, an insert representing a sequence of interest can be inserted at this position within the fowlpox genome.

Particularly preferred fowlpox insertion regions are the FP14 region and the BamHI J region. In one preferred vector, the PTAAs CEA and MUC-1 are inserted into the FP14 region and the co-stimulatory molecules LFA-3, ICAM-1, and B7.1 are inserted into the BamHI J region.

In one preferred embodiment, the insertion site in vaccinia is designated insertion site 44/45. This insertion site was first identified in MVA, where insertion site 44/45 lies between ORFs 044L and 045L, and the insertion site is between positions 37346-37357 in the MVA genomic sequence (Genbank Accession #U94848). This region is 5' of the translational start codon of MVA 044L and 3' of the translational stop codon of MVA 045L. In vaccinia Copenhagen, for insertion site 44/45 the corresponding ORFs are F14L (homologous to MVA 044L) and F15L (MVA 045L), and the insertion site is 5' of the translational start codon of vaccinia F14L and 3' of the translations stop codon of vaccinia F15L. Vaccinia Copenhagen, which contains this region and has its sequence available as Genbank Accession number M35027, is a prototypical vaccinia. Insertion site analogous to sites such as 44/45 can also be used in other vaccinia strains including vaccinia Wyeth, NYVAC (where the insertion site is not known to be modified) and TROYVAC. In this embodiment, the DNA sequence at the specified insertion site, i.e. between the nucleotides, is deleted in the recombinant virus and replaced with defined inserts representing a sequence of interest.

Another insertion site useful according to the present invention is insertion site in vaccinia designated as insertion site 49/50. This insertion site was first identified in MVA, where insertion site 49/50 lies between ORFs 049L and 050L, and the insertion site is between positions 42687-42690 in the MVA genomic sequence (Genbank Accession # U94848). This region is 5' of the translational start codon of MVA 049L and 3' of the translational stop codon of MVA 050L. In vaccinia Copenhagen, for insertion site 49/50 the corresponding ORFs are E2L (homologous to MVA 049L) and E3L (MVA 050L), and the insertion site is 5' of the translational start codon of vaccinia E2L and 3' of the translations stop codon of vaccinia E3L. Vaccinia Copenhagen is a prototypical vaccinia. Similarly, insertion site 49/50 can also be used in other vaccinia strains including NYVAC (where the insertion site is not known to be modified) and TROYVAC. In this embodiment, the DNA sequence at the specified insertion site, i.e. between the nucleotides, is deleted in the recombinant virus and replaced with defined inserts representing a sequence of interest.

In yet another preferred embodiment, the insertion site in vaccinia is designated insertion site 124/125. This insertion site was first identified in MVA, where insertion site 124/125 lies between ORFs 124L and 125L, and the insertion site is between positions 118481-118482 in the MVA genomic sequence (Genbank Accession #U94848). This region is 5' of the translational start codon of MVA 124L and 3' of the translational stop codon of MVA 125L., In vaccinia Copenhagen, for insertion site 124/125 the corresponding ORFs are A13L (homologous to MVA 124L) and A14L (MVA 125L), and the insertion site is 5' of the translational start codon of vaccinia A13L and 3' of the translations stop codon of vaccinia A14L. Similarly, insertion site 124/125 can also be used in other vaccinia strains including NYVAC (where the insertion site is not known to be modified) and TROYVAC. In this embodiment, the DNA sequence at the specified insertion site, i.e. between the nucleotides, is deleted in the recombinant virus and replaced with defined inserts representing a sequence of interest.

In addition to the requirement that the gene be inserted into an insertion site, successful expression of the inserted gene(s) by the modified recombinant poxvirus requires the presence of a promoter operably linked to the desired gene, i.e., in the proper relationship to the inserted gene. The promoter must be placed so that it is located upstream from the gene to be expressed. Promoters are well known in the art and can readily be selected depending on the host and the cell type one wishes to target.

For example in poxviruses, poxviral promoters can be used, including but not limited to the vaccinia 7.5K promoter, the vaccinia 30K promoter, the vaccinia 40K promoter, the vaccinia I3 promoter. Other preferred promoters include the synthetic early/late (sE/L) promoter and the 7.5 promoter. Enhancer elements can also be used in combination to increase the level of expression. Furthermore, the use of inducible promoters, which are also well known in the art, in some embodiments are preferred.

Promoters useful according to the present invention include but are not limited to poxvirus promoters such as an entomopox promoter, an avipox promoter, or an orthopox promoter such as a vaccinia promoter, e.g., HH, 11K or Pi. For example, the Pi promoter, from the Ava I H region of vaccinia, is described in Wachsman et al., J. of Inf. Dis. 155, 1188-1197 (1987). More particularly, this promoter is derived from the Ava I H(Xho I G) fragment of the L-variant WR vaccinia strain, in which the promoter directs transcription from right to left. The map location of the promoter is approximately 1.3 Kbp (kilobase pair) from the 5' end of Ava IH, approximately 12.5 Kbp from the 5' end of the vaccinia genome, and about 8.5 Kbp 5' of the Hind III C/N junction. The Hind III H promoter (also "HH" and "H6" herein) sequence is an up-stream of open reading frame H6 by Rosel et al., J. Virol. 60, 436-449 (1986). The 11K promoter is as described by Wittek, J. Virol. 49, 371-378 (1984) and Bertholet, C. et al., Proc. Natl. Acad. Sci. USA 82, 2096-2100 (1985). One can take advantage of whether the promoter is an early or late promoter to time expression of particular genes. Additionally, as discussed below, one can use inducible promoters.

The present invention also provides a poxvirus vector in which the promoter is modulated by an external factor or cue, allowing control of the level of polypeptide being produced by the vectors by activating that external factor or cue. For example, heat shock proteins are proteins encoded by genes in which the promoter is regulated by temperature. The promoter of the gene which encodes the metal-containing protein metallothionine is responsive to Cd+ ions. Incorporation of this promoter or another promoter influenced by external cues also make it possible to regulate the production of the proteins.

In another preferred embodiment, the poxvirus genome is modified to carry a nucleic acid encoding a pancreatic cancer associated antigen which is operably linked to an "inducible" promoter. Such inducible systems allow careful regulation of gene expression. See, Miller and Whelan, Human Gene Therapy, 8:803-815 (1997). The phrase "inducible promoter" or "inducible system" as used herein includes systems wherein promoter activity can be regulated using an externally delivered agent. Such systems include, for example, systems using the lac repressor from E. coli as a transcription modulator to regulate transcription from lac operator-bearing mammalian cell promoters (Brown et al. Cell, 49:603-612, 1987); systems using the tetracycline repressor (tetR) (Gossen and Bujard, Proc. Natl. Acad. Sci. USA 89: 5547-5551, 1992; Yao et al., Human Gene Ther. 9:1939-1950, 1998; Shokelt et al., Proc. Natl. Acad. Sci. USA 92:6522-6526, 1995). Other such systems include FK506 dimer, VP16 or p65 using castradiol, RU486/mifepristone, diphenol muristerone or rapamycin (see, Miller and Whelan, supra, at FIG. 2). Yet another example is an ecdysone inducible system (see, e.g. Karns et al, MBC Biotechnology 1:11, 2001). Inducible systems are available, e.g., from Invitrogen, Clontech, and Ariad. Systems using a repressor with the operon are preferred. One would adapt these promoters by substituting portions of pox promoters for the mammalian promoter.

In one preferred embodiment of the invention, the promoter may be selectively active in cancer cells; one example of such a promoter is the PEG-3 promoter, as described in International Patent Application No. PCT/US99/07199, Publication No. WO 99/49898 (published in English on Oct. 7, 1999); other non-limiting examples include the prostate specific antigen gene promoter (O'Keefe et al., 2000, Prostate 45:149-157), the kallikrein 2 gene promoter (Xie et al., 2001, Human Gene Ther. 12:549-561), the human alpha-fetoprotein gene promoter (Ido et al., 1995, Cancer Res. 55:3105-3109), the c-erbB-2 gene promoter (Takakuwa et al., 1997, Jpn. J. Cancer Res. 88:166-175), the human carcinoembryonic antigen gene promoter (Lan et al., 1996, Gastroenterol. 111:1241-1251), the gastrin-releasing peptide gene promoter (Inase et al., 2000, Int. J. Cancer 85:716-719), the human telomerase reverse transcriptase gene promoter (Pan and Koenman, 1999, Med. Hypotheses 53:130-135), the hexokinase II gene promoter (Katabi et al., 1999, Human Gene Ther. 10:155-164), the L-plastin gene promoter (Peng et al., 2001, Cancer Res. 61:4405-4413), the neuron-specific enolase gene promoter (Tanaka et al., 2001, Anticancer Res. 21:291-294), the midkine gene promoter (Adachi et al., 2000, Cancer Res. 60:4305-4310), the human mucin gene MUC-1 promoter (Stackhouse et al., 1999, Cancer Gene Ther. 6:209-219), and the human mucin gene MUC-4 promoter (Genbank Accession No. AF241535, published on Jun. 19, 2001 by J. Biol. Chem., "JBC Papers in Press" as Manuscript M104204200).

One embodiment of the present invention provides the use of a regulatory element such as a transcriptional regulatory element or an enhancer.

In one preferred embodiment of the present invention, a "transcriptional regulatory element" or "TRE" is introduced for regulation of the gene of interest. As used herein, a TRE is a polynucleotide sequence, preferably a DNA sequence, that regulates (i.e., controls) transcription of an operably-linked polynucleotide sequence by an RNA polymerase to form RNA. As used herein, a TRE increases transcription of an operably linked polynucleotide sequence in a host cell that allows the TRE to function. The TRE comprises an enhancer element and/or pox promoter element, which may or may not be derived from the same gene. The promoter and enhancer components of a TRE may be in any orientation and/or distance from the coding sequence of interest, and comprise multimers of the foregoing, as long as the desired transcriptional activity is obtained. As discussed herein, a TRE may or may not lack a silencer element. For example, mammary gland specific regulatory element provide a group of TRE useful according to the present invention. An example is human alpha-lactalbumin (ALA) promoter (for specific construct, see, e.g. Anderson et al. Cancer Gene Ther 7:845-852, 2000).

Another preferred embodiment of the present invention provides an "enhance" for regulation of the gene of interest. An enhancer is a term well understood in the art and is a polynucleotide sequence derived from a gene which increases transcription of a gene which is operably-linked to a promoter to an extent which is greater than the transcription activation effected by the promoter itself when operably-linked to the gene, i.e. it increases transcription from the promoter.

Transcriptional activation can be measured in a number of ways known in the art (and described in more detail below), but is generally measured by detection and/or quantization of mRNA or the protein product of the coding sequence under control of (i.e., operatively linked to) the regulatory element. As discussed herein, the regulatory element can be of varying lengths, and of varying sequence composition. By transcriptional activation, it is intended that transcription will be increased above basal levels in the target cell by at least about 2-fold, preferably at least about 5-fold, preferably at least about 10-fold, more preferably at least about 20-fold. More preferably at least about 50-fold, more preferably at least about 100-fold, even more preferably at least about 200-fold, even more preferably at least about 400- to about 500-fold, even more preferably, at least about 1000-fold. Basal levels are generally the level of activity, if any, in a non-target cells, or the level of activity (if any) of a reporter construct lacking the TRE of interest as tested in a target cell type.

In the present invention, the poxvirus vectors directed at specific cancer target cells may also be generated with the use of TREs that are preferentially functional in the target tumor cells. In this embodiment, the poxvirus vector(s) are administered directly at the site of the tumor (i.e. intratumoral injection), and a direct local reaction is desired. Non-limiting examples of tumor cell-specific heterologous TREs, and non-limiting examples of respective potential target pancreatic cancer cells, include TREs from the following genes: mucin-like glycoprotein DF3 (MUC-1), carcinoembryonic antigen (CEA), plasminogen activator urokinase (uPA) and its receptor gene (breast, colon, and liver cancers), and HER-2/neu (c-erbB2/neu).

In the present invention, tumor-specific TREs may be used in conjunction with tissue-specific TREs such as vascular endothelial growth factor receptor. Additional tissue specific TREs are known in the art.

Additional Genes

One preferred group of nucleic acids for insertion into the poxvirus vector useful according to the present invention encode antibodies. Antibodies have long been used in biomedical science as in vitro tools for the identification, purification and functional manipulation of target antigens. Antibodies have been exploited in vivo for both diagnostic and therapeutic applications. In many cases, the specific amino acid and even nucleotide sequences of the relevant portions of the heavy and light chains of monoclonal antibodies are known. For example, a poxvirus encoding at least the CDRs of the monoclonal antibody cancer drugs rituximab, trastuzumab and cetuximab can be produced. A poxvirus may encode full length tetrameric antibodies or single chain antibodies. In one embodiment, recent advances in antibody engineering have now allowed the gene encoding antibodies to be manipulated so that the antigen biding domain can also be expressed intracellularly. These intracellular antibodies are called "intrabodies" (Marasco et al. Gene Therapy, 4:11-15, 1997; U.S. Pat. Nos. 5,965,371; 5,851,829; 6,329,173; and 6,072,036). Preferably the nucleic acids encoding intrabodies encode a single chain humanized antibody. One preferred antibody is an antibody against OX40 as described above (OX40 intrabody).

Custom Vectors

In one embodiment, the system of the present invention allows the treatment to be tailored to the particular individual and disease state. In this embodiment, the PTAA used can be tailored to the individual patient by determining what PTAAs are being expressed at high levels in the patient's cancer cells.

With the development of pharmacogenetics and pharmacogenomics, it is now feasible to obtain detailed information about the type of pancreatic cancer affecting an individual. Accordingly, the type and present stage of the pancreatic cancer can be evaluated using histochemical, immunohistochemical and genetic methods. This data can give additional information about the antigen expression that can be anticipated as the disease progresses. In this way, one can add additional PTAAs that are expected to be expressed as the disease progresses to maximize the immune response.

The pancreatic cancer antigens useful according to the present invention are preferably tailored to the individual patient by determining what antigens are being abnormally expressed or expressed at abnormally high levels in the individual's cancerous or precancerous cells. The antigens useful according to the system of the present invention can also be selected according to the stage of the cancer cells. Generally, pharmacogenetic and pharmacogenomic as well as immunohistochemical data from the individual's cells are used to determine the selection of preferred pancreatic cancer associated antigens in the system of the present invention. In one preferred embodiment, the patient has more than one type of cancer, and the appropriate antigens are selected based upon the specific cancer expressed by the patient.

Custom-designing the pancreatic cancer antigens to fit the needs of an individual patient can be performed using information obtained from, for example, immunohistochemical analysis of a pancreatic tumor biopsy. Alternatively, one can perform a nucleic acid array analysis of the expression profile of the particular pancreatic tumor sample using isolated mRNA from the pancreatic cancer tissue sample.

Other useful nucleic acid arrays suitable to custom-designing the antigens for the methods of the present invention using poxvirus vectors include, for example, a cancer array which allows characterization of expression profiles of genes involved in pancreatic cancers.

Pancreatic Cancer Patients/Subjects for Administration

The pharmaceutical compositions described herein may be used for the treatment of cancer, particularly for the immunotherapy of pancreatic cancer. In the methods of the present invention, one first screens the patient to determine the presence of pancreatic cancer. Preferably, one also screens the patient to determine what stage of pancreatic cancer the patient has.

The pharmaceutical compositions, vaccine formulations, and methods of the present invention can be used to treat an individual with any stage pancreatic cancer, including but not limited to adenocarcinoma of the pancreas, recurrent pancreatic cancer, stage II pancreatic cancer; stage III pancreatic cancer; stage IV pancreatic cancer (a metastatic cancer); stage IVA pancreatic cancer; and stage IVB pancreatic cancer. Preferably, the cancer has been histologically confirmed. In one embodiment, the pancreatic adenocarcinoma is unresectable.

In one preferred embodiment, the poxvirus vectors of the present invention are used to treat patients with stage IIa or stage IIIb pancreatic cancer.

In one preferred embodiment, the poxvirus vectors of the present invention are used to treat patients with metastatic (stage IV) pancreatic cancer.

In one embodiment, the patient having pancreatic cancer has already failed other treatment regimens, for example, chemotherapy.

If the individual has other cancers, one would preferably add additional tumor associated antigens that are associated with those conditions. Within such methods, the pharmaceutical compositions described herein are administered to a patient, typically a warm-blooded animal, preferably a human.

In one embodiment, the pharmaceutical compositions may be used to prevent the development of a cancer, particularly in an individual at higher risk to develop such cancer than other individuals, or to treat a patient afflicted with pancreatic cancer.

Pharmaceutical compositions and vaccines may be administered either prior to or following surgical removal of primary tumors and/or treatment such as administration of radiotherapy or conventional chemotherapeutic drugs. As discussed below, administration of the pharmaceutical compositions may be by any suitable method, including administration by intravenous, intraperitoneal, intramuscular, subcutaneous, intranasal, intradermal, anal, vaginal, topical and oral routes.

The pancreatic cancer treatment system using recombinant poxviruses described herein can be used for any host. Preferably, the host is a mammal. Preferred mammals include primates such as humans and chimpanzees, domestic animals such as horses, cows, pigs, etc. and pets such as dogs and cats. More preferably, the host mammal is a primate or domestic animal. Still more preferably the host mammal is a human.

Administration of Poxvirus Vectors

Introduction of the viral vector carrying the gene to be delivered to the target host cell may be effected by any method known to those of skill in the art.

Administration of the recombinant poxvirus of the invention can be either "prophylactic" or "therapeutic" depending on the subject. When provided prophylactically, the recombinant poxvirus of the present invention is provided in advance of tumor formation to allow the individual's immune system to fight against a tumor that the individual is susceptible of developing. For example, individuals with hereditary cancer susceptibility are a preferred group of patients treated with such prophylactic immunization, another group is one that has been exposed to environmental agents that are linked to such cancer or live in a "hot spot" or pancreatic tumor cluster.

The prophylactic administration of the recombinant poxvirus serves to prevent, ameliorate, or delay pancreatic cancer. When provided therapeutically, the recombinant poxvirus is provided at or after the diagnosis of pancreatic cancer. Thus the present invention may be provided either prior to the anticipated pancreatic cancer or after the initiation of the pancreatic tumor formation.

For administration to a subject, the poxvirus of the present invention is prepared as an inoculum. The inoculum is typically prepared as a solution in a tolerable (acceptable) diluent such as saline, phosphate-buffered saline or other physiologically tolerable diluent and the like to form an aqueous pharmaceutical composition. The formulation can also contain 10% glycerol as a stabilizer or cryoprotectant, as many virus preparations require storage in a frozen state.

The route of inoculation may be scarification, intravenous (I.V.), intramuscular (I.M.), subcutaneous (S.C.), intradermal (I.D.), intraperitoneal (I.P.), intratumor and the like, which results in eliciting a protective response against the disease causing agent. In one preferred embodiment, subcutaneous administration is used. The dose is administered at least once. Subsequent doses may be administered as indicated.

The poxvirus can be administered directly into the tumor, e.g. by intratumoral injection, where a direct local reaction is desired, or the poxvirus can be administered at a site other than the tumor, for example by subcutaneous injection, where. Subcutaneous injection offers convenience and is a particularly preferred administration route.

In providing a mammal with the recombinant poxvirus of the present invention, preferably a human, the dosage of administered recombinant poxvirus will vary depending upon such factors as the mammal's age, weight, height, sex, general medical condition, previous medical history, disease progression, tumor burden and the like.

The term "unit dose" as it pertains to the inoculum refers to physically discrete units suitable as unitary dosages for mammals, each unit containing a predetermined quantity of recombinant poxvirus calculated to produce the desired immunogenic effect in association with the required diluent. The specifications for the novel unit dose of an inoculum of this invention are dictated by, and are dependent upon the unique characteristics of the recombinant virus and the particular immunologic effect to be achieved.

In general, it is desirable to provide the recipient with a dosage of recombinant virus in the range of about $10^5$ to about $10^{10}$ plaque forming units (pfus), although a lower or higher dose may be administered. One preferred dosage is about $2 \times 10^8$ pfus, for example in a volume of about 0.5 ml.

One would inject a sufficient amount of the viral vectors to obtain a serum concentration in the organ of interest of the protein ranging between about 1 pg/ml to 20 µg/ml. More preferably between about 0.1 µg/ml to 10 µg/ml. Still more preferably, between about 0.5 µg/ml to 10 µg/ml.

Examples of methods for administering the recombinant poxvirus into mammals include, but are not limited to, exposure of tumor cells to the recombinant virus ex vivo, or injection of the recombinant poxvirus into the affected host by intravenous, S.C., I.D. or I.M. administration of the virus. Alternatively the recombinant poxvirus or combination of recombinant vectors may be administered locally by direct injection into the cancerous lesion or tumor or topical application in a pharmaceutically acceptable carrier. The quantity of recombinant poxvirus carrying the nucleic acid sequence of one or more antigens in combination with nucleic acid sequences encoding multiple co-stimulatory molecules to be administered is based on the titer of virus particles. A preferred range of the immunogen to be administered is about $10^5$ to $10^{12}$ (e.g., about $10^7$ to $10^{10}$ plaque forming units (pfu) per subject. The equivalence of pfu to virus particles differ according to the specific pfu titration method used, though one pfu usually is equal to about 5 to 100 virus particles. If the mammal to be immunized is already afflicted with cancer or metastatic cancer, the vaccine can be administered in conjunction with other therapeutic treatments such as chemotherapy or radiation.

The schedule for administration of the poxvirus vectors typically involves repeated administration of the boosting vector, as described above. For example, the initial priming vector may be administered 1-3 times, for example every 2-4 weeks for a total of 6-12 weeks. The boosting vector is then administered every 2-4 weeks thereafter, for example for a total of at least 5-15 boosting vaccinations. In one preferred embodiment, the subject receives one vaccination with the priming vector, followed every 2 weeks thereafter with the boosting vector for 6 boosts, followed by every 4 weeks thereafter and continuing depending upon disease progression.

The system of the invention may be used advantageously with other treatment regiments. For example, the system may be used in conjunction with traditional treatment options for pancreatic cancer including surgery, radiation therapy, chemotherapy, acupuncture, and acupressure.

Chemotherapy protocols for the treatment of pancreatic cancer are well known in the art, and can include a range of chemotherapeutic agents. One preferred group of chemotherapeutic agents are capcitabine, irinotecan or 5-fluorouracil.

Other preferred chemotherapeutic agents are docetaxel, gemcitabine

Additional chemotherapeutic agents include the pharmaceutically acceptable taxanes, such as e.g. docetaxel, taxotere, Paclitaxel, 7-Epi-Taxol, 10-Deacetyl Taxol, as well as mixtures thereof, 5-fluorouracil (5-FU), cisplatin, gemcitabine, irinotecan (also called Camposar® or CPT-11), and tamoxifen. 5-FU may be administered with leucovorin. The chemotherapy can comprise doses of 5-FU ranging from 50 to 1000 mg/m.sup.2/d, with leucovorin at 90 mg/d to 100 mg/d or irinotecan ranging from 200-300 mg/m.sup.2/d, gemcitabine ranging from 100-1500 mg/m.sup.2/d; cisplatin (platinol) ranging from 40 mg-100 mg/m.sup.2/d; and tamoxifen from 10 mg-20 mg tablet per day. For example, combinations of chemotherapeutic agents comprise 5-FU Cisplatin, 5-FU-Gemcitabine or 5-FU with leucovorin & cisplatin.

Other examples of anti-cancer drugs that may be used in the various embodiments of the invention, including pharmaceutical compositions and dosage forms and kits of the invention, include, but are not limited to: acivicin; aclarubicin; acodazole hydrochloride; acronine; adozelesin; aldesleukin; altretamine; ambomycin; ametantrone acetate; aminoglutethimide; amsacrine; anastrozole; anthramycin; asparaginase; asperlin; azacitidine; azetepa; azotomycin; batimastat; benzodepa; bicalutamide; bisantrene hydrochloride; bisnafide dimesylate; bizelesin; bleomycin sulfate; brequinar sodium; bropirimine; busulfan; cactinomycin; calusterone; caracemide; carbetimer; carboplatin; carmustine; carubicin hydrochloride; carzelesin; cedefingol; chlorambucil; cirolemycin; cisplatin; cladribine; crisnatol mesylate; cyclophosphamide; cytarabine; dacarbazine; dactinomycin; daunorubicin hydrochloride; decitabine; dexormaplatin; dezaguanine; dezaguanine mesylate; diaziquone; docetaxel; doxorubicin; doxorubicin hydrochloride; droloxifene; droloxifene citrate; dromostanolone propionate; duazomycin; edatrexate; eflornithine hydrochloride; elsamitrucin; enloplatin; enpromate; epipropidine; epirubicin hydrochloride; erbulozole; esorubicin hydrochloride; estramustine; estramustine phosphate sodium; etanidazole; etoposide; etoposide phosphate; etoprine; fadrozole hydrochloride; fazarabine; fenretinide; floxuridine; fludarabine phosphate; fluorouracil; fluorocitabine; fosquidone; fostriecin sodium; gemcitabine; gemcitabine hydrochloride; hydroxyurea; idarubicin hydrochloride; ifosfamide; ilmofosine; interleukin II (including recombinant interleukin II, or rIL2), interferon alfa-2a; interferon alfa-2b; interferon alfa-n1; interferon alfa-3; interferon beta-I a; interferon gamma-I b; iproplatin; irinotecan hydrochloride; lanreotide acetate; letrozole; leuprolide acetate; liarozole hydrochloride; lometrexol sodium; lomustine; losoxantrone hydrochloride; masoprocol; maytansine; mechlorethamine, mechlorethamine oxide hydrochloride rethamine hydrochloride; megestrol acetate; melengestrol acetate; melphalan; menogaril; mercaptopurine; methotrexate; methotrexate sodium; metoprine; meturedepa; mitindomide; mitocarcin; mitocromin; mitogillin; mitomalcin; mitomycin; mitosper; mitotane; mitoxantrone hydrochloride; mycophenolic acid; nocodazole; nogalamycin; ormaplatin; oxisuran; paclitaxel; pegaspargase; peliomycin; pentamustine; peplomycin sulfate; perfosfamide; pipobroman; piposulfan; piroxantrone hydrochloride; plicamycin; plomestane; porfimer sodium; porfiromycin; prednimustine; procarbazine hydrochloride; puromycin; puromycin hydrochloride; pyrazofurin; riboprine; rogletimide; safingol; safingol hydrochloride; semustine; simtrazene; sparfosate sodium; sparsomycin; spirogermanium hydrochloride; spiromustine; spiroplatin; streptonigrin; streptozocin; sulofenur; talisomycin; tecogalan sodium; tegafur; teloxantrone hydrochloride; temoporfin; teniposide; teroxirone; testolactone; thiamiprine; thioguanine; thiotepa; tiazofurin; tirapazamine; toremifene citrate; trestolone acetate; triciribine phosphate; trimetrexate; trimetrexate glucuronate; triptorelin; tubulozole hydrochloride; uracil mustard; uredepa; vapreotide; verteporfin; vinblastine sulfate; vincristine sulfate; vindesine; vindesine sulfate; vinepidine sulfate; vinglycinate sulfate; vinleurosine sulfate; vinorelbine tartrate; vinrosidine sulfate; vinzolidine sulfate; vorozole; zeniplatin; zinostatin; zorubicin hydrochloride, improsulfan, benzodepa, carboquone, triethylenemelamine, triethylenephosphoramide, triethylenethiophosphoramide, trimethylolomelamine, chlomaphazine, novembichin, phenesterine, trofosfamide, estermustine, chlorozotocin, gemzar, nimustine, ranimustine, dacarbazine, mannomustine, mitobronitol, aclacinomycins, actinomycin F(1), azaserine, bleomycin, carubicin, carzinophilin, chromomycin, daunorubicin, daunomycin, 6-diazo-5-oxo-1-norleucine, doxorubicin, olivomycin, plicamycin, porfiromycin, puromycin, tubercidin, zorubicin, denopterin, pteropterin, 6-mercaptopurine, ancitabine, 6-azauridine, carmofur, cytarabine, dideoxyuridine, enocitabine, pulmozyme, aceglatone, aldophosphamide glycoside, bestrabucil, defofamide, demecolcine, elformithine, elliptinium acetate, etoglucid, flutamide, hydroxyurea, lentinan, phenamet, podophyllinic acid, 2-ethylhydrazide, razoxane, spirogermanium, tamoxifen, taxotere, tenuazonic acid, triaziquone, 2,2',2"-trichlorotriethylamine, urethan, vinblastine, vincristine, vindesine and related agents. 20-epi-1,25 dihydroxyvitamin D3; 5-ethynyluracil; abiraterone; aclarubicin; acylfulvene; adecypenol; adozelesin; aldesleukin; ALL-TK antagonists; altretamine; ambamustine; amidox; amifostine; aminolevulinic acid; amrubicin; amsacrine; anagrelide; anastrozole; andrographolide; angiogenesis inhibitors; antagonist D; antagonist G; antarelix; anti-dorsalizing morphogenetic protein-1; antiandrogen, prostatic carcinoma; antiestrogen; antineoplaston; antisense oligonucleotides; aphidicolin glycinate; apoptosis gene modulators; apoptosis regulators; apurinic acid; ara-CDP-DL-PTBA; arginine deaminase; asulacrine; atamestane; atrimustine; axinastatin 1; axinastatin 2; axinastatin 3; azasetron; azatoxin; azatyrosine; baccatin III derivatives; balanol; batimastat; BCR/ABL antagonists; benzochlorins; benzoylstaurosporine; beta lactam derivatives; beta-alethine; betaclamycin B; betulinic acid; bFGF inhibitor; bicalutamide; bisantrene; bisaziridinylspermine; bisnafide; bistratene A; bizelesin; breflate; bropirimine; budotitane; buthionine sulfoximine; calcipotriol; calphostin C; camptothecin derivatives; canarypox IL-2; capecitabine; carboxamide-aminotriazole; carboxyamidotriazole; CaRest M3; CARN 700; cartilage derived inhibitor; carzelesin; casein kinase inhibitors (ICOS); castanospermine; cecropin B; cetrorelix; chlorins; chloroquinoxaline sulfonamide; cicaprost; cis-porphyrin; cladribine; clomifene analogues; clotrimazole; collismycin A; collismycin B; combretastatin A4; combretastatin analogue; conagenin; crambescidin 816; crisnatol; cryptophycin 8; cryptophycin A derivatives; curacin A; cyclopentanthraquinones; cycloplatam; cypemycin; cytarabine ocfosfate; cytolytic factor; cytostatin; dacliximab; decitabine; dehydrodidemnin B; deslorelin; dexamethasone; dexifosfamide; dexrazoxane; dexverapamil; diaziquone; didemnin B; didox; diethylnorspermine; dihydro-5-azacytidine; dihydrotaxol, 9-; dioxamycin; diphenyl spiromustine; docetaxel; docosanol; dolasetron; doxifluridine; droloxifene; dronabinol; duocarmycin SA; ebselen; ecomustine; edelfosine; edrecolomab; eflornithine; elemene; emitefur; epirubicin; epristeride; estramustine analogue; estrogen agonists; estrogen antagonists; etanidazole; etoposide phosphate; exemestane; fadrozole; fazarabine; fenretinide; filgrastim; finasteride; flavopiridol; flezelastine; fluasterone; fludarabine; fluorodaunornmicin hydrochloride; forfenimex; formestane; fostriecin; fotemustine; gadolinium texaphyrin; gallium nitrate; galocitabine; ganirelix; gelatinase inhibitors; gemcitabine; glutathione inhibitors; hepsulfam; heregulin; hexamethylene bisacetamide; hypericin; ibandronic acid; idarubicin; idoxifene; idramantone; ilmofosine; ilomastat; imidazoacridones; imiquimod; immunostimulant peptides; insulin-like growth factor-1 receptor inhibitor; interferon agonists; interferons; interleukins; iobenguane; iododoxorubicin; ipomeanol, 4-; iroplact; irsogladine; isobengazole; isohomohalicondrin B; itasetron; jasplakinolide; kahalalide F; lamellarin-N triacetate; lanreotide; leinamycin; lenograstim; lentinan sulfate; leptolstatin; letrozole; leukemia inhibiting factor; leukocyte alpha interferon; leuprolide+estrogen+progesterone; leuprorelin; levamisole; liarozole; linear polyamine analogue; lipophilic disaccharide peptide; lipophilic platinum compounds; lissoclinamide 7; lobaplatin; lombricine; lometrexol; lonidamine; losoxantrone; lovastatin; loxoribine; lurtotecan; lutetium texaphyrin; lysofylline; lytic peptides; maitansine; mannostatin A; marimastat; masoprocol; maspin; matrilysin inhibitors; matrix metalloproteinase inhibitors; menogaril; merbarone; meterelin; methioninase; metoclopramide; MIF inhibitor; mifepristone; miltefosine; mirimostim; mismatched double stranded RNA; mitoguazone; mitolactol; mitomycin analogues; mitonafide; mitotoxin fibroblast growth factor-saporin; mitoxantrone; mofarotene; molgramostim; monoclonal antibody, human chorionic gonadotrophin; monophosphoryl lipid A+myobacterium cell wall sk; mopidamol; multiple drug resistance gene inhibitor; multiple tumor suppressor 1-based therapy; mustard anticancer agent; mycaperoxide B; mycobacterial cell wall extract; myriaporone; N-acetyldinaline; N-substituted benzamides; nafarelin; nagrestip; naloxone+pentazocine; napavin; naphterpin; nartograstim; nedaplatin; nemorubicin; neridronic acid; neutral endopeptidase; nilutamide; nisamycin; nitric oxide modulators; nitroxide antioxidant; nitrullyn; O6-benzylguanine; octreotide; okicenone; oligonucleotides; onapristone; ondansetron; ondansetron; oracin; oral cytokine inducer; ormaplatin; osaterone; oxaliplatin; oxaunomycin; taxel; taxel analogues; taxel derivatives; palauamine; palmitoylrhizoxin; pamidronic acid; panaxytriol; panomifene; parabactin; pazelliptine; pegaspargase; peldesine; pentosan polysulfate sodium; pentostatin; pentrozole; perflubron; perfosfamide; perillyl alcohol; phenazinomycin; phenylacetate; phosphatase inhibitors; picibanil; pilocarpine hydrochloride; pirarubicin; piritrexim; placetin A; placetin B; plasminogen activator inhibitor; platinum complex; platinum compounds; platinum-triamine complex; porfimer sodium; porfiromycin; prednisone; propyl bis-acridone; prostaglandin J2; proteasome inhibitors; protein A-based immune modulator; protein kinase C inhibitor; protein kinase C inhibitors, microalgal; protein tyrosine phosphatase inhibitors; purine nucleoside phosphorylase inhibitors; purpurins; pyrazoloacridine; pyridoxylated hemoglobin polyoxyethylene conjugate; raf antagonists; raltitrexed; ramosetron; ras farnesyl protein transferase inhibitors; ras inhibitors; ras-GAP inhibitor; retelliptine demethylated; rhenium Re 186 etidronate; rhizoxin; ribozymes; RII retinamide; rogletimide; rohitukine; romurtide; roquinimex; rubiginone B1; ruboxyl; safingol; saintopin; SarCNU; sarcophytol A; sargramostim; Sdi 1 mimetics; semustine; senescence derived inhibitor 1; sense oligonucleotides; signal transduction inhibitors; signal transduction modulators; single chain antigen binding protein; sizofuran; sobuzoxane; sodium borocaptate; sodium phenylacetate; solverol; somatomedin binding protein; sonermin; sparfosic acid; spicamycin D; spiromustine; splenopentin; spongistatin 1; squalamine; stem cell inhibitor; stem-cell division inhibitors; stipiamide; stromelysin inhibitors; sulfinosine; superactive vasoactive intestinal peptide antagonist; suradista; suramin; swainsonine; synthetic glycosaminoglycans; tallimustine; tamoxifen methiodide; tauromustine; tazarotene; tecogalan sodium; tegafur; tellurapyrylium; telomerase inhibitors; temoporfin; temozolomide; teniposide; tetrachlorodecaoxide; tetrazomine; thaliblastine; thiocoraline; thrombopoietin; thrombopoietin mimetic; thymalfasin; thymopoietin receptor agonist; thymotrinan; thyroid stimulating hormone; tin ethyl etiopurpurin; tirapazamine; titanocene bichloride; topsentin; toremifene; totipotent stem cell factor; translation inhibitors; tretinoin; triacetyluridine; triciribine; trimetrexate; triptorelin; tropisetron; turosteride; tyrosine kinase inhibitors; tyrphostins; UBC inhibitors; ubenimex; urogenital sinus-derived growth inhibitory factor; urokinase receptor antagonists; vapreotide; variolin B; vector system, erythrocyte gene therapy; velaresol; veramine; verdins; verteporfin; vinorelbine; vinxaltine; vitaxin; vorozole; zanoterone; zeniplatin; zilascorb; and zinostatin stimalamer. Preferred additional anti-cancer drugs are 5-fluorouracil and leucovorin. Additional cancer therapeutics include monoclonal antibodies such as rituximab, trastuzumab and cetuximab.

The magnitude of a prophylactic or therapeutic dose of each active ingredient in the treatment of a patient with a solid tumor will typically vary with the specific active ingredients, the severity and type of tumor, and the route of administration. The dose and the dose frequency may vary according to age, body weight, response, and the past medical history of the patient; the likelihood of mestastic recurrence must also be considered. Suitable dosing regimens can be readily selected by those skilled in the art with due consideration of such factors by following, for example, dosages reported in the literature and recommended in the Physician's Desk Reference® (54th ed., 2000). Unless otherwise indicated, the magnitude of a prophylactic or therapeutic dose of each pharmaceutical used in an embodiment of the invention will be that which is known to those in the art to be safe and effective, or is regulatory approved.

The present invention also provides a pharmaceutical composition comprising a recombinant poxvirus, including a recombinant poxvirus, and a pharmaceutically acceptable carrier.

In addition to being a treatment system with practically no toxic side effects, the effect of the genetic material delivered using the system of the invention can be easily and carefully monitored and regulated. Preferred poxvirus vectors such as swinepox only express the genetic material for about two weeks. Thus, if effective treatment is provided within that time frame and because the vector system is self limiting, no unnecessary material will be produced after that time period. Where additional dosages are needed, additional administration of the material can be accomplished by repeating the injection. As described above, in certain cases, the addition of a second, third, etc. antigenic or immunostimulatory material can also be added with the subsequent vectors.

The references cited throughout the specification are herein incorporated by reference in their entirety.

EXAMPLES

Example 1 rV-MUC-1 rV-MUC-1 consists of a live recombinant vaccinia virus that expresses the human MUC-1 tumor antigen. MUC-1 is overexpressed in a number of cancers, including breast, ovarian, and pancreatic carcinomas. In addition, abnormal glycosylation of MUC-1 in carcinoma cells makes the tumor-derived MUC-1 antigenically distinct from normal MUC-1.

In summary, the parental virus used for the generation of the rV-MUC-1 vaccine was a plaque isolate from the seed stock of virus used by Wyeth to produce the licensed Dryvax® Smallpox Vaccine. rV-MUC-1 was constructed via homologous recombination in vivo between the parental vaccinia virus DNA and a plasmid vector that contains the MUC-1 gene. The plasmid vector also carries the E. coli lacZ gene, which was simultaneously inserted into the recombinant genome with the MUC-1 gene. A chromogenic assay for β-galactosidase, encoded by the lacZ gene, was used to select the final vaccine candidate, which was verified by genomic and protein expression analysis. The recombinant virus was then used to generate a master virus stock, which was characterized by genomic and protein expression analysis and by testing for potency, sterility, mycoplasma, and reverse transcriptase activity. All test results have supported the identity and safety of the recombinant virus for use in vaccine production.

The plasmid vector (pT2137) used for insertion of the MUC-1 gene into the parental vaccinia virus genome by in vivo recombination is illustrated in FIG. 1. This vector contains the following elements: (1) a prokaryotic origin of replication to allow amplification of the vector in a bacterial host; (2) the gene encoding resistance to the antibiotic ampicillin, to permit selection of prokaryotic host cells that contain the plasmid; (3) DNA sequences homologous to the Hind III J region of the vaccinia genome, which direct insertion of foreign sequences into this region via homologous recombination; (4) a chimeric gene comprising the vaccinia 40K transcriptional promoter linked to the MUC-1 gene; (5) a second chimeric gene comprising the fowlpox C1 transcriptional promoter linked to the E. coli lacZ gene.

The plasmid backbone, including the bacterial origin of replication and the ampicillin resistance gene, was derived from the plasmid vector pUC8 by deletion of a 442 base pair (bp) Hae II fragment containing the pUC8 polylinkers and lacZ gene. A linker containing a single Hind III site was inserted in the unique Nde I site in this vector to facilitate additional cloning. The vaccinia Hind III J sequences and the 40K promoter were isolated from genomic DNA prepared from the WR strain (Panicali et al., 1981) of vaccinia virus. Sequences from the Hind III J region, which flank the MUC-1 and lacZ genes, include a 508 bp Dra I-EcoR I fragment upstream of the 40K-MUC-1 sequence and a 633 bp EcoR I-Dra I fragment downstream of the C1-lacZ sequence. The 40K promoter element was isolated as a 161 bp Dra I-FnuD II fragment from the Hind III H region of vaccinia virus (Rosel et al., J. Virol. 60:436-49 (1986)). The C1 promoter element was isolated as a 240 bp Sau3A I fragment from fowlpox virus (Jenkins et al., 1991). The E. coli lacZ gene was isolated as a 3100 bp BamH I fragment from pDP500 (Panicali et al., 1986).

The gene encoding MUC-1 was isolated at the Dana-Farber Cancer Institute from a cDNA library derived from RNA from the human MCF-7 breast carcinoma cell line (Siddiqui et al., Proc. Natl. Acad. Sci. USA 85:2320-23 (1989)). A truncated version of the gene was used, consisting of the signal sequence, six related but not identical tandem repeat sequences, and the 3' unique coding sequence. The gene was contained on a 1831 bp fragment which includes the truncated coding sequence, 6 nucleotides of the 5' untranslated region, and 298 nucleotides of the 3' untranslated region (Gendler et al., J. Biol. Chem. 265:15286-93 (1990)).

The structure of the plasmid transfer vector was verified by restriction endonuclease digestion using Hind III and Xba I. In addition, the products of digestion with these enzymes were subjected to Southern blot analysis using labeled probes corresponding to the MUC-1 gene and to the vaccinia Hind III J sequences. The DNA fragments visualized by these methods were of the predicted sizes, and the presence of the MUC-1 gene was unequivocally demonstrated, thus confirming the predicted structure of the plasmid.

Figure 2:
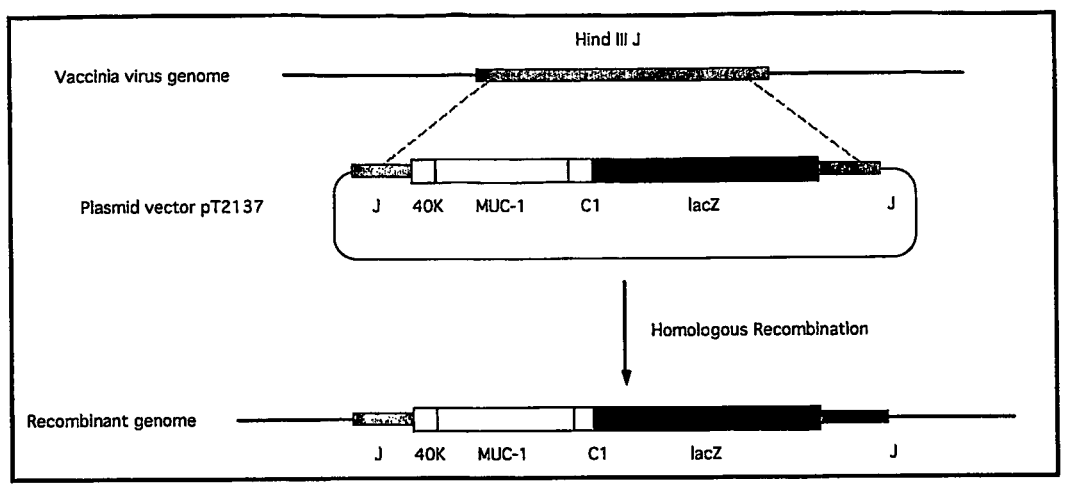
FIG. 2 shows the rV-MUC-1 vector schematic. pT2137 directs insertion of the MUC-1 coding sequence into the TK gene, which is located in the Hind III J region of the vaccinia genome. The MUC-1 gene is under the transcriptional control of the vaccinia 40K promoter. In addition, the E. coli lacZ gene, under the control of the fowlpox virus C1 promoter, is included as a screen for recombinant progeny. A plaque-purified isolate from the Wyeth (New York City Board of Health) strain of vaccinia was used as the parental virus for this recombinant vaccine. In vivo recombination between the plasmid vector and the viral DNA resulted in the formation of a recombinant virus in which the vaccinia TK gene sequence was interrupted by the MUC-1 gene, under the transcriptional direction of the 40K promoter, and the lacZ gene, under the control of the C1 promoter.

A plaque-purified isolate from the Wyeth (New York City Board of Health) strain of vaccinia was used as the parental virus for this recombinant vaccine. In vivo recombination between the plasmid vector and the viral DNA resulted in the formation of a recombinant virus in which the vaccinia TK gene sequence was interrupted by the MUC-1 gene, under the transcriptional direction of the 40K promoter, and the lacZ gene, under the control of the C1 promoter, as illustrated in FIG. 2.

A chromogenic assay for β-galactosidase was used to identify and isolate recombinant viruses containing the lacZ and MUC-1 sequences. This method takes advantage of the ability of vaccinia virus to form distinct plaques when grown on permissive cell monolayers. After in vivo recombination, cells were infected with progeny virus until distinct plaques were visible, at which time the plaques were overlaid with a chromogenic substrate for β-galactosidase (Bluo-Gal™). Viral plaques expressing lacZ appeared blue against a clear background. Positive plaques were picked from the cell monolayer and their progeny were further propagated. Repeated rounds of plaque isolation and replating in the presence of Bluo-Gal resulted in the purification of the desired recombinant, which was then amplified and subjected to genomic and protein expression analysis.

The host cell line used for the preparation of the rV-MUC-1 recombinant virus was the African green monkey kidney cell line CV-1, obtained from the American Type Culture Collection (ATCC #CCL 70). Master and working cell banks (MCB and WCB) were established and characterized according to the Points to Consider recommendations. All data supported the safety of the cell line for use in vaccine production (BB-MF 6587, Volume 1, p. 40-49 and Amendment #2).

rV-MUC-1 was manufactured by infection of primary chicken embryo dermal (CED) cells, obtained from specific pathogen-free chickens, with the recombinant virus. CED cells were seeded into roller bottles and infected with the master virus stock. At the end of the infection period, the cells were harvested and samples were removed for in-process testing. Cells were then lysed by freezing and thawing to release the virus. The cell lysate was clarified by low speed centrifugation and the virus was purified by centrifugation through a 36% sucrose cushion. Purified bulk virus was stored at −70° C. or colder until the titer was determined. The purified bulk virus was then thawed and the concentration adjusted accordingly. The product was delivered aseptically into sterile vials and stored at −70° C. or colder.

In-process and final product testing of rV-MUC-1 were performed according to 21 CFR Part 610 and the Points to Consider recommendations. The crude bulk product was analyzed for the presence of various contaminants, including bacteria and fungi, mycoplasma, *M. tuberculosis*, and adventitious viruses. The in vitro assay for adventitious viruses required specialized treatment (dilution and neutralization) of the test material in order to eliminate interference by the product vaccinia virus. The final container was tested for sterility, identity (genomic and protein expression analysis), potency (virus titration), general safety, appearance, and purity. General safety testing was performed using a 1:10 dilution of the final container material, again to eliminate interference by the product vaccinia virus. Additional product characterization included quantitation of serum and cellular DNA present in the final product, and assessment of vaccine stability.

The preclinical safety testing of rV-MUC-1 comprised assessment of neurovirulence, which was evaluated by a standard intracranial $LD_{50}$ test in weanling mice. Results indicated that the product was less neurovirulent than the licensed Dryvax Smallpox Vaccine, and supported the safety of this vaccine for human administration.

Example 2 rV-CEA(6D)/TRICOM rV-CEA(6D)/TRICOM consists of a live recombinant vaccinia virus that co-expresses a modified form of carcinoembryonic antigen (CEA), leukocyte function associated antigen-3 (LFA-3), intercellular adhesion molecule-1 (ICAM-1), and B7.1. CEA is an oncofetal protein that is overexpressed in human colorectal, gastric, pancreatic, breast, and non-small cell lung carcinomas. LFA-3, ICAM-1, and B7.1 are costimulatory molecules expressed on antigen-presenting cells that are required for the efficient activation of T cells.

In summary, the parental virus used for the generation of this vaccine was a plaque isolate from the seed stock of virus used by Wyeth to produce the licensed Dryvax® Smallpox Vaccine. As shown in FIG. 4, rV-CEA(6D)/TRICOM was constructed via homologous recombination in vivo between the parental vaccinia DNA and a plasmid vector, pT8016 (see FIG. 3), that contains the CEA(6D), LFA-3, ICAM-1, and B7.1 genes. The plasmid vector also carries the *E. coli* lacZ gene, which was simultaneously inserted into the recombinant genome with the CEA(6D), LFA-3, ICAM-1, and B7.1 genes. A chromogenic assay for β-galactosidase, encoded by the lacZ gene, was used to select the final vaccine candidate, which was verified by genomic and protein expression analysis. The recombinant virus was then used to generate a master virus stock, which was characterized by genomic and protein expression analysis and by testing for potency, sterility, mycoplasma, and reverse transcriptase activity. All test results have supported the identity and safety of the recombinant virus for use in vaccine production.

Figure 3:
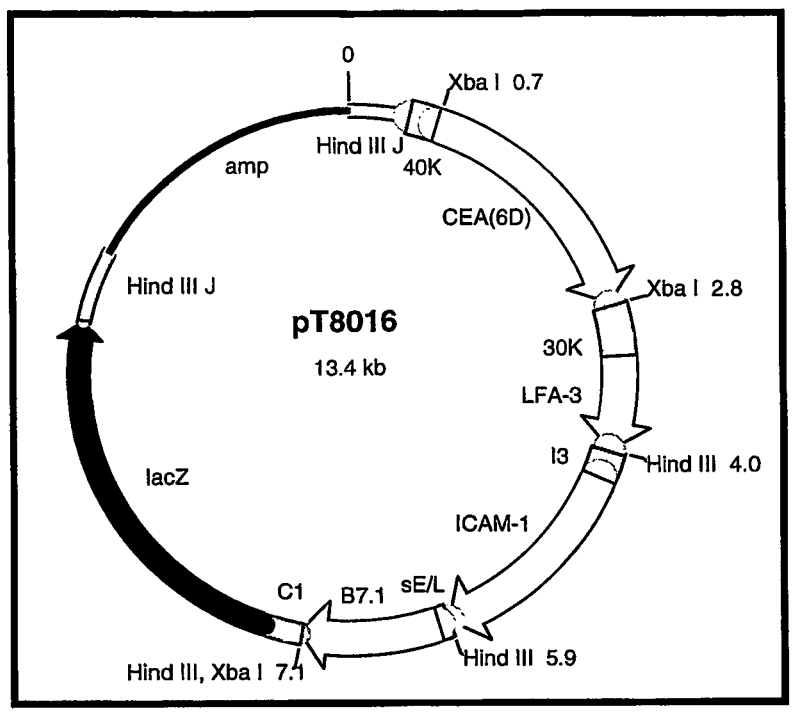
FIG. 3 shows the restriction endonuclease map of plasmid pT8016, which was used for the generation of the rV-CEA (6D)/TRICOM recombinant vaccine.

The plasmid vector (pT8016) used for insertion of the CEA(6D), LFA-3, ICAM-1, and B7.1 genes into the parental vaccinia virus genome by in vivo recombination is illustrated in FIG. 3. This vector contains the following elements: (1) a prokaryotic origin of replication to allow amplification of the vector in a bacterial host; (2) the gene encoding resistance to the antibiotic ampicillin, to permit selection of prokaryotic host cells that contain the plasmid; (3) DNA sequences homologous to the Hind III J region of the vaccinia genome, which direct insertion of foreign sequences into this region via homologous recombination; (4) a chimeric gene comprising the vaccinia 40K transcriptional promoter linked to the CEA(6D) gene; (5) a second chimeric gene comprising the vaccinia 30K transcriptional promoter linked to the LFA-3 gene; (6) a third chimeric gene comprising the vaccinia I3 transcriptional promoter linked to the ICAM-1 gene; (7) a fourth chimeric gene comprising the sE/L transcriptional promoter linked to the B7.1 gene; (8) a fifth chimeric gene comprising the fowlpox C1 transcriptional promoter linked to the *E. coli* lacZ gene.

The plasmid backbone of pT8016, including the bacterial origin of replication and the ampicillin resistance gene, was derived from the plasmid vector pUC8 by deletion of a 442 base pair (bp) Hae II fragment containing the pUC8 polylinkers and lacZ gene. A linker containing a single Hind III site was inserted in the unique Nde I site in this vector to facilitate additional cloning. The vaccinia Hind III J sequences and the vaccinia promoter sequences were isolated from genomic DNA prepared from the vaccinia WR strain (Panicali et al., *J. Virol.* 37:1000-10 (1981)) or from TBC-Wy. Sequences from the Hind III J region, which flank the CEA(6D), LFA-3, ICAM-1, B7.1 and lacZ genes, include a 508 bp Dra I-EcoR I fragment upstream of the 40K-CEA(6D) sequence and a 633 bp EcoR I-Dra I fragment downstream of the C1-lacZ sequence. The 40K promoter element was isolated as a 161 bp Dra I-FnuD II fragment from the Hind III H region[20] of vaccinia virus strain WR. The 30K (M2L) promoter element was isolated as a 415 bp Sal I-Rsa I fragment from the Hind III M region of the vaccinia genome (Goebel et al., *Virology* 179:247-66 (1990)). The I3 promoter element was isolated by polymerase chain reaction (PCR) amplification of a 201 bp sequence immediately 5' to the translation initiation codon of the I3 gene (Schmitt et al., *J. Virol.* 62:1889-97)). The sE/L promoter was isolated as a 60 bp Hind III-Sal I fragment from pJS-8, a derivative of pSC65 (Chakrabarti et al., *BioTechniques* 23:1094-97 (1997)). The C1 promoter element was isolated as a 240 bp Sau3A I fragment from fowlpox virus (Jenkins et al., *AIDS Res. Hum. Retrovir.* 7:991-9 (1991)). The *E. coli* lacZ gene was isolated as a 3100 bp BamH I fragment from pDP500 (Panicali et al., *Gene* 47:193-9 (1986)).

CEA sequences were isolated from a human cDNA clone from a colon carcinoma cell cDNA library constructed at the National Cancer Institute (Kaufman et al., *Int. J. Cancer* 48:900-7 (1991)). The CEA gene was then altered by in vitro mutagenesis to express full-length protein containing one modified epitope. This mutation changed the encoded amino acid at position 609 (where the amino acids are numbered beginning at the first methionine, including the leader sequence) from asparagine to aspartic acid. The modified gene, designated CEA(6D), was designed to enhance the immunogenicity of CEA. The CEA(6D) gene was contained on a 2109 bp fragment which includes the entire coding sequence for CEA and none of the 5' or 3' untranslated region. The gene encoding LFA-3 was isolated at the National Cancer Institute by PCR amplification of Human Spleen Quick-Clone cDNA (Clontech Inc.) using the published sequence (Wallner et al., *J. Exp. Med.* 166:923-32 (1987)). The gene was contained on a 759 bp fragment which includes the entire coding sequence for LFA-3, 2 nucleotides of the 5' untranslated region, and 4 nucleotides of the 3' untranslated region. The gene encoding ICAM-1 was isolated at the National Cancer Institute by PCR amplification of cDNA reverse-transcribed from RNA from an Epstein-Barr Virus-transformed B cell line derived from a healthy male, using the published sequence (Staunton et al., *Cell* 52:925-33 (1988)).

The gene was contained on a 1721 bp fragment which includes the entire coding sequence for ICAM-1, 29 nucleotides of the 5'untranslated region, and 93 nucleotides of the 3'untranslated region. The gene encoding B7.1 was isolated at the National Cancer Institute by PCR amplification of cDNA derived from RNA from the human Raji cell line (ATCC #CCL 86), using the published sequence (Chen et al., *Cell* 71:1093-1102 (1992)). The gene was contained on a 1180 bp fragment which includes the entire coding sequence for B7.1, 22 nucleotides of the 5'untranslated region, and 291 nucleotides of the 3' untranslated-region.

The structure of the plasmid transfer vector was verified by restriction endonuclease digestion. In addition, the products of digestion were subjected to Southern blot analysis using labeled probes corresponding to the CEA(6D), LFA-3, ICAM-1, and B7.1 genes and to the vaccinia Hind III J sequences. The DNA fragments visualized by these methods were of the predicted sizes, and the presence of the CEA(6D), LFA-3, ICAM-1, and B7.1 genes was unequivocally demonstrated, thus confirming the predicted structure of the plasmid.

A plaque-purified isolate from the Wyeth (New York City Board of Health) strain of vaccinia was used as the parental virus for this recombinant vaccine. In vivo recombination between the plasmid vector and the viral DNA resulted in the formation of a recombinant virus in which the thymidine kinase gene was interrupted by the CEA(6D) gene, under the transcriptional control of the vaccinia 40K promoter, the LFA-3 gene, under the transcriptional control of the vaccinia 30K promoter, the ICAM-1 gene, under the transcriptional control of the vaccinia I3 promoter, the B7.1 gene, under the transcriptional control of the sE/L promoter, and the lacZ gene, under the control of the C1 promoter, as illustrated in FIG. 4.

To identify and isolate recombinant viruses containing the lacZ, CEA(6D), LFA-3, ICAM-1, and B7.1 sequences, the chromogenic β-galactosidase method (Bluo-Gal™) described in Example 1, above, was used.

As described in detail above in Example 1, the host cell line used for the preparation of the rV-CEA(6D)/TRICOM recombinant virus was the African green monkey kidney cell line CV-1.

rV-CEA(6D)/TRICOM was manufactured, including in-process and final product safety testing, by infection of primary chicken embryo dermal (CED) cells with the recombinant virus, as described in detail in Example 1.

Example 3 rF-CEA(6D)/TRICOM rF-CEA(6D)/TRICOM consists of a live recombinant fowlpox virus that co-expresses a modified form of carcinoembryonic antigen (CEA), leukocyte function associated antigen-3 (LFA-3), intercellular adhesion molecule-1 (ICAM-1), and B7.1. CEA is an oncofetal protein that is overexpressed in human colorectal, gastric, pancreatic, breast, and non-small cell lung carcinomas. LFA-3, ICAM-1, and B7.1 are costimulatory molecules expressed on antigen-presenting cells that are required for the efficient activation of T cells.

In summary, the parental virus used for the generation of this vaccine was plaque-purified from a tissue culture-adapted vaccine strain of FPV. rF-CEA(6D)/TRICOM was constructed via homologous recombination in vivo between the parental fowlpox DNA and a plasmid vector that contains the CEA(6D), LFA-3, ICAM-1, and B7.1 genes. The plasmid vector also carries the *E. coli* lacZ gene, which was simultaneously inserted into the recombinant genome with the CEA (6D), LFA-3, ICAM-1, and B7.1 genes. A chromogenic assay for β-galactosidase, encoded by the lacZ gene, was used to select the final vaccine candidate, which was verified by genomic and protein expression analysis. The recombinant virus was then used to generate a master virus stock, which was characterized by genomic and protein expression analysis and by testing for potency, sterility, mycoplasma, and reverse transcriptase activity. All test results have supported the identity and safety of the recombinant virus for use in vaccine production.

The generation of recombinant fowlpox viruses is accomplished via homologous recombination in vivo between fowlpox DNA and a plasmid vector that carries the heterologous sequences to be inserted. The plasmid vector contains one or more chimeric genes, each comprising a poxvirus promoter linked to a protein coding sequence, flanked by viral sequences from a non-essential region of the fowlpox virus genome. The plasmid is transfected into cells infected with the parental fowlpox virus, and recombination between fowlpox sequences on the plasmid and the corresponding DNA in the viral genome results in the insertion into the viral genome of the chimeric genes on the plasmid.

Figure 5:
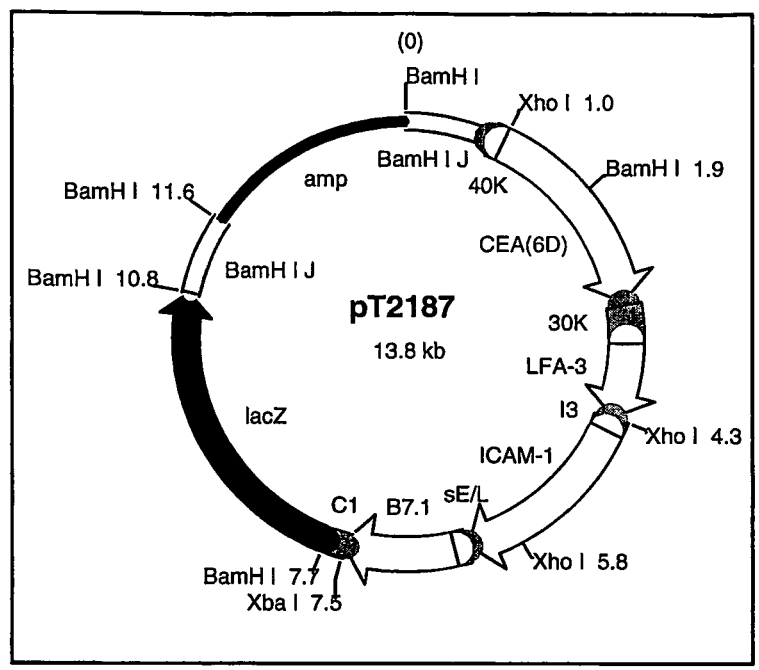
FIG. 5 shows the restriction endonuclease map of plasmid pT2187, which was used for the generation of the rF-CEA (6D)/TRICOM recombinant vaccine.

The plasmid vector (pT2187) used for insertion of the CEA(6D), LFA-3, ICAM-1, and B7.1 genes into the parental fowlpox virus genome by in vivo recombination is illustrated in FIG. 5. This vector contains the following elements: (1) a prokaryotic origin of replication to allow amplification of the vector in a bacterial host; (2) the gene encoding resistance to the antibiotic ampicillin, to permit selection of prokaryotic host cells that contain the plasmid; (3) DNA sequences homologous to the BamH I J region of the fowlpox genome, which direct insertion of foreign sequences into this region via homologous recombination; (4) a chimeric gene comprising the vaccinia 40K transcriptional promoter linked to the CEA(6D) gene; (5) a second chimeric gene comprising the vaccinia 30K transcriptional promoter linked to the LFA-3 gene; (6) a third chimeric gene comprising the vaccinia I3 transcriptional promoter linked to the ICAM-1 gene; (7) a fourth chimeric gene comprising the sE/L transcriptional promoter linked to the B7.1 gene; (8) a fifth chimeric gene comprising the fowlpox C1 transcriptional promoter linked to the *E. coli* lacZ gene.

The plasmid backbone, including the bacterial origin of replication and the ampicillin resistance gene, was derived from the plasmid vector pUC8 by deletion of a 442 base pair (bp) Hae II fragment containing the pUC8 polylinkers and lacZ gene. A linker containing a single BamH I site was inserted in the unique Nde I site in this vector to facilitate additional cloning. The fowlpox BamH I J sequences (Jenkins et al., 1991) were isolated from genomic DNA prepared from the POXVAC-TC vaccine strain (Schering Corporation) of fowlpox virus. Sequences from the BamH I J region that flank the CEA(6D), LFA-3, ICAM-1, B7.1 and lacZ genes include an 850 bp BamH I-Bgl II fragment upstream of the 40K-CEA(6D) sequence and a 750 bp Bgl II-Xba I fragment downstream of the C1-lacZ sequence. The 40K promoter element was isolated as a 161 bp Dra I-FnuD II fragment from the Hind III H region (Rosel et al., 1986) of vaccinia virus strain WR (Panicali et al., 1981). The 30K (M2L) promoter element was isolated as a 415 bp Sal I-Rsa I fragment from the Hind III M region of the vaccinia genome (Goebel et al., 1990). The I3 promoter element was isolated by polymerase chain reaction (PCR) amplification of a 201 bp sequence immediately 5' to the translation initiation codon of the I3 gene (Schmitt et al., *J. Virol.* 62:1889-97 (1988)). The sE/L promoter was isolated as a 60 bp Hind III-Sal I fragment from pJS-8, a derivative of pSC65 (Chakrabarti et al., 1997). The C1 promoter element was isolated as a 240 bp Sau3A I fragment from fowlpox virus (Jenkins et al., 1991). The *E. coli* lacZ gene was isolated as a 3100 bp BamH I fragment from pDP500 (Panicali et al., 1986). CEA sequences were isolated from a human cDNA clone from a colon carcinoma cell cDNA library constructed at the National Cancer Institute (Kaufman et al., 1991). The CEA gene was then altered by in vitro mutagenesis to express full-length protein containing one modified epitope. This mutation changed the encoded amino acid at position 609 from asparagine to aspartic acid (where the amino acids are numbered beginning at the first methionine, including the leader sequence). The modified gene, designated CEA(6D), was designed to enhance the immunogenicity of CEA. The CEA(6D) gene was contained on a 2109 bp fragment which includes the entire coding sequence for CEA and none of the 5' or 3' untranslated region. The gene encoding LFA-3 was isolated at the National Cancer Institute by PCR amplification of Human Spleen Quick-Clone cDNA (Clontech Inc.) using the published sequence (Wallner et al., 1987). The gene was contained on a 759 bp fragment which includes the entire coding sequence for LFA-3, 2 nucleotides of the 5'untranslated region, and 4 nucleotides of the 3'untranslated region. The gene encoding ICAM-1 was isolated at the National Cancer Institute by PCR amplification of cDNA reverse-transcribed from RNA from an Epstein-Barr Virus-transformed B cell line derived from a healthy male, using the published sequence (Staunton et al., 1988). The gene was contained on a 1721 bp fragment which includes the entire coding sequence for ICAM-1, 29 nucleotides of the 5' untranslated region, and 93 nucleotides of the 3'untranslated region. The gene encoding B7.1 was isolated at the National Cancer Institute by PCR amplification of cDNA derived from RNA from the human Raji cell line (ATCC #CCL 86), using the published sequence (Chen et al., 1992). The gene was contained on a 1180 bp fragment which includes the entire coding sequence for B7.1, 22 nucleotides of the 5'untranslated region, and 291 nucleotides of the 3'untranslated region.

The structure of the plasmid transfer vector was verified by restriction endonuclease digestion. In addition, the products of digestion were subjected to Southern blot analysis using labeled probes corresponding to the CEA(6D), LFA-3, ICAM-1, and B7.1 genes and to the fowlpox BamH I J sequences. The DNA fragments visualized by these methods were of the predicted sizes, and the presence of the CEA(6D), LFA-3, ICAM-1, and B7.1 genes was unequivocally demonstrated, thus confirming the predicted structure of the plasmid.

A plaque-purified isolate from the POXVAC-TC vaccine strain of fowlpox virus was used as the parental virus for this recombinant vaccine. In vivo recombination between the plasmid vector and the viral DNA resulted in the formation of a recombinant virus in which the CEA(6D) gene, under the transcriptional control of the vaccinia 40K promoter, the LFA-3 gene, under the transcriptional control of the vaccinia 30K promoter, the ICAM-1 gene, under the transcriptional control of the vaccinia I3 promoter, the B7.1 gene, under the transcriptional control of the sE/L promoter, and the lacZ gene, under the control of the C1 promoter, were inserted into the BamH I J region of the fowlpox virus genome, as illustrated in FIG. 6.

To identify and isolate recombinant viruses containing the lacZ, CEA(6D), LFA-3, ICAM-1, and B7.1 sequences, the chromogenic β-galactosidase method (Bluo-Gal™) described in Example 1, above, was used.

As described in detail above in Example 1, the host cell line used for the preparation of the rF-CEA(6D)/TRICOM recombinant virus was the African green monkey kidney cell line CV-1.

rF-CEA(6D)/TRICOM was manufactured, including in-process and final product safety testing, by infection of primary chicken embryo dermal (CED) cells with the recombinant virus, as described in detail in Example 1.

Example 4

PANVAC™-F

PANVAC-F consists of a live recombinant fowlpox virus that co-expresses a modified (wobbled) form of MUC-1, wMUC-1(6); a modified (wobbled) form of carcinoembryonic antigen, wCEA(6D), leukocyte function associated antigen-3 (LFA-3), intercellular adhesion molecule-1 (ICAM-1), and B7.1. The nucleotide sequence of wobbled MUC-1 used in PANVAC-F, also known as wMUC-1(6), is shown in FIG. 7 as SEQ ID NO:1; the corresponding amino acid sequence of wMUC-1(6) is shown in FIG. 8 as SEQ ID NO:2. The nucleotide sequence of wobbled CEA used in PANVAC-F, also known as wCEA(6D), is shown in FIG. 9 as SEQ ID NO:3; the corresponding amino acid sequence of wCEA(6D) is shown in FIG. 10 as SEQ ID NO:4.

The generation of recombinant fowlpox viruses is accomplished via homologous recombination in vivo between fowlpox DNA and a plasmid vector that carries the heterologous sequences to be inserted. As described above, the plasmid vector contains one or more chimeric genes, each comprising a poxvirus promoter linked to a protein coding sequence, flanked by viral sequences from a non-essential region of the fowlpox virus genome. The plasmid is transfected into cells infected with the parental fowlpox virus, and recombination between fowlpox sequences on the plasmid and the corresponding DNA in the viral genome results in the insertion into the viral genome of the chimeric genes on the plasmid.

For the generation of the PANVAC-F recombinant vaccine, two plasmid vectors were used. The first plasmid, designated pT1154, directs insertion of the wCEA(6D) and wMUC-1(6) coding sequences into the FP14 region of the fowlpox virus genome. The second plasmid, designated pT8150, directs insertion of the LFA-3, ICAM-1, and B7.1 coding sequences (collectively known as TRICOM) into the BamH I J region of the fowlpox virus genome. The wCEA(6D) gene is under the transcriptional control of the vaccinia 40K promoter. The wMUC-1(6) gene is under the transcriptional control of the synthetic early/late (sE/L) promoter. The LFA-3' gene is under the transcriptional control of the vaccinia 30K promoter, the ICAM-1 gene is under the transcriptional control of the vaccinia I3 promoter, and the B7.1 gene is under the transcriptional control of the synthetic early/late (sE/L) promoter. In addition, pT1154 contains the *E. coli* lacZ gene, under the control of the vaccinia 40K promoter, which is included as a screen for recombinant progeny, and pT8150 contains the GUS gene, under the control of the 7.5 promoter, for use in screening for recombinant progeny.

Figure 11:
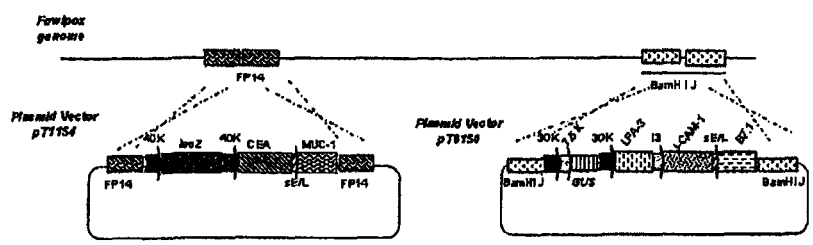
FIG. 11 shows the PANVAC-F recombinant vector schematic. To generate PANVAC-F, two plasmid vectors were used. The first plasmid, designated pT1154, directs insertion of the wCEA(6D) and wMUC-1(6) coding sequences into the FP14 region of the fowlpox virus genome. The second plasmid, designated pT8150, directs insertion of the LFA-3, ICAM-1, and B7.1 coding sequences (collectively known as TRICOM) into the BamH I J region of the fowlpox virus genome. The wCEA(6D) gene is under the transcriptional control of the vaccinia 40K promoter. The wMUC-1(6) gene is under the transcriptional control of the synthetic early/late (sE/L) promoter. The LFA-3 gene is under the transcriptional control of the vaccinia 30K promoter, the ICAM-1 gene is under the transcriptinal control of the vaccinia I3 promoter, and the B7.1 gene is under the transcriptional control of the synthetic early/late (sE/L) promoter. In addition, pT1154 contains the *E. coli* lacZ gene, under the control of the vaccinia 40K promoter, which is included as a screen for recombinant progeny, and pT8150 contains the GUS gene, under the control of the 7.5 promoter, for use in screening for recombinant progeny.

A plaque-purified isolate from the POXVAC-TC vaccine strain of fowlpox virus was used as the parental virus for this recombinant vaccine. In vivo recombination between the plasmid vectors and the viral DNA resulted in the formation of a recombinant virus in which sequences from pT1154 were inserted at FP14, and sequences from pT8150 were inserted at the BamHI J region, as illustrated in FIG. 11.

PANVAC-F has been used in conjunction with PANVAC-V in an ongoing clinical trial for the treatment of patients with metastatic (Stage IV) adenocarcinoma of the pancreas. The results and further description of this trial are described below in Example 11.

Example 5

PANVAC™-V

PANVAC-V consists of a live recombinant vaccinia virus that co-expresses a modified (wobbled) form of MUC-1, wMUC-1(6), a modified (wobbled) form of carcinoembryonic antigen, wCEA(6D), leukocyte function associated antigen-3 (LFA-3), intercellular adhesion molecule-1 (ICAM-1), and B7.1. The nucleotide sequence of wobbled MUC-1 used in PANVAC-V, also known as wMUC-1(6), is shown in FIG. 7 as SEQ ID NO:1. The sequence of wobbled CEA used in PANVAC-V, also known as wCEA(6D), is shown in FIG. 9 as SEQ ID NO:3.

For the generation of the PANVAC-V recombinant vaccine, a newly developed procedure was used that results in the isolation of a recombinant virus that contains the desired foreign genes, but does not contain genes encoding selectable markers. This procedure takes advantage of the genetic instability of duplicated sequences within the poxvirus genome, resulting in the deletion of nucleotide sequences located between the duplicated sequences. Using this procedure, recombinant viruses initially contain the *E. coli* lacZ gene along with the foreign genes of interest. These recombinant viruses are identified and purified using a colorimetric screen for the lacZ gene product. During subsequent propagation of the recombinant viruses, intramolecular recombination between duplicated sequences flanking the lacZ gene results in the deletion of this gene, leaving a recombinant virus that contains only the genes of interest.

Figure 14:
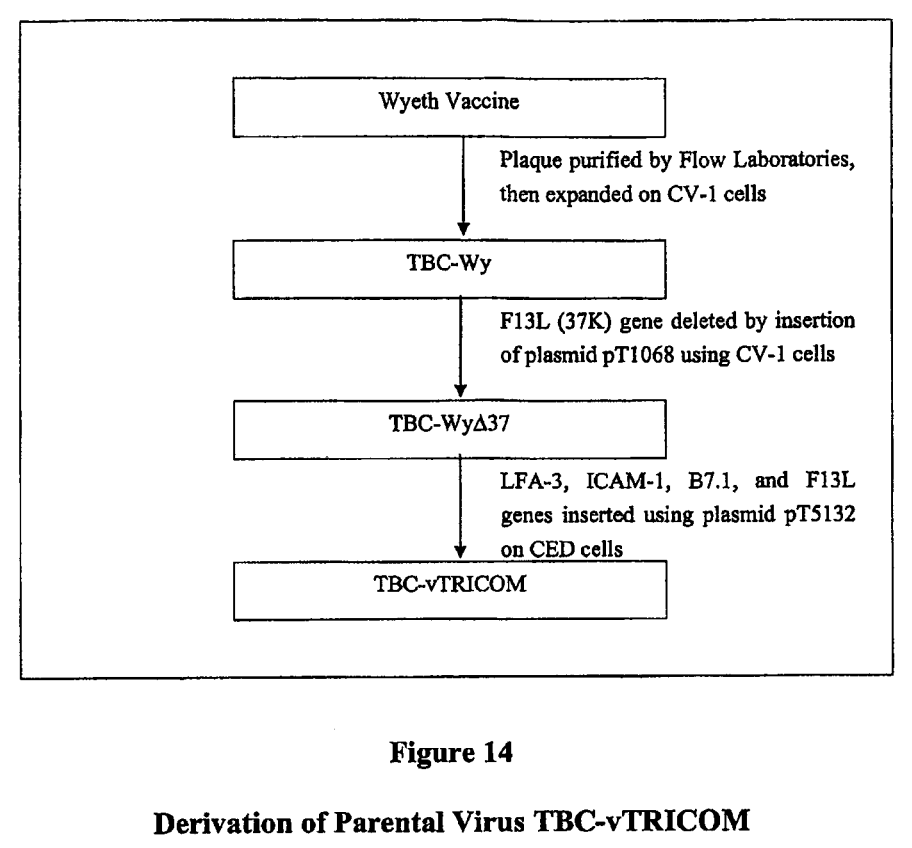

A derivative of the Wyeth (New York City Board of Health) strain of vaccinia was used as the parental virus for this recombinant vaccine, called TBC-vTRICOM. This parental virus, designated TBC-VTRICOM, contains the LFA-3, ICAM-1, and B7.1 coding sequences inserted in the Hind III F region of the vaccinia genome. FIG. 14 shows the derivation of TBC-vTRICOM. First, the Wyeth vaccine was plaque purified by Flow Laboratories and then expanded on CV-1 cells, to create TBC-Wy. Next, plasmid pT1068 was inserted using CV-1 cells, to delete F-13L (37K), creating TBC-Wy-Delta37. LFA-3, ICAM-1, B7.1 and F13L were then inserted into this virus using plasmid pT5132 on CED cells, creating TBC-vTRICOM.

A plasmid vector designated pT1153, that directs insertion of modified CEA and MUC-1 coding sequences into the Hind III J region of the TBC-vTRICOM virus genome, was used to generate the PANVAC-V recombinant vaccine. The modified CEA gene, designated wCEA(6D), is under the transcriptional control of the vaccinia 40K promoter, and the modified MUC-1 gene, designated wMUC-1(6), is under the transcriptional control of the synthetic early/late (sE/L) promoter. The plasmid also contains a portion of the vaccinia Hind III J region that encodes the thymidine kinase (TK) gene. In addition, the *E. coli* lacZ gene, under the control of the vaccinia 40K promoter, is included as a transient screen for recombinant progeny. Recombination between the plasmid vector and the viral DNA resulted in the formation of a recombinant virus in which the wCEA(6D) gene, under the transcriptional control of the vaccinia 40K promoter, the wMUC-1(6) gene, under the transcriptional control of the sE/L promoter, and the lacZ gene, under the control of the 40K promoter, were inserted into the Hind III J region of the vaccinia virus genome, as illustrated in FIG. 12.

The lacZ gene is flanked by repeated sequences for transient lacZ selection. The repeated sequence consists of the entire 161 bp vaccinia 40K promoter, described above.

CEA sequences were isolated from a human cDNA clone from a colon carcinoma cell cDNA library constructed at the National Cancer Institute (Kaufman et al., *Int. J. Cancer* 48:900-7 (1991)). The CEA gene was then altered by in vivo mutagenesis to express full-length protein containing one modified epitope. This mutation changed the encoded amino acid at position 609 from asparagine to aspartic acid (where the amino acids are numbered beginning at the first methionine, including the leader sequence). The modified gene, designated CEA(6D), was designed to enhance the immunogenicity of CEA.

Figure 13:
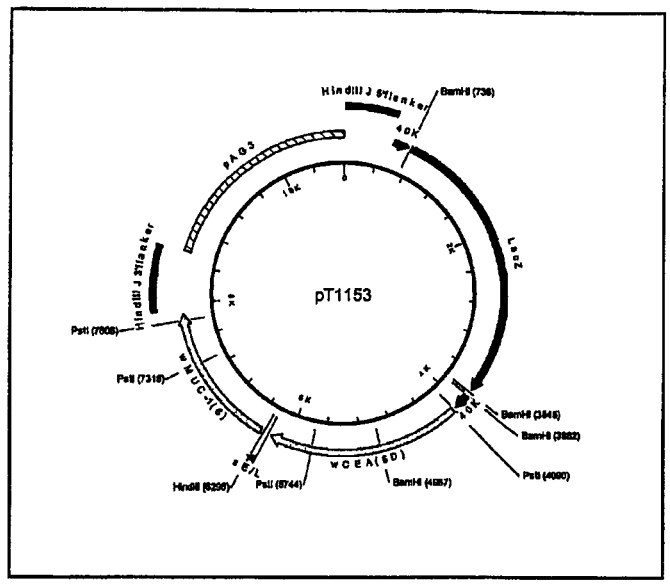
FIG. 13 shows the restriction endonuclease map of plasmid pT1153, which was used for the generation of the PANVAC-V recombinant vaccine. The plasmid vector pT1153 directs insertion of modified CEA and MUC-1 coding sequences into the Hind III J region of the TBC-vTRICOM virus genome. The modified CEA gene, designated wCEA (6D), is under the transcriptional control of the vaccinia 40K promoter, and the modified MUC-1 gene, designated wMUC-1(6), is under the transcriptional control of the synthetic early/late (sE/L) promoter. The plasmid also contains a portion of the vaccinia Hind III J region that encodes the thymidine kinase (TK) gene. In addition, the *E. coli* lacZ gene, under the control of the vaccinia 40K promoter, is included as a transient screen for recombinant progeny.

The plasmid vector (pT1153) used for insertion of the modified CEA and MUC-1 coding sequences into the TBC-vTRICOM parental vaccinia virus genome is illustrated in FIG. 13. This vector contains the following elements: (1) a prokaryotic origin of replication to allow amplification of the vector in a bacterial host; (2) the gene encoding resistance to the antibiotic ampicillin, to permit selection of prokaryotic host cells that contain the plasmid; (3) DNA sequences homologous to the Hind III J region of the vaccinia genome, which direct insertion of foreign sequences into this region via homologous recombination; (4) a chimeric gene comprising the vaccinia 40K transcriptional promoter linked to the lacZ gene; (5) a second chimeric gene comprising the 40K transcriptional promoter linked to the wCEA(6D) gene; (6) a third chimeric gene comprising the sE/L transcriptional promoter linked to the wMUC-1(6) gene.

The plasmid backbone, including the bacterial origin of replication and the ampicillin resistance gene, designated pAG3, was derived from the plasmid vector pUC8 (Vieira, Gene 19:259-268 (1982)) by deletion of a 442 base pair (bp) Hae II fragment containing the pUC8 polylinkers and lacZ gene. A linker containing a single Hind III site was inserted in the unique Nde I site in this vector to facilitate additional cloning. The vaccinia Hind III J sequences and the vaccinia promoter sequences were isolated from genomic DNA prepared from the vaccinia WR strain (Panicali, J. Virol. 37:1000-1010 (1981)) or from TBC-Wy. Sequences from the Hind III J region that flank the lacZ, CEA and MUC-1 genes comprise a 508 bp Dra I-EcoR I fragment upstream of the 40K-lacZ sequence and a 633 bp EcoR I-Dra I fragment downstream of the sE/L-MUC-1 sequence. The 40K promoter element was isolated as a 161 bp Dra I-FnuD II fragment from the vaccinia virus Hind III H region (Rosel, 60:436-449 (1986)). The sE/L promoter was isolated as a 60 bp Hind III-Sal I fragment from pJS-8, a derivative of pSC65 (Chakrabarti, BioTechniques 23:1094-1097 (1997)). The *E. coli* lacZ gene was isolated as a 3100 bp BamH I fragment from pDP500 (Panicali, 47:193-199 (1986)).

The chromogenic assay for β-galactosidase was used to identify and isolate recombinant viruses containing the lacZ, CEA and MUC-1 sequences, as described above in Example 1.

The inserted *E. coli* lacZ gene was flanked by duplicated pox virus sequences. Intramolecular recombination between these sequences resulted in deletion of the lacZ gene. Recombinant viruses from which the lacZ gene was deleted gave rise to colorless plaques which were selected and plaque-purified. The final purified recombinant pox virus contained only the desired genes encoding the CEA, MUC-1, LFA-3, ICAM-1 and B7.1 proteins and no marker (lacZ) gene. Positive recombinants were amplified on CED cells to produce a seed stock.

The seed stock was then subjected to titration, sterility testing, and genomic and protein expression analysis.

Example 6

Pan 1-1

In the Phase I study, patients with unresectable pancreatic cancer were administered an admixture of rV-CEA(6D)/TRICOM™ (see Example 2, above) with rV-MUC-1 (see Example 1, above), followed by rF-CEA(6D)/TRICOM (see Example 3, above), at doses expected to generate relevant immune and clinical responses with minimal toxicity, based on previous studies. Accordingly, the Phase 1 study delivered a 'prime' dose of $1\times10^8$ pfu rV-CEA(6D)/TRICOM™ admixed with $1\times10^8$ pfu rV-MUC-1 subcutaneously (SC), followed 2 weeks later by a 'boost' dose of $1\times10^9$ pfu rF-CEA (6D)/TRICOM™ administered SC. 'Boosts' of $1\times10^9$ pfu rF-CEA(6D)/TRICOM™ administered SC were repeated at two week intervals, for a total of three 'boosts'. Recombinant human sagramostim (100 µg) was given SC at the site of the vaccine injection as an adjuvant, at the time of each immunization and for three consecutive days thereafter. Patients were seen at each vaccination visit and four weeks following the final 'boost' for physical examination and collection of laboratory data and adverse event information.

The results of the Pan1-1 Phase I study are described below in Example 11.

Example 7

Additional Vaccines

Using the procedures set forth in Examples 1-6, a range of vaccine vectors can be generated. Preferred insertion sites in fowlpox and vaccinia vectors, including MVA vectors, are described above. Preferred fowlpox insertion sites are 43K, FP14 and the Long Unique Sequence (LUS). Preferred vaccinia insertion sites are MVA 44/45; MVA 49/50 and MVA 124/125.

For example, the vaccine vector of Example 2 (rV-CEA (6D)/TRICOM) can be modified to exclude the CEA antigen, thus generating rV-TRICOM. This may include murine sequences (i.e. rV-TRICOM-murine) or human sequences (i.e. rV-TRICOM-human). Similarly, in another example, the vaccine vector of Example 3 (rF-CEA(6D)/TRICOM) can be modified to exclude the CEA antigen, thus generating rF-TRICOM, which may be human or murine sequences.

In another example, the vector of Example 4 (PANVAC-F) may be prepared with murine sequences as well as human sequences. The PANVAC antigens, wMUC-1(6), wCEA (6D), LFA-3, ICAM-1, and B7.1 may also be included in an MVA vector at sites MVA 44/45, MVA 49/50, and MVA 124/125.

For example, a recombinant fowlpox virus designated rF-MUC-1 contains the nucleic acid encoding human MUC-1 gene or alternatively one or more repeat regions of the human MUC-1 as described above (SEQ ID NO: 1), under the control of the 40K promoter and has been described (Grosenbach, D. W., Barrientos, J. C., Schlom, J. and Hodge, J. W., *Cancer Res* 61, 4497-505, 2001). The recombinant fowlpox virus containing the nucleic acid encoding human MUC-1 and the murine B7-1, ICAM-1, and LFA-3 genes is designated rF-MUC-1-TRICOM is the same vector than that described by Grosenbach et al. only with MUC-1 antigen instead of CEA antigen (Grosenbach, D. W., Barrientos, J. C., Schlom, J. and Hodge, J. W., *Cancer Res* 61, 4497-505, 2001). The recombinant fowlpox virus designated rF-OX40L was generated by insertion of the murine OX40L gene under the control of the 40K promoter into the genome of rF-CEA at the FP14 site in the genome. The OX40L cDNA was amplified from anti-CD40/anti-IgM-activated murine B cells by RT-PCR using primers specific for the 5'-(dGGTACCGG-TACCATGGAAGGGGAAGGGGTTC) (SEQ ID NO:5) and the 3'-(dCTCGAGCTCGAGTCACAGTGGTACTTG-GTTC) (SEQ ID NO:6) ends of the open reading frame. The cDNA was cloned into a poxvirus transfer vector. Sequence analysis confirmed that no mutations were introduced in the cloning process. The recombinant fowlpox virus designated rF-MUC-1-TRICOM/OX40L was generated by insertion of the murine OX40L gene under the control of the 40K promoter into the genome of rF-TRICOM at the FP14 site in the genome. Both recombinant fowlpox viruses expressing OX40L were generated by methods previously described (Gritz, L., Destree, A., Cormier, N., Day, E., Stallard, V., Caiazzo, T., Mazzara, G. and Panicali, D., *J Virol* 64, 5948-57, 1990). These viruses also express the human MUC-1 gene and the bacterial beta-galactosidase gene.

The recombinant fowlpox virus designated rF-CEA contains the nucleic acids encoding human CEA gene, or any antigenic repeat thereof as shown in SEQ ID NO: 2, under the control of the 40K promoter and has been described (Grosenbach, D. W., Barrientos, J. C., Schlom, J. and Hodge, J. W., *Cancer Res* 61, 4497-505, 2001). The recombinant fowlpox virus containing the human CEA gene and the murine B7-1, ICAM-1, and LFA-3 genes is designated rF-TRICOM throughout this study and has been described (Id.). The recombinant fowlpox virus designated rF-OX40L was generated as describe above. The recombinant fowlpox virus designated rF-CEA-TRICOM/OX40L was generated by insertion of the murine OX40L gene under the control of the 40K promoter into the genome of rF-TRICOM at the FP14 site in the genome. Both recombinant fowlpox viruses expressing OX40L were generated by methods previously described (Gritz, L., Destree, A., Cormier, N., Day, E., Stallard, V., Caiazzo, T., Mazzara, G. and Panicali, D., *J Virol* 64, 5948-57, 1990). These viruses also express the human CEA gene and the bacterial β-galactosidase gene.

Example 8

Immune Response to TAAs Expressed by Recombinant Pox Viruses in a Murine Model

To evaluate immune responses to recombinant pox viruses expressing CEA or MUC-1, mice were immunized with recombinant viruses expressing these antigens alone or in combination with murine homologs of B7.1 or of the three costimulatory molecules that comprise murine TRICOM (muB7.1, muTRICOM™, respectively). The use of murine costimulatory molecules in these studies allowed assessment of the effect of costimulation in the development of T cell responses.

In one experiment, the effect of muB7.1 on immune responses elicited by vaccinia-expressed MUC-1 was evaluated. One group of C57BL/6 mice was vaccinated with an admixture of rV-MUC-1 and non-recombinant vaccinia virus ($10^7$ pfu of each virus) on days 0, 14, and 28. The second group of mice was vaccinated with an admixture of rV-MUC-1 and rV-muB7.1 ($10^7$ pfu of each virus) on day 0, and then with an admixture of rV-MUC-1 and non-recombinant vaccinia virus ($10^7$ pfu of each virus) on days 14 and 28. The mice were euthanized on day 35 and cytotoxic T cell activity was assessed in a standard indium release assay.

MUC-1-specific CTL were detected in both groups; however, the percent specific lysis was approximately 1.5-fold higher in mice that received the rV-MUC-1/rV-muB7.1 admixture. (Akagi et al., *J Immunother.* 20:38-47 (1997))

Another experiment compared the effects of muB7.1 and muTRICOM™ on immune responses elicited by vaccinia-expressed CEA. In this study, C57BL/6 CEA-transgenic mice, which express human CEA with a tissue distribution similar to that of humans, were vaccinated with one of three immunogens: (1) rV-CEA; (2) rV-CEA admixed with rV-muB7.1; or (3) rV-CEA/muTRICOM. Animals were sacrificed on day 22 and CEA-specific lymphoproliferative responses were measured. Mice immunized with rV-CEA/muTRICOM™ had two-fold greater responses than those vaccinated with rV-CEA+rV-muB7.1 and four-fold greater responses than those vaccinated with rV-CEA alone. A number of additional studies evaluated immune responses to pox virus-expressed CEA in mice. (Hodge et al., J. Natl. Cancer Inst. 92: 1228-39 (2000); Hodge et al., Cancer Research 59: 5800-07 (1999)).

Example 9

Anti-Tumor Activity of Vaccines Expressing Costimulatory Molecules in Murine Models Murine models allow not only measurement of immune responses elicited by cancer vaccines, but also evaluation of prophylactic or therapeutic anti-tumor effects stimulated by these vaccines. For example, to evaluate the ability of pox virus-based vaccines to protect against tumor challenge, mice were immunized by tail scarification with an admixture of rV-CEA and rV-muB7.1. When immunized mice were challenged with CEA-expressing MC-38 cells, tumors failed to establish, indicating that immunization had given rise to protection from tumor challenge. This protection was accompanied by corresponding CEA-specific T cell responses (Hodge et al., *Cancer Res* 55:3598-3603 (1995)). Similar results were reported after mice were immunized with a single recombinant vaccinia virus that expressed both CEA and muB7.1 (Kalus, 1999). Subsequently, the admixture (rV-CEA+rV-muB7.1) was compared to the dual gene construct (rV-CEA/muB7.1) in a tumor protection model. Both the admixture and the single recombinant elicited antitumor responses; however, higher doses of the admixed viruses were required to obtain immune responses comparable to those obtained using the single recombinant.

Successful protection using muB7.1 led to studies evaluating combinations of costimulatory molecules. In another tumor challenge experiment, C57BL/6 mice were vaccinated SC with either rV-CEA or rV-CEA/muTRICOM™, then challenged 100 days later with MC-38 colon carcinoma cells that expressed CEA. All mice vaccinated with rV-CEA succumbed to tumors while all mice vaccinated with rV-CEA/muTRICOM™ survived tumor challenge. T cell responses were also significantly higher in animals vaccinated with rV-CEA/muTRICOM (Hodge et al., Cancer Research 59: 5800-07 (1999)).

In the previously described tumor protection studies, CEA, although expressed on a murine tumor cell line, represented a foreign antigen in the vaccinated mice. In order to determine whether similar anti-tumor responses could be elicited in a setting in which CEA represents a "self" antigen, tumor immunotherapy studies were conducted using CEA-transgenic mice. In one experiment, animals were inoculated first with CEA-expressing MC-38 cells, then immunized four days later with rV-CEA, rV-CEA/muB7.1, or rV-CEA/muTRICOM™. Only mice that received the rV-CEA/muTRICOM™ remained tumor-free. These mice also had the highest CEA-specific T cell responses (Hodge et al., Cancer Research 59: 5800-07 (1999)).

In a more rigorous immunotherapy model, CEA-transgenic mice with established CEA-positive hepatic carcinoma metastases were treated by weekly vaccination for four weeks with rV-muCEA/TRICOM™ plus murine GM-CSF and IL-2. Of the sixteen treated mice, nine (56%) remained alive through 25 weeks. By contrast, in the control group (which received non-recombinant vaccinia plus cytokines), only one of nineteen (5%) survived past 16 weeks (Grosenbach, 2001).

Example 10

TRICOM™ Expression in Antigen-Presenting Cells in a Murine Model

Dendritic cells (DCs) are key participants in the activation of both CD4+ and CD8+ T lymphocytes. The degree of T cell activation appears to be related, at least in part, to the level of expression of certain costimulatory molecules on DCs. Murine DCs infected with rV-muTRICOM or rF-muTRICOM™ were shown to significantly enhance naïve T cell, allogenic T cell, and peptide-specific T cell proliferation in vitro. Furthermore, peptide-pulsed DCs infected with rV- or rF-muTRICOM™ induced higher CTL activity in vivo than did the corresponding uninfected peptide-pulsed DCs (Hodge et al., *J Natl Cancer Inst.* 92:1228-1239 (2000)).

Similar results have been obtained using human DCs. The origin and the stage of maturity of human DCs affect the levels of costimulatory molecules exhibited by these cells. Zhu and coworkers have demonstrated that several hours after infection with rF-TRICOM™, human DCs efficiently hyper-express all three costimulatory molecules (Zhu, 2001). In addition, peptide-pulsed autologous DCs infected with rF-muTRICOM™ were more potent in activating T cells in vitro than uninfected peptide-pulsed DCs, as measured by interferon-gamma production after 24 hours of incubation. These results were obtained using peptides from both strong and weak viral antigens as well as peptides from self, tumor-associated antigens (CEA and PSA). Enhanced T cell activation was not accompanied by increased T cell apoptosis.

The potency of other antigen-presenting cells (APCs) such as bone marrow progenitor cells (BMPCs) can also be increased using pox virus vectors expressing TRICOM™ (*Rad*, 2001). Murine BMPCs infected with rV- or rF-muTRICOM™ significantly enhanced the activation of both naïve and effector CD4+ and CD8+ T cell populations. A generic APC population, murine splenocytes, could also be rendered more efficient at antigen presentation by infection with either of the TRICOM™ vectors (Hodge et al., *Vaccine* 19:3552-3567 (2001)). Infected splenocytes required less concanavalin A (acting as signal 1) to activate naïve T cells. Moreover, when a constant amount of concanavalin A was used for the assay, fewer infected splenocytes were required for activation of T cells. TRICOM™-infected splenocytes also induced greater antigen-specific T cell activation than did uninfected splenocytes, approaching levels achieved with uninfected DCs as measured by interferon-gamma production.

Example 11

Clinical Trial Data

PANVAC-VF was designed to stimulate the immune system to target and destroy cancer cells expressing two proteins (or antigens), carcinoembryonic antigen (CEA) and mucin-1 (MUC-1), found on over 90 percent of pancreatic tumor cells. Therion's vaccines were administered via subcutaneous injection in a "prime-boost" fashion, employing vaccinia as the priming vector, followed by sequential doses with a fowlpox vector, as described below. The vaccines also incorporate TRICOM, designed to enhance and sustain a targeted immune response against tumor cells.

Two open-label Phase I clinical studies have been conducted: PAN 1-1 and TBC-PAN-002, each with the primary objective of safety. In summary, the studies enrolled a total of 22 patients with advanced (Stage III or IV) pancreatic cancer, 20 of whom had metastatic disease (Stage IV); all had received prior chemotherapy. Based on a review of multiple Phase III studies involving other chemotherapeutics, the expected median overall survival of this patient population is approximately 3 months.

PAN1-1

PAN1-1 was an open-label study to evaluate the safety and tolerability of rV-CEA(6D)/TRICOM admixed with rV-MUC-1 followed by rF-CEA(6D)/TRICOM in combination with sagramostim in the treatment of patients with adenocarcinoma of the pancreas. The study population included patients ≥18 years of age who had histologically confirmed adenocarcinoma of the pancreas, whose disease was unresectable in the opinion of the investigator, and who had an ECOG performance status of ≤2.

Patients received a priming dose of $1 \times 10^8$ pfu rV-CEA (6D)/TRICOM admixed with $1 \times 10^8$ pfu rV-MUC-1 SC on Day 0, followed by a boosting dose of $1 \times 10^9$ pfu rF-CEA (6D)/TRICOM SC on Days 14, 28, and 42. Sagramostim (100 µg) was given SC at the injection site on the day of each vaccine administration and for three consecutive days thereafter. At the discretion of the Investigator, patients were allowed to continue into an extension treatment phase following Day 70. Three patients entered the extension phase; the study was completed on 11 Dec. 2003 following withdrawal of the final patient.

Safety parameters evaluated during the course of this study included medical history, vital signs, physical examination, laboratory tests (hematology, chemistry, and urinalysis), ECGs, ECOG performance status and documentation of concomitant medications.

Twelve patients enrolled into the study and received the priming vaccination. Two of these twelve patients were replacements for patients who prematurely withdrew from the study for reasons other than toxicity. Nine patients completed the full course of treatment per protocol (one priming and three boosting injections). Five patients completed the final follow-up visit (Day 70: 28 days following the last dose). Thus, of the original planned 40 vaccinations (ten patients; four vaccinations each), 42 vaccinations were administered to the 12 patients enrolled in this study. Three of these patients entered into the extension phase and received monthly vaccinations for an additional five-month period. Thus, for the three patients enrolled in the extension phase, each received a total of nine vaccinations over an approximately seven-month period (Core Phase plus Extension Phase).

Based on the available data, rV-CEA(6D)/TRICOM, rV-MUC-1, and rF-CEA(6D)/TRICOM in combination with sagramostim were well tolerated. There were no dose-limiting toxicities (DLTs) or serious adverse events causally related to the treatment regimen and no patient has withdrawn due to a DLT, inoculation-related event, or other adverse event related to the treatment. Adverse reactions causally related to the treatment regimen were limited to grade 1 and 2 events associated with local cutaneous injection site reactions and systemic events of fatigue, chills and fever.

As noted above, at the end of the 70-Day Core Treatment Phase, three patients entered into the Extension Phase of the Study. These three patients received five additional boosts of rF-CEA(6D)/TRICOM and were subsequently withdrawn from the study due to disease progression. No patients remain in the study. Twenty-one AEs, possibly or definitely related to vaccine, were reported in the three patients during the five-month period of the Extension Phase. All AEs related to the vaccine [rF-CEA(6D)/TRICOM] were of grade 1 severity. The most common AE was grade 1 erythema at the injection site following the monthly boosts. These data, although in a small number of patients, suggest that continued monthly boosts with fowlpox-based vaccines are well tolerated for more than 6 months.

All patients enrolled in Study PAN1-1 continue to be followed for survival data. Eight of the 12 patients enrolled in Study PAN1-1 have died. The median overall survival (OS) is 7.9 months: Of note, all of these patients had metastatic disease at baseline and all had failed first-line chemotherapy. Based on historical control data, the expected median OS in this patient population is approximately 3-4 months (Heinemann, Semin Oncol. 2002 December; 29(6 Suppl 20):9-16). Although the sample size is small and the analysis is limited by comparison to historical control data, these data are encouraging.

TBC-PAN-002

Clinical Trial Protocol TBC-PAN-002 was a Phase I open-label study to evaluate the safety and tolerability of PANVAC-VF in combination with sagramostim in the treatment of patients with adenocarcinoma of the pancreas. The study population includes patients ≥18 years of age who have histologically confirmed adenocarcinoma of the pancreas, whose disease is unresectable in the opinion of the investigator and who have a Karnofsky Performance Status of ≥80. Study patients must also have received prior vaccinia (smallpox immunization) and must be expected to live at least 4 months.

For TBC-PAN-002, patients received a 'prime' dose of $2 \times 10^8$ pfu PANVAC-V SC on Day 0, followed by a 'boost' dose of $1 \times 10^9$ pfu PANVAC-F SC on Days 14, 28, and 42. sagramostim (100 µg) is given SC at the injection site on the day of each vaccine administration and for three consecutive days thereafter.

Following Day 70, at the discretion of the Investigator, patients who were clinically stable were allowed to enter into an Extension Phase of continued vaccinations. Patients in the Extension Phase received monthly boosts of PANVAC-F at $1 \times 10^9$ pfu with sagramostim monthly until disease progression, as determined by the Investigator. During the Extension Phase, safety data will continue to be collected.

Safety parameters evaluated during the course of this study include medical history, vital signs, physical examination, laboratory tests (hematology, chemistry, urinalysis), and concomitant medications. Safety is assessed by examining these parameters and tabulating treatment-emergent adverse events occurring between baseline and Days 14, 28, 42, and 70. In addition, ECG readings were collected at baseline, Day 28, and Day 70, and an assessment of Karnofsky Performance Status was determined at baseline, Day 28 and Day 70. Out-of-range laboratory test results or other events not assessed as clinically significant changes from baseline are not reported as adverse events.

The most common AE (43%) related to the vaccines was injection site reaction at the site of vaccine administration. These AEs were all grade 1 and included erythema, swelling, pruritis, blister, induration, and pain. Notably, of the ten administrations of vaccinia virus (PANVAC-V), there were three grade 1 AEs (blister, erythema, and pruritis). Of note, all vaccinations in this study were administered subcutaneously (and will be in all future studies of PANVAC-VF). These data demonstrate that the AE profile related to subcutaneous administration of the vaccine is significantly more benign than the AE profile following intradermal administration by scarification. Intradermal administration of vaccinia is classically associated with the formation of vesicles, pustules, and scars, all of which may contain infectious virus. Thus, although injection sites were not cultured in the current study, the AE profile following PANVAC-V vaccination suggests that PANVAC-V may not be shed from the patient following vaccination. Administration of PANVAC-F was more commonly associated with injection site reactions. Of the 28 PANVAC-F vaccinations administered to the 10 patients, 20 were associated with AEs, and 15 of these 20 (75%) were limited to grade 1 erythema.

The majority of AEs related to the vaccine (63 of 74; 85%) were of grade 1 severity. There were ten grade 2 AEs related to the vaccine (five fatigue, three headache, one vomiting, one nausea). There was 1 grade 3 fever which was a dose-limiting toxicity (see below). Following injection site reactions, the most common AEs were fatigue, anorexia, nausea, vomiting, fever, headache, and myalgia. It is possible that several of these AEs may reflect a vaccine-related syndrome.

Twenty-three serious adverse events (SAEs) have been reported in five patients. All SAEs were classified as not related to the vaccine by the investigators. Three of the events (liver dysfunction/failure, pancreatic cancer disease progression, and recurrence of pneumonia) resulted in death. One patient experienced a Grade 3 Fever DLT which resolved without sequelae: this patient received the prime vaccine injection on Day 0, and boost vaccinations on Days 14 and 28. Sagramostim was administered per protocol following the Day 0 and Day 14 vaccinations. On the evening of Day 28, following the second administration of PANVAC-F and one administration of sagramostim, the patient noted a temperature of 104.5° F., which was a grade 3 reaction and a DLT, as the investigator classified this event as definitely related to vaccine. The patient was treated with 500 mg acetaminophen orally, and the event resolved without sequelae. This patient continued on the Study.

Based on the available preliminary data, PANVAC-VF in combination with sagramostim appears to be well tolerated and no clinically significant, serious adverse events causally related to the treatment regimen have thus far been observed. The median OS is 6.3 months.

TBC-PAN-003

Clinical Trial Protocol TBC-PAN-003 is a Phase III randomized, controlled study to evaluate the safety and efficacy of PANVAC-VF in combination with sargarmostim versus best supportive care or palliative chemotherapy in patients with metastatic (Stage IV) adenocarcinoma of the pancreas who have failed a gemcitabine-containing chemotherapy regimen. The protocol for treatment of patients in this clinical trial follows the protocol for TBC-PAN-002, described above.

We claim:

1. A method for inducing an immunological response against malignant pancreatic cells in an individual, wherein the method comprises:
   (a) selecting an individual having malignant pancreatic cells,
   (b) administering to the individual a first poxvirus vector comprising SEQ ID NO: 1 and SEQ ID NO: 3 and DNA sequences encoding ICAM-1, LFA-3, and B7.1, and
   (c) at regular intervals thereafter administering at least a second poxvirus vector comprising SEQ ID NO: 1 and SEQ ID NO: 3 and DNA sequences encoding ICAM-1, LFA-3, and B7.1,
   such that an immunological response against the malignant pancreatic cells is induced in the individual.

2. The method according to claim 1, wherein the first and second poxvirus vectors are selected from the group consisting of an orthopox virus vector; avipox virus vector; a suipox virus vector; a capripox virus vector; a leporipox virus vector; and an iridovirus vector.

3. The method according to claim 1, wherein the first poxvirus vector, the second poxvirus vector, or both the first and the second poxvirus vectors is a replication impaired or non-replicating poxvirus vector.

4. The method according to claim 3, wherein the first poxvirus vector, the second poxvirus vector, or both the first and the second poxvirus vectors is an orthopox vector.

5. The method according to claim 4, wherein the orthopox virus vector is vaccinia.

6. The method of claim 1, wherein the first poxvirus vector is an orthopox vector, and the second poxvirus vector is an avipox vector.

7. The method of claim 6, wherein the orthopox vector is vaccinia.

8. The method of claim 7, wherein the vaccinia is an attenuated vaccinia.

9. The method of claim 8, wherein the attenuated vaccinia is MVA or NYVAC.

10. The method of claim 6, wherein the orthopox vector is administered in one to three administrations at set intervals, and the avipox vector is administered in multiple administrations at set intervals.

11. The method of claim 10, wherein the set interval is 20 days to 90 days.

12. The method of claim 1, wherein the immunological response against a malignant pancreatic cell is a cell-mediated immune response.

13. The method of claim 12, wherein the cell-mediated immune response is against malignant pancreatic cells expressing CEA and MUC.

14. A method of inhibiting growth of malignant pancreatic cells in an individual, wherein the method comprises:
   (a) selecting an individual having malignant pancreatic cells,
   (b) administering to the individual a first poxvirus vector comprising SEQ ID NO: 1 and SEQ ID NO: 3 and DNA sequences encoding ICAM-1, LFA-3, and B7.1, and
   (c) at regular intervals thereafter administering at least a second poxvirus vector comprising SEQ ID NO: 1 and SEQ ID NO: 3 and DNA sequences encoding ICAM-1, LFA-3, and B7.1,
   such that the growth of the malignant pancreatic cells is inhibited in the individual.

15. The method according to claim 14, wherein the first and second poxvirus vectors are selected from the group consisting of an orthopox virus vector; avipox virus vector; a suipox virus vector; a capripox virus vector; a leporipox virus vector; and an iridovirus vector.

16. The method according to claim 14, wherein the first poxvirus vector, the second poxvirus vector, or both the first and the second poxvirus vectors is a replication impaired or non-replicating poxvirus vector.

17. The method according to claim 16, wherein the first poxvirus vector, the second poxvirus vector, or both the first and the second poxvirus vectors is an orthopox vector.

18. The method according to claim 17, wherein the orthopox virus vector is vaccinia.

19. The method of claim 14, wherein the first poxvirus vector is an orthopox vector, and the second poxvirus vector is an avipox vector.

20. The method of claim 19, wherein the orthopox vector is vaccinia.

21. The method of claim 20, wherein the vaccinia is an attenuated vaccinia.

22. The method of claim 21, wherein the attenuated vaccinia is MVA or NYVAC.

23. The method of claim 19, wherein the orthopox vector is administered in one to three administrations at set intervals, and the avipox vector is administered in multiple administrations at set intervals.

24. The method of claim 23, wherein the set interval is 20 days to 90 days.

* * * * *

SEQUENCE LISTING

```
<160> NUMBER OF SEQ ID NOS: 6

<210> SEQ ID NO 1
<211> LENGTH: 1548
<212> TYPE: DNA
<213> ORGANISM: Homo sapiens

<400> SEQUENCE: 1
atgacaccgg gcacccagtc tcctttcttc ctgctgctgc tcctcacagt gcttacagtt      60
gttacgggtt ctggtcatgc aagctctacc ccaggtggag aaaaggagac ttcggctacc     120
cagagaagtt cagtgcccag ctctactgag aagaatgctg tgagtatgac aagctccgta     180
ctctccagcc acagcccggg ttcaggctcc tccaccactc agggacagga tgtcactctg     240
gccccggcca cggaaccagc ttcaggttca gctgccttgt ggggacagga tgtcacctcg     300
gtaccagtta ctagaccagc tttaggtagc acagcacctc ctgctcatgg agtaactagt     360
gctcctgata ctcgtccagc tcctggcagt actgcaccac cggcacatgg cgtaacatca     420
gcacctgata caagacctgc acctggatct acagcgccgc ctgcgcacgg agtgacatcg     480
gcgcccgata cgcgccccgc tcccggtagc accgcaccgc ccgcccacgg tgttacaagt     540
gcacccgata cccggccggc acccggaagt accgctccac ctgcacacgg ggtcacaagc     600
gcgccagaca ctcgacctgc gccagggtcg actgccccct cggcgcatgg tgtgacctca     660
gctcctgaca caaggccagc cccagctagc actctggtgc acaacggcac ctctgccagg     720
gctaccacaa ccccagccag caagagcact ccattctcaa ttcccagcca ccactctgat     780
actcctacca cccttgccag ccatagcacc aagactgatg ccagtagcac tcaccatagc     840
acggtacctc ctctcacctc ctccaatcac agcacttctc cccagttgtc tactggggtc     900
```

```
tctttcttt   tcctgtcttt   tcacatttca   aacctccagt   ttaattcctc   tctggaagat   960
cccagcaccg  actactacca   agagctgcag   agagacattt   ctgaaatgtt   tttgcagatt  1020
tataaacaag  ggggttttct   gggcctctcc   aatattaagt   tcaggccagg   atctgtggtg  1080
gtacaattga  ctctggcctt   ccgagaaggt   accatcaatg   tccacgacgt   ggagacacag  1140
ttcaatcagt  ataaaacgga   agcagcctct   cgatataacc   tgacgatctc   agacgtcagc  1200
gtgagtgatg  tgccatttcc   tttctctgcc   cagtctgggg   ctggggtgcc   aggctgggc   1260 atcgcgctgc  tggtgctggt   ctgtgttctg   gttgcgctgg   ccattgtcta   tctcattgcc  1320
ttggctgtct  gtcagtgccg   ccgaaagaac   tacgggcagc   tggacatctt   ccagcccgg   1380 gataccttacc atcctatgag   cgagtacccc   acctaccaca   cccatgggcg   ctatgtgccc  1440
cctagcagta  ccgatcgtag   cccctatgag   aaggtttctg   caggtaatgg   tggcagcagc  1500
ctctcttaca  caaacccagc   agtggcagcc   acttctgcca   acttgtag                 1548
```

<210> SEQ ID NO 2
<211> LENGTH: 515
<212> TYPE: PRT
<213> ORGANISM: Homo sapiens

<400> SEQUENCE: 2

```
Met Thr Pro Gly Thr Gln Ser Pro Phe Phe Leu Leu Leu Leu Thr
 1               5                  10                  15

Val Leu Thr Val Val Thr Gly Ser Gly His Ala Ser Ser Thr Pro Gly
            20                  25                  30

Gly Glu Lys Glu Thr Ser Ala Thr Gln Arg Ser Ser Val Pro Ser Ser
        35                  40                  45

Thr Glu Lys Asn Ala Val Ser Met Thr Ser Ser Val Leu Ser Ser His
    50                  55                  60

Ser Pro Gly Ser Gly Ser Ser Thr Thr Gln Gly Gln Asp Val Thr Leu
65                  70                  75                  80

Ala Pro Ala Thr Glu Pro Ala Ser Gly Ser Ala Ala Leu Trp Gly Gln
                85                  90                  95

Asp Val Thr Ser Val Pro Val Thr Arg Pro Ala Leu Gly Ser Thr Ala
            100                 105                 110

Pro Pro Ala His Gly Val Thr Ser Ala Pro Asp Thr Arg Pro Ala Pro
        115                 120                 125

Gly Ser Thr Ala Pro Pro Ala His Gly Val Thr Ser Ala Pro Glu Thr
    130                 135                 140

Arg Pro Ala Pro Gly Ser Thr Ala Pro Pro Ala His Gly Val Thr Ser
145                 150                 155                 160

Ala Pro Asp Thr Arg Pro Ala Pro Gly Ser Thr Ala Pro Pro Ala His
                165                 170                 175

Gly Val Thr Ser Ala Pro Asp Thr Arg Pro Ala Pro Gly Ser Thr Ala
            180                 185                 190

Pro Pro Ala His Gly Val Thr Ser Ala Pro Asp Thr Arg Pro Ala Pro
        195                 200                 205

Gly Ser Thr Ala Pro Pro Ala His Gly Val Thr Ser Ala Pro Asp Thr
    210                 215                 220

Arg Pro Ala Pro Ala Ser Thr Leu Val His Asn Gly Thr Ser Ala Arg
225                 230                 235                 240

Ala Thr Thr Thr Pro Ala Ser Lys Ser Thr Pro Phe Ser Ile Pro Ser
                245                 250                 255
```

| | | | | | | | | | | | |
|---|---|---|---|---|---|---|---|---|---|---|---|
|His|His|Ser|Asp|Thr|Pro|Thr|Thr|Leu|Ala|Ser|His|
| | |260| | | |265| | | |270| |
|Ser|Thr|Lys|Thr| | | | | | | | |

Asp Ala Ser Ser Thr His His Ser Thr Val Pro Pro Leu Thr Ser Ser
    275             280             285

Asn His Ser Thr Ser Pro Gln Leu Ser Thr Gly Val Ser Phe Phe Phe
    290             295             300

Leu Ser Phe His Ile Ser Asn Leu Gln Phe Asn Ser Ser Leu Glu Asp
305             310             315             320

Pro Ser Thr Asp Tyr Tyr Gln Glu Leu Gln Arg Asp Ile Ser Glu Met
            325             330             335

Phe Leu Gln Ile Tyr Lys Gln Gly Gly Phe Leu Gly Leu Ser Asn Ile
            340             345             350

Lys Phe Arg Pro Gly Ser Val Val Gln Leu Thr Leu Ala Phe Arg
            355             360             365

Glu Gly Thr Ile Asn Val His Asp Val Glu Thr Gln Phe Asn Gln Tyr
    370             375             380

Lys Thr Glu Ala Ala Ser Arg Tyr Asn Leu Thr Ile Ser Asp Val Ser
385             390             395             400

Val Ser Asp Val Pro Phe Pro Phe Ser Ala Gln Ser Gly Ala Gly Val
            405             410             415

Pro Gly Trp Gly Ile Ala Leu Leu Val Leu Val Cys Val Leu Val Ala
            420             425             430

Leu Ala Ile Val Tyr Leu Ile Ala Leu Ala Val Cys Gln Cys Arg Arg
            435             440             445

Lys Asn Tyr Gly Gln Leu Asp Ile Phe Pro Ala Arg Asp Thr Tyr His
    450             455             460

Pro Met Ser Glu Tyr Pro Thr Tyr His Thr His Gly Arg Tyr Val Pro
465             470             475             480

Pro Ser Ser Thr Asp Arg Ser Pro Tyr Glu Lys Val Ser Ala Gly Asn
            485             490             495

Gly Gly Ser Ser Leu Ser Tyr Thr Asn Pro Ala Val Ala Ala Thr Ser
            500             505             510

Ala Asn Leu
        515

<210> SEQ ID NO 3
<211> LENGTH: 2106
<212> TYPE: DNA
<213> ORGANISM: Homo sapiens

<400> SEQUENCE: 3

```
atggagtctc cctcggcccc tccccacaga tggtgcatcc cctggcagag gctcctgctc      60
acagcctcac ttctaaccct ctggaacccg cccaccactg ccaagctcac tattgaatcc     120
acgccgttca tgtcgcaga ggggaaggag gtgcttctac ttgtccacaa tctgccccag     180 catcttttg gctacagctg gtacaaaggt gaaagagtgg atgcaaccg tcaaattata      240 ggatatgtaa taggaactca acaagctacc ccagggcccg catacagtgg tcgagagata     300
atatacccca tgcatccct gctgatccag aacatcatcc agaatgacac aggattctac     360
accctacacg tcataaagtc agatcttgtg aatgaagaag caactggcca gttccgggta     420
tacccggaac tccctaagcc ttctattagc tccaataata gtaagcctgt cgaagacaaa     480
gatgccgtcg cttttacatg cgagcccgaa actcaagacg caacatatct ctggtgggtg     540
aacaaccagt ccctgcctgt gtcccctaga ctccaactca gcaacggaaa tagaactctg     600
```

-continued

| | |
|---|---|
| accctgttta acgtgaccag gaacgacaca gcaagctaca aatgcgaaac ccaaaatcca | 660 |
| gtcagcgcca ggaggtctga ttcagtgatt ctcaacgtgc tttacggacc cgatgctcct | 720 |
| acaatcagcc ctctaaacac aagctataga tcaggggaaa atctgaatct gagctgtcat | 780 |
| gccgctagca atcctcccgc ccaatacagc tggtttgtca atggcacttt ccaacagtcc | 840 |
| acccaggaac tgttcattcc caatattacc gtgaacaata gtggatccta cacgtgccaa | 900 |
| gctcacaata gcgacaccgg actcaaccgc acaaccgtga cgacgattac cgtgtatgag | 960 |
| ccaccaaaac cattcataac tagtaacaat tctaacccag ttgaggatga ggacgcagtt | 1020 |
| gcattaactt gtgagccaga gattcaaaat accacttatt tatggtgggt caataaccaa | 1080 |
| agtttgccgg ttagcccacg cttgcagttg tctaatgata ccgcacatt gacactcctg | 1140 |
| tccgttactc gcaatgatgt aggaccttat gagtgtggca ttcagaatga attatccgtt | 1200 |
| gatcactccg accctgttat ccttaatgtt ttgtatggcc cagacgaccc aactatatct | 1260 |
| ccatcataca cctactaccg tcccggcgtg aacttgagcc tttcttgcca tgcagcatcc | 1320 |
| aaccccctg cacagtactc ctggctgatt gatggaaaca ttcagcagca tactcaagag | 1380 |
| ttatttataa gcaacataac tgagaagaac agcggactct atacttgcca ggccaataac | 1440 |
| tcagccagtg gtcacagcag gactacagtt aaaacaataa ctgtttccgc ggagctgccc | 1500 |
| aagccctcca tctccagcaa caactccaaa cccgtggagg acaaggatgc tgtggccttc | 1560 |
| acctgtgaac ctgaggctca gaacacaacc tacctgtggt gggtaaatgg tcagagcctc | 1620 |
| ccagtcagtc ccaggctgca gctgtccaat ggcaacagga ccctcactct attcaatgtc | 1680 |
| acaagaaatg acgcaagagc ctatgtatgt ggaatccaga actcagtgag tgcaaaccgc | 1740 |
| agtgacccag tcaccctgga tgtcctctat gggccggaca ccccatcat ttccccccca | 1800 |
| gactcgtctt accttcggg agcggacctc aacctctcct gccactcggc ctctaaccca | 1860 |
| tccccgcagt attcttggcg tatcaatggg ataccgcagc aacacacaca agttctcttt | 1920 |
| atcgccaaaa tcacgccaaa taataacggg acctatgcct gttttgtctc taacttggct | 1980 |
| actggccgca ataattccat agtcaagagc atcacagtct ctgcatctgg aacttctcct | 2040 |
| ggtctctcag ctggggccac tgtcggcatc atgattggag tgctggttgg ggttgctctg | 2100 |
| atatag | 2106 |

<210> SEQ ID NO 4
<211> LENGTH: 371
<212> TYPE: PRT
<213> ORGANISM: Homo sapiens

<400> SEQUENCE: 4

Asn Ser Asn Pro Val Glu Asp Glu Asp Ala Val Ala Leu Thr Cys Glu
 1               5                  10                  15

Pro Glu Ile Gln Asn Thr Thr Tyr Leu Trp Trp Val Asn Asn Gln Ser
            20                  25                  30

Leu Pro Val Ser Pro Arg Leu Gln Leu Ser Asn Asp Asn Arg Thr Leu
        35                  40                  45

Thr Leu Leu Ser Val Thr Arg Asn Asp Val Gly Pro Tyr Glu Cys Gly
    50                  55                  60

Ile Gln Asn Glu Leu Ser Val Asp His Ser Asp Pro Val Ile Leu Asn
65                  70                  75                  80

Val Leu Tyr Gly Pro Asp Asp Pro Thr Ile Ser Pro Ser Tyr Thr Tyr
                85                  90                  95

Tyr Arg Pro Gly Val Asn Leu Ser Leu Ser Cys His Ala Ala Ser Asn

```
            100                 105                 110
Pro Pro Ala Gln Tyr Ser Trp Leu Ile Asp Gly Asn Ile Gln Gln His
        115                 120                 125

Thr Gln Glu Leu Phe Ile Ser Asn Ile Thr Glu Lys Asn Ser Gly Leu
    130                 135                 140

Tyr Thr Cys Gln Ala Asn Asn Ser Ala Ser Gly His Ser Arg Thr Thr
145                 150                 155                 160

Val Lys Thr Ile Thr Val Ser Ala Glu Leu Pro Lys Pro Ser Ile Ser
                165                 170                 175

Ser Asn Asn Ser Lys Pro Val Glu Asp Lys Asp Ala Val Ala Phe Thr
            180                 185                 190

Cys Glu Pro Glu Ala Gln Asn Thr Thr Tyr Leu Trp Trp Val Asn Gly
        195                 200                 205

Gln Ser Leu Pro Val Ser Pro Arg Leu Gln Leu Ser Asn Gly Asn Arg
    210                 215                 220

Thr Leu Thr Leu Phe Asn Val Thr Arg Asn Asp Ala Arg Ala Tyr Val
225                 230                 235                 240

Cys Gly Ile Gln Asn Ser Val Ser Ala Asn Arg Ser Asp Pro Val Thr
                245                 250                 255

Leu Asp Val Leu Tyr Gly Pro Asp Thr Pro Ile Ile Ser Pro Pro Asp
            260                 265                 270

Ser Ser Tyr Leu Ser Gly Ala Asp Leu Asn Leu Ser Cys His Ser Ala
        275                 280                 285

Ser Asn Pro Ser Pro Gln Tyr Ser Trp Arg Ile Asn Gly Ile Pro Gln
    290                 295                 300

Gln His Thr Gln Val Leu Phe Ile Ala Lys Ile Thr Pro Asn Asn Gly
305                 310                 315                 320

Thr Tyr Ala Cys Phe Val Ser Asn Leu Ala Thr Gly Arg Asn Asn Ser
                325                 330                 335

Ile Val Lys Ser Ile Thr Val Ser Ala Ser Gly Thr Ser Pro Gly Leu
            340                 345                 350

Ser Ala Gly Ala Thr Val Gly Ile Met Ile Gly Val Leu Val Gly Val
        355                 360                 365

Ala Leu Ile
    370

<210> SEQ ID NO 5
<211> LENGTH: 31
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 5
ggtaccggta ccatggaagg ggaagggtt c                                    31

<210> SEQ ID NO 6
<211> LENGTH: 31
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 6
cttggttcat ggtgacactg agctcgagct c                                   31
```